United States Patent
Morra et al.

(10) Patent No.: US 10,588,321 B2
(45) Date of Patent: Mar. 17, 2020

(54) METHOD FOR USING MUSTARD MEAL OR AN EXTRACT THEREOF

(71) Applicant: University of Idaho, Moscow, ID (US)

(72) Inventors: Matthew J. Morra, Moscow, ID (US); Inna E. Popova, Moscow, ID (US); Jeremiah Dubie, Medford, OR (US)

(73) Assignee: University of Idaho, Moscow, ID (US)

( * ) Notice: Subject to any disclaimer, the term of this patent is extended or adjusted under 35 U.S.C. 154(b) by 91 days.

(21) Appl. No.: 15/863,680

(22) Filed: Jan. 5, 2018

(65) Prior Publication Data

US 2018/0125077 A1    May 10, 2018

Related U.S. Application Data

(63) Continuation of application No. PCT/US2016/041361, filed on Jul. 7, 2016.

(60) Provisional application No. 62/190,552, filed on Jul. 9, 2015.

(51) Int. Cl.
| | |
|---|---|
| *A61K 36/31* | (2006.01) |
| *A01N 65/00* | (2009.01) |
| *A01N 65/08* | (2009.01) |
| *A01N 25/02* | (2006.01) |

(52) U.S. Cl.
CPC .......... *A01N 65/00* (2013.01); *A01N 65/08* (2013.01); *A01N 25/02* (2013.01)

(58) Field of Classification Search
None
See application file for complete search history.

(56) References Cited

U.S. PATENT DOCUMENTS

| | | | |
|---|---|---|---|
| 1,875,473 A | 9/1932 | McKee | |
| 8,450,244 B2* | 5/2013 | Robinson | A01N 65/08 504/118 |
| 2008/0182751 A1* | 7/2008 | Morra | A01N 47/46 504/117 |
| 2011/0237778 A1 | 9/2011 | Reaney et al. | |
| 2013/0085117 A1* | 4/2013 | Wagner | A01N 59/16 514/53 |
| 2014/0090100 A1* | 3/2014 | Ripley | A01H 1/04 800/264 |
| 2017/0238570 A1* | 8/2017 | Waxman | A23L 19/12 |
| 2017/0347666 A1* | 12/2017 | Robinson | A01N 65/08 |

OTHER PUBLICATIONS

International Search Report and Written Opinion dated Oct. 14, 2016 from International Application No. PCT/US2016/041361 (13 pages).
Meyer et al., "Mustard seed meal mixtures: management of Meloidogyne incognita on pepper and potential phytotoxicity," *Journal of Nematology* 43(1): Mar. 7-15, 2011.
Molina et al., "Potato early dying and yield responses to compost, green manures, seed meal and chemical treatments," *American Journal of Potato Research* 91:414-428, Feb. 25, 2014.
Tickoo et al., "Indian mustard (*Brassica juncea*): A potential fungicide for control of early blight (Alternaria solani) of potato," *12th IRC* 4:205-208, Wuhan, China 2007.
Townsend, "The Ammonium Thiocyanate Treatment for Hastening the Sprouting of Dormant Bliss Triumph Potatoes," *Florida State Horticultural Society* 58:236-237, 1945.
Vaughn et al., "Herbicidal activity of glucosinolate-containing seedmeals," *Weed Science* 54:743-748, 2006.
Wathelet et al., "Guidelines for glucosinolate analysis in green tissue used for biofumigation," *Agroindustria* 3(3):259-266, 2004.

\* cited by examiner

*Primary Examiner* — Ralph J Gitomer

(57) ABSTRACT

Disclosed are embodiments of a method of using mustard meal or mustard meal extract. Certain embodiments concern controlling vegetable sprouting, such as potato sprouting. Vegetables, such as potatoes, may be exposed to products resulting from mustard meal, or an extract thereof, contacting water. Other embodiments concern a process for controlling plant pests, such as insects, nematodes, fungi, weeds, and combinations thereof, with specific embodiments being particularly useful for weed suppression. Certain embodiments comprise extracting glucosinolates from plant material, or processed plant material, selected from the family Brassicaceae, particularly from the genera *Brassica* and *Sinapis*. Extracted glucosinolates can be hydrolyzed to form active compounds, or alternatively, they can be hydrolyzed in situ, by simultaneously or sequentially applying myrosinase. The extract can be applied to plants, to the soil adjacent to the plant.

20 Claims, 26 Drawing Sheets

Control          *B. juncea* (5 g) + 30 mL water

METHOD FOR USING MUSTARD MEAL OR AN EXTRACT THEREOF

CROSS REFERENCE TO RELATED APPLICATION

This is a U.S. continuation application of International Application No. PCT/US2016/041361, filed on Jul. 7, 2016, which was published in English under PCT Article 21(2), which in turn claims the benefit of the earlier filing date of U.S. provisional patent application No. 62/190,552, filed Jul. 9, 2015, both of which are incorporated herein by reference in their entireties.

ACKNOWLEDGMENT OF GOVERNMENT SUPPORT

This invention was made with government support under Agriculture and Food Research Initiative competitive grant 2011-67009-20094 awarded by United States Department of Agriculture National Institute of Food and Agriculture. The government has certain rights in the invention.

FIELD

Disclosed embodiments of the present invention concern extracts from *Sinapis alba* or *Brassica juncea* and their use in agriculture.

BACKGROUND

Currently, there is a strong desire by consumers to use products that are produced without using synthetic pesticides. Many commonly used pesticides are no longer used, or their use soon will be discontinued. For example, the use of methyl bromide is being restricted. This desire for consumers to have substantially synthetic pesticide-free materials must be balanced by the practicalities required for feeding an ever-increasing world-wide population. Thus, some method of controlling weeds and/or insects must be implemented.

Farmers throughout the world are constantly looking for ways to improve soil quality, reduce inputs, and enhance yield and produce quality. The use of plant materials to suppress soil-borne pests and plant pathogens has been referred to as "biofumigation" and the species used as "biofumigants." Pest and disease suppression are not the only advantages of using biofumigants. Species such as oilseed radish have shown high potential to increase soil aeration and to scavenge residual nitrogen. Several research studies have recently been published and many are currently ongoing throughout the nation and the world to better understand and quantify the contributions of biofumigants to cropping systems.

Plants may produce compounds that directly or indirectly affect their biological environment. These compounds fall within a broad category of compounds called allelochemicals, and are exclusive of food that influences growth, health, or behavior of other organisms. One reason for interest in allelochemicals is their potential for use in alternative pest management systems. Using plant-produced allelochemicals in agricultural and horticultural practices could minimize synthetic pesticide use, reduce the associated potential for environmental contamination, and contribute to a more sustainable agricultural system.

SUMMARY

Disclosed herein are embodiments of a method comprising controlling potato sprouting by using *Brassica juncea* seed meal or extract or a combination thereof. The amount of *Brassica juncea* seed meal or extract or a combination thereof, used may be up to one gram per 225 kg of potatoes, such as from one gram per 1.5 kg to one gram per 50 kg of potatoes. In some embodiments, controlling comprises exposing potatoes to first products made by forming a first aqueous composition comprising the *Brassica juncea* seed meal or extract or a combination thereof. Exposing the potatoes may comprise forming the first aqueous composition in the presence of the potatoes; applying the first products to the potatoes; spraying or fogging the atmosphere of a potato storage facility with the first products, or a combination thereof. Forming the first aqueous composition may comprise using an amount of water sufficient to make the first products, such as from 1 mL to 30 mL, or from 5 mL to 10 mL per gram of *Brassica juncea* seed meal or extract or a combination thereof. The *Brassica juncea* seed meal or extract or a combination thereof, may comprise an amount of sinigrin sufficient to produce an amount of hydrolysis products sufficient to substantially preclude potato sprouting. The amount may be from greater than zero to 2000 µmol, or from 350 µmol to 1000 µmol per gram of *Brassica juncea* seed meal or extract or a combination thereof.

Certain embodiments comprise exposing the potatoes to second products made by forming a second aqueous composition comprising *Brassica juncea* seed meal or extract or a combination thereof. A time period between the potatoes being exposed to the first and second products may be sufficient to substantially maintain inhibition of potato sprouting, such as from 1 week to 12 weeks, or from 4 weeks to 8 weeks. Particular embodiments comprise exposing potatoes to first products made by forming a first composition comprising from 5 mL to 10 mL of water and one gram of *Brassica juncea* seed meal or extract or a combination thereof, for every 200 pounds of potatoes; and exposing the potatoes to second products at a time point of from 4 weeks to 8 weeks after exposing the potatoes to the first products, the second products being made by forming a second composition comprising from 5 mL to 10 mL of water and one gram of *Brassica juncea* seed meal or extract or a combination thereof, for every 200 pounds of potatoes.

Also disclosed are embodiments of a process for controlling plant pests and/or suppressing weeds in plant crops. For example, the method may be practiced to control insects, nematodes, fungi, weeds, and combinations thereof, with specific embodiments being particularly useful for weed suppression. One disclosed embodiment comprises extracting plant material selected from the family Brassicaceae, particularly from the genera *Brassica* and *Sinapis*, and more particularly from *Sinapis alba* or *Brassica juncea*. In some embodiments, the plant material is a seed meal. The plant material may be homogenized and/or ground prior to the extraction.

The plant material is extracted with a solvent system comprising an alcohol and water. The extracts thus obtained are concentrated and dried by suitable techniques including spray drying or belt drying, to produce non-deliquescent solids. The extraction solvent may comprise from 10% to 90% alcohol and from 90% to 10% water. The alcohol comprise methanol, ethanol or a combination thereof.

In particular embodiments, the plant material is *Sinapis alba*, and the extraction solvent comprises 30% ethanol and 70% water. The extraction may be performed for a period of time up to at least 3 days, such as from greater than zero to 12 hours, from greater than zero to 24 hours, from greater than zero to 48 hours, or from greater than zero to 72 hours. The extract may comprise 4-hydroxybenzyl alcohol, SCN$^-$, and/or 4-hydroxyphenylacetonitrile. In other embodiments, the plant material is *Brassica juncea* and the extraction solvent is 70% ethanol and 30% water.

The extracts may be spray dried, belt dried or freeze dried.

Also disclosed herein are embodiments of a method for using the extracts. The extract may be applied to liverwort, or to the soil adjacent to liverwort. The extract may comprise 4-hydroxybenzyl alcohol, $SCN^-$, and 4-hydroxyphenylacetonitrile. The seed meal or an extract thereof may also be applied to potatoes to prevent or substantially inhibit growth of potato sprouts. In some embodiments, the extracts are formulated as a solution in water.

The foregoing and other objects, features, and advantages of the invention will become more apparent from the following detailed description, which proceeds with reference to the accompanying figures.

DETAILED DESCRIPTION

I. Terms and Introduction

Figure 1:
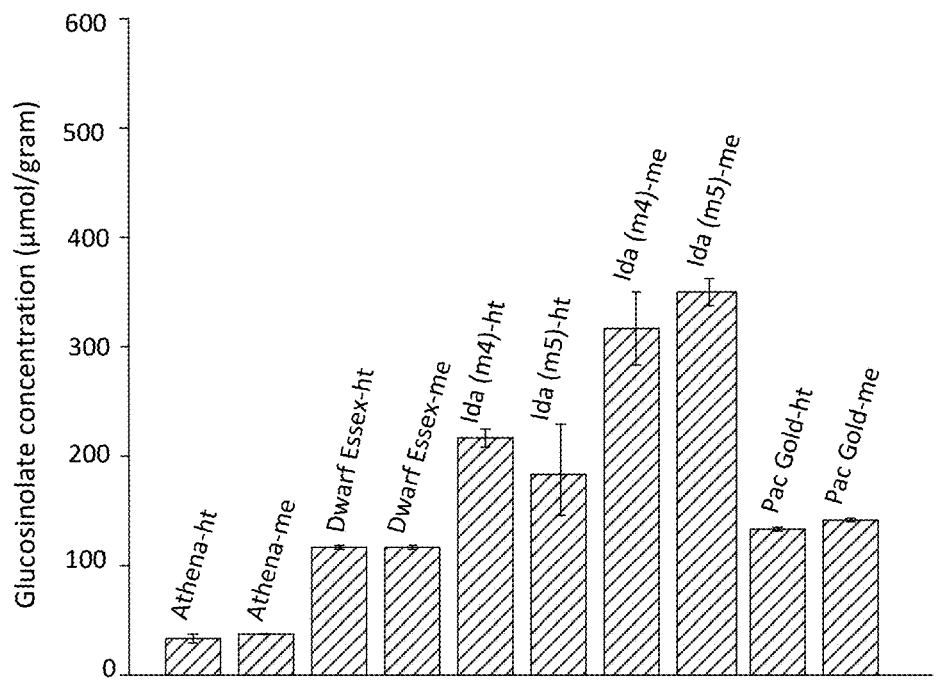
FIG. 1 is a graph of glucosinolate concentrations (μmol glucosinolates per gram seed meal determined without using a response factor) for various plant materials as determined using hot water (ht) and methanol (me) extractions. Athena and Dwarf Essex are *B. napus* species, Ida is a *S. alba* species, and Pac Gold is a *B. juncea* species. Ida samples m4 and m5 represent two different *S. alba* meal samples.

The following term definitions are provided to aid the reader, and should not be considered to provide a definition different from that known by a person of ordinary skill in the art. And, unless otherwise noted, technical terms are used according to conventional usage.

As used herein, the singular terms "a," "an," and "the" include plural referents unless context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

In order to facilitate review of the various examples of this disclosure, the following explanations of specific terms are provided:

Derivative: A derivative is a molecule derived from a base structure.

Effective amount: An amount of bioactive agent that is useful for producing a desired effect.

Plant material: A whole plant or portion(s) thereof including but not limited to plant tissue, leaves, stems, roots, seeds, and/or flowers.

Purified: The term "purified" does not require absolute purity; rather, it is intended as a relative term. For example, a purified compound is one that is isolated in whole or in part from contaminants.

II. Biopesticide Plant Materials

The present application is primarily directed to using plant material or processed plant material, extracts from plant material or processed plant material, or compositions comprising the same, as biopesticides. The present disclosure is particularly directed to using extracts of plant material from plants within the order Capparales, and the family Brassicaceae. Even more typically, the plant material is from the genera *Brassica* and *Sinapis*, particularly *Sinapis*. Representative species of *Brassica* include *hirta*, *juncea* and *napus*. Representative species of *Sinapis* include *Sinapis alba* and *Sinapis arvenis*. *Brassica juncea* and *Sinapis alba* being currently preferred plants useful for their biopesticidal properties.

III. Ionic Thiocyanate Production

Another basis for determining plant material within the scope of the present invention is to select plant material that includes glucosinolates that produce ionic thiocyanate ($SCN^-$). Thus, any plant material that produces glucosinolates in a high enough concentration to produce ionic thiocyanate in a biologically active concentration is within the scope of the present invention. More specifically, preferred plant material produces 4-hydroxybenzyl glucosinolate, or derivatives thereof, resulting in the production of ionic thiocyanate.

IV. Glucosinolates and Glucosinolate Concentrations

Glucosinolates, found in dicotyledonous plants, are a class of organic anions usually isolated as potassium or sodium salts, but occasionally in other forms. For example, p-hydroxybenzyl glucosinolate is isolated as a salt complex with sinapine, an organic cation derived from choline. Features common to the class are a ß-D-thioglucose moiety, a sulfate attached through a C=N bond (sulfonated oxime), and a side group (designated R) that distinguishes one glucosinolate from another. A general formula for glucosinolates is provided below.

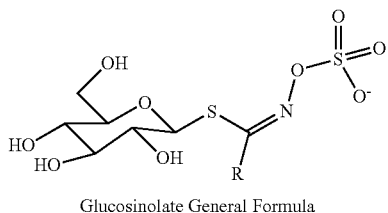

Glucosinolate General Formula

More than 116 different R groups, and thus glucosinolates, have been identified or inferred from degradative products.

Glucosinolate types in plant species are highly variable. For example, the main glucosinolate in radish seed (*Raphanus sativus*) is 4-methylsulphinyl-3-butenyl glucosinolate, while mustard seed (*Brassica juncea*) is dominated by 2-propenyl glucosinolate. Cabbage seed (*Brassica oleracea*) contains mainly 2-propenyl and 2-hydroxy-3-butenyl glucosinolate. Rapeseed (*Brassica napus*) contains 4 major glucosinolates: 2-hydroxy-3-butenyl, 3-butenyl, 4-pentenyl, and 2-hydroxy-4-pentenyl. Similar differences in glucosinolate types are observed when comparing vegetative plant parts.

*Brassica* and *Sinapis* species, and many other members of the Brassicaceae plant family, produce glucosinolate compounds, which are secondary metabolites. Thus, the method may also comprise determining plants potentially useful for practicing disclosed embodiments of the present invention by choosing plants that produce glucosinolates in amounts effective for use as a biopesticide. Glucosinolates are compounds that occur in agronomically important crops and may represent a viable source of allelochemic control for various soil-borne plant pests. Glucosinolates can be extracted from plant material using aqueous extractions, using polar organic compounds, such as lower alkyl alcohols as the solvent, or by using aqueous mixtures of polar organic compounds to perform extractions, as illustrated by FIG. 1.

Glucosinolates are normally stored within plant tissues. Toxicity is not attributed to intact glucosinolates. Upon tissue damage, enzymes within the plant trigger their hydrolysis to several compounds including nitriles, isothiocyanates (ITCs, —N=C=S), organic cyanides, oxazolidinethiones (OZTs), and ionic thiocyanate ($SCN^-$), that are released upon enzymatic degradation by myrosinase (thioglucoside glucohydrolase, EC 3.2.3.1) in the presence of water as indicated below in Scheme 1. Degradation also occurs thermally or by acid hydrolysis. Toxicity is generally attributed to these bioactive products.

Myrosinase is not properly identified as a single enzyme, but rather as a family or group of similar-acting enzymes. Multiple forms of the enzymes exist, both among species and within a single plant, and all perform a similar function. Although their genetic sequences are similar to other ß-glycosidases, myrosinases are fairly specific toward glucosinolates. These enzymes cleave the sulfur-glucose bond regardless of either the enzyme or substrate source. However, the particular enzyme and glucosinolate substrate influence reaction kinetics.

Myrosinase and glucosinolates are separated from each other in intact plant tissues. Glucosinolates are probably contained in vacuoles of various types of cells. In contrast, myrosinase is contained only within structures, called myrosin grains, of specialized myrosin cells that are distributed among other cells of the plant tissue. In cold-pressed meal, myrosinase and glucosinolates are no longer physically separated, and myrosinase activity is preserved. Thus, adding water immediately results in the production of the hydrolysis products, including isothiocyanate, without the need for additional tissue maceration.

Nitrile character is common to four additional products. Forming a nitrile (R—C≡N, also known as an organic cyanide), which does not require rearrangement, involves sulfur loss from the molecule. Nitrile formation is favored over ITC at low pH, but occurs in some crucifers at a pH where ITC is normally the dominant product. The presence of $Fe^{2+}$ or thiol compounds increases the likelihood of nitrile formation and decreases the proportion of $SCN^-$ production. However, previously $SCN^-$ was thought to be the primary phytotoxic compound and therefore methods were directed to maximizing its production, not decreasing it. The work described herein, for example with liverwort, surprisingly indicated that the nitrile was much more phytotoxic than $SCN^-$. Also, the 4-OH benzyl alcohol is more phytotoxic that $SCN^-$.

Epithionitrile formation requires the same conditions as for nitriles, plus terminal unsaturation of the R-group and the presence of an epithiospecifier protein. The epithiospecifier protein possesses a rare property in that it is an enzyme cofactor that allosterically directs an enzyme to yield a different product. Thiocyanate (R—S—C≡N) is sometimes produced, particularly in members of the *Alyssum, Coronopus, Lepidium*, and *Thlaspi* families. Factors controlling organic thiocyanate formation are not well understood.

Figure 2:
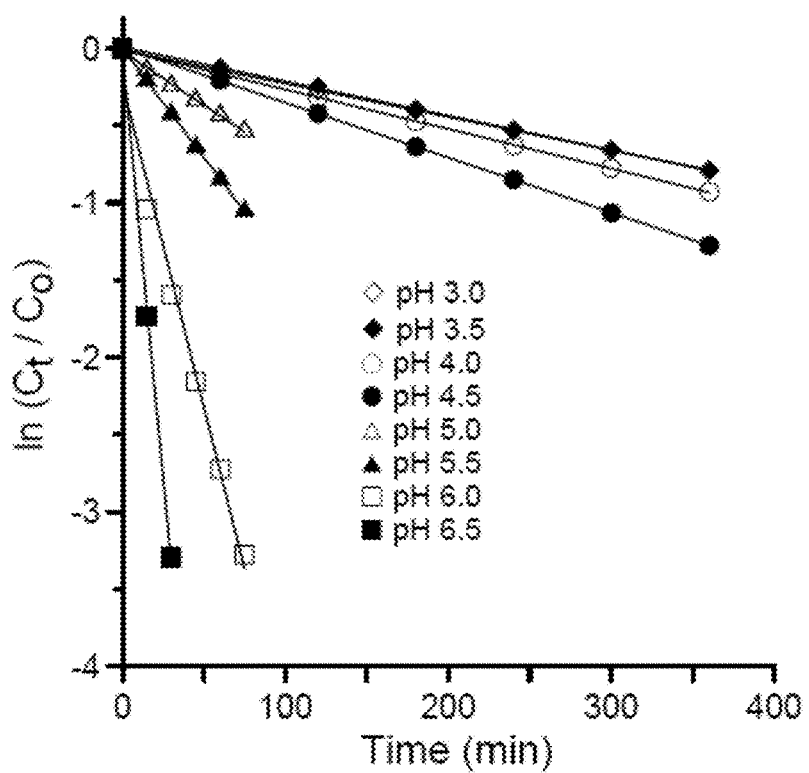
FIG. 2 provides first-order plots for the disappearance of 4-hydroxybenzyl isothiocyanate incubated in buffered aqueous solutions with pH values ranging from 3.0 to 6.5, where plots for pH 3.0 and 3.5 are superimposed on each other in the graph.

$SCN^-$ production from glucosinolates is controlled by the presence of specific R-groups. Evidence suggests the anion is a resonance hybrid with greater charge on the S; however, charge can be localized on either the sulfur ($^-$S—C≡N) or the nitrogen (S=C=$N^-$), depending on the environment. Indole and 4-hydroxybenzyl glucosinolates yield $SCN^-$ that is thought to arise from a highly unstable ITC intermediate. $SCN^-$ is formed from indole glucosinolates over a wide pH range, whereas 4-hydroxybenzyl glucosinolates is typically thought to yield $SCN^-$ only at a more basic pH. As discussed below and in the working examples, 4-OH benzyl isothiocyanate is not stable even at pH values of 3.0. The half-life decreases with an increase in pH from 3.6 hours at pH 3.0 to less than 5 minutes at pH 7.0 (FIG. 2).

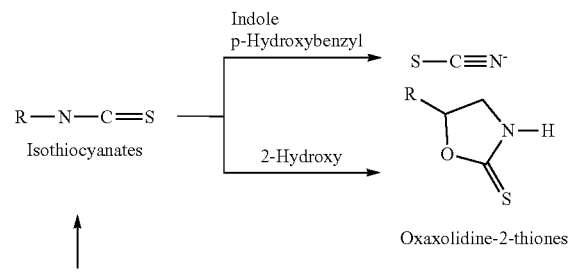

Scheme 1

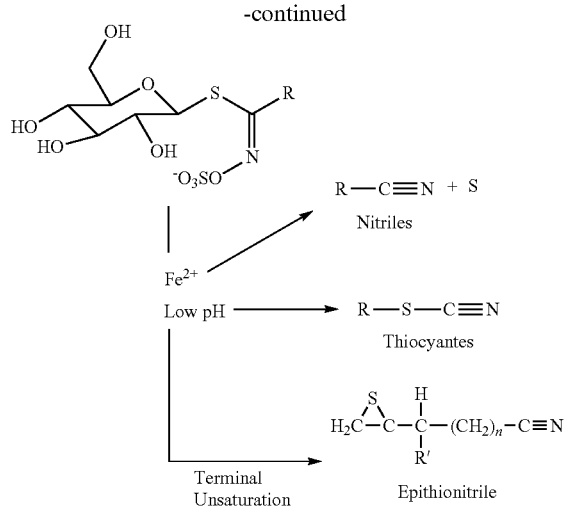

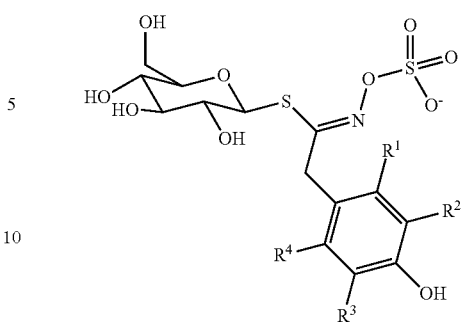

ITCs historically have been considered the 'normal' products of glucosinolate breakdown. They often are volatile with pungent flavors or odors. Some of the hydrolysis products, like ITCs, exhibit biocidal properties on insects, nematodes, fungi and/or weeds. ITC formation requires that the initial unstable aglucon intermediate undergo a Loessen rearrangement to the R—NCS configuration. Isothiocyanates are quite reactive, although less so than the related isocyanates (R—N═C═O). A few commercially available soil fumigants depend on the activity of methyl ITC either as the parent compound or as produced from precursors such as sodium N-methyldithiocarbamate or tetrahydro-3,5-dimethyl-2H-1,3,5-thiadiazine-2-thione. Because of known toxicities, ITCs are often considered likely candidates for pesticidal activity.

For *Sinapis alba*, the glucosinolate precursor to bioactive compounds is 4-hydroxybenzyl glucosinolate. Thus, the amount of this compound found in plants provides another basis for determining plant material useful for practicing embodiments of the disclosed invention. The structural formula for 4-hydroxybenzyl glucosinolate is provided below.

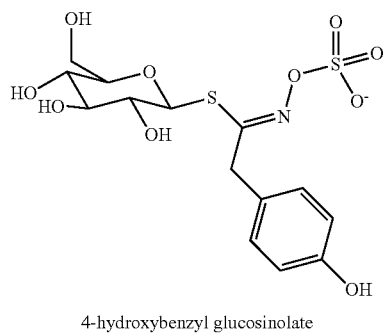 [SMILES: O=S(=O)([O-])O/N=C(/Cc1ccc(O)cc1)SC1OC(CO)C(O)C(O)C1O]

4-hydroxybenzyl glucosinolate

A person of ordinary skill in the art will appreciate that certain derivatives of 4-hydroxybenzyl glucosinolate also potentially may be useful for practicing disclosed embodiments of the present invention. For example, naturally occurring or synthetic derivatives may include plural hydroxyl groups, as opposed to the single hydroxyl group present at the 4 position in 4-hydroxybenzyl glucosinolate. Such derivatives might have a chemical formula where one or more of $R^1$, $R^2$, $R^3$ and $R^4$ optionally are hydroxyl groups. It also will be appreciated that the hydroxyl groups present in 4-hydroxybenzyl glucosinolate, or derivatives thereof, may be present in some other form, such as a protected form, that produces the desired hydroxyl groups, such as by hydrolysis or enzymatic cleavage.

Moreover, halide derivatives also may be useful. As a result, one or more of $R^1$, $R^2$, $R^3$ and $R^4$ optionally may be a halide. Benzyl glucosinolates substituted in the meta position (3-OH benzyl glucosinolate) or those with functional groups that prevent electron delocalization (4-methoxybenzyl glucosinolate) will degrade to more stable isothiocyanates. The stability of the isothiocyanate may be important for the use of seed meal products in pest control given the differences in biological activities of the glucosinolate hydrolysis products.

Figure 3:
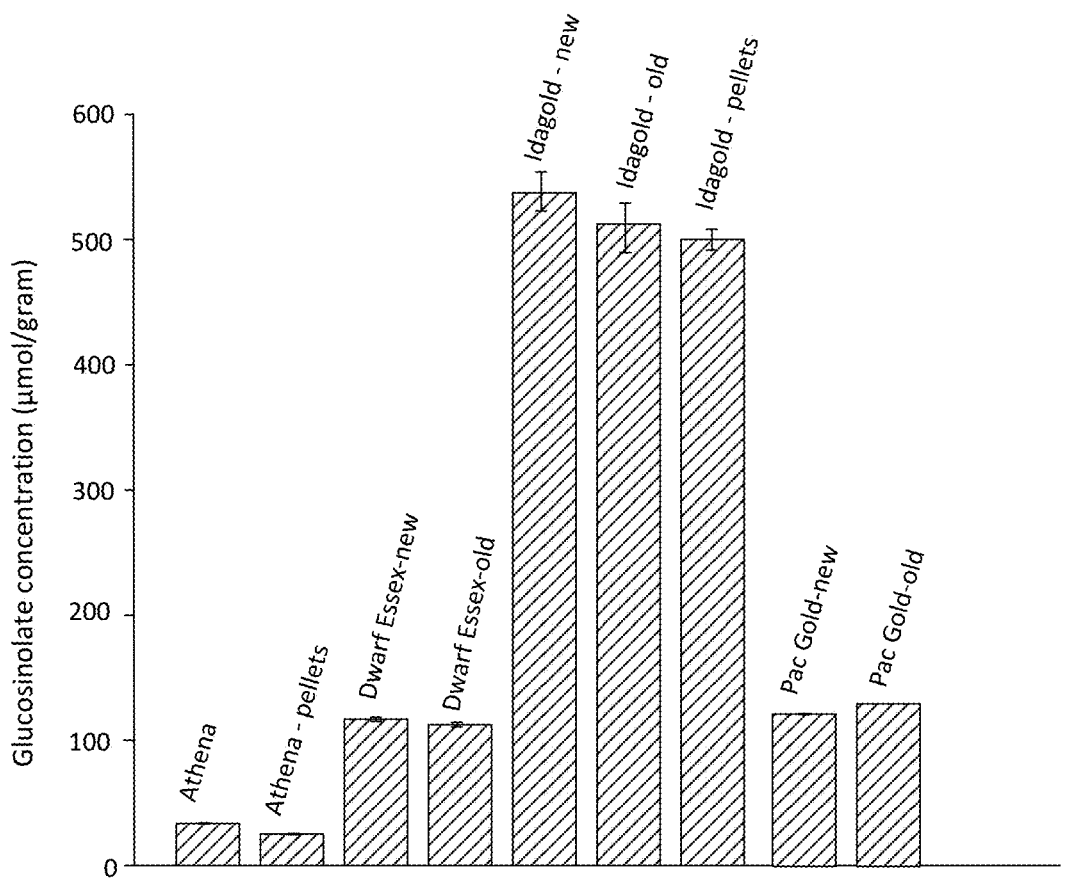
FIG. 3 is a graph of glucosinolate concentrations (μmol glucosinolates per gram seed meal determined without using a response factor) for various plant materials to compare total glucosinolates in stored (old) or freshly pressed (new) meals. Athena and Dwarf Essex are *B. napus* species, IdaGold is a *S. alba* species, and Pac Gold is a *B. juncea* species.

The concentrations of 4-hydroxybenzyl glucosinolate in plant material correspond to the amounts of ionic thiocyanate ($SCN^-$) produced by such materials. A standardized methodology is used to quantitatively determine amounts of such bioactive compounds. This is the subject of *Guidelines for Glucosinolate Analysis in Green Tissues for Biofumigation*, Agroindustria, Vol. 3, No. 3 (2004), which is incorporated herein by reference. This publication discusses modifications of the ISO 9167-1 method, initially set up for evaluating rapeseed seeds, with the objective of optimizing and standardizing glucosinolate analysis in fresh tissues (leaves, roots or stems) of Brassicaceae. Collection, storage and preparation of fresh samples suitable to be analyzed are important steps during which it is necessary to avoid glucosinolate hydrolysis by the endogenous myrosinase-catalyzed reaction. Differences in glucosinolate concentrations in stored, processed and fresh meal are illustrated by FIG. 3.

For disclosed embodiments of the present disclosure, 4-hydroxybenzyl glucosinolate concentrations were determined using HPLC/MS. Additional information concerning determining glucosinolate concentrations is provided below in the working examples, using an internal standard, such as 4-methoxy benzyl glucosinolate. In summary, the concentration of the 4-hydroxybenzyl glucosinolate is measured, such as by determining the area under the appropriate HPLC peak. The concentration is multiplied by a response factor of 0.5 relative to 2-propenyl glucosinolate to determine the concentration of 4-hydroxybenzyl glucosinolate.

Figure 4:
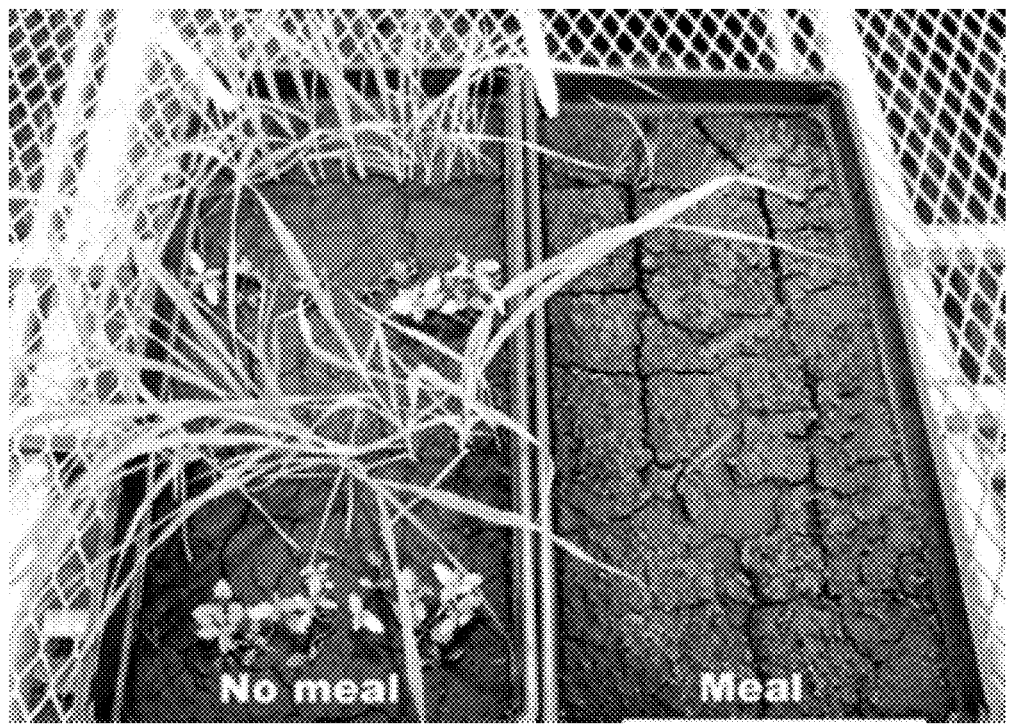
FIG. 4 is a photograph illustrating the effects of *Sinapis alba* for weed control as compared to a no-meal control in a greenhouse trial conducted with soil. The weeds include wild oat and redroot pigweed.

Certain disclosed embodiments concern plant material having effective amounts of 4-hyroxybenzyl glucosinolate. The glucosinolate concentration typically is determined after plant material has been cold pressed to remove a majority of the plant oil. Residual oil contents for cold pressed plants typically range from substantially 0% to about 15%, more typically from 7% to 12%. If solvent extraction is used for oil removal, oil contents may be less than 1%. Glucosinolate concentrations may vary within plants of a single species, and concentration fluctuations may occur within a particular plant. Additional environmental factors such as spacing, moisture regime, and nutrient availability also may affect concentration. Nevertheless, useful 4-hydroxybenzyl glucosinolate amounts are from about 10 μmol/gram to about 500 μmol/gram, typically from about 10 μmol/gram to about 400 μmol/gram, more typically from about 50 μmol/gram to about 250 μmol/gram, and even more typically from about 75 μmol/gram to about 210 μmol/gram. Concentrations within these stated ranges have proved useful for controlling and/or suppressing weed formation in plant growth studies. FIG. 4 is an image illustrating the effects of *Sinapis alba* for weed production beside a control in a greenhouse trial.

V. Seed Meal

Portions of plant material, leaves, stems, roots and seeds that have the highest concentration of glucosinolate commonly are used to practice embodiments of the disclosed process. Meal is preferably made from seeds; however it is possible to use any plant material containing glucosinolate to make the meal. For example, with reference to the exemplary *Sinapis alba* plant material, it has been found that the seeds contain the highest levels of 4-hydroxybenzyl glucosinolate. *Sinapis alba* is useful for making biodiesel. In a working embodiment, biodiesel production crushes the seeds, to liberate the oil, leaving the seed meal as a by-product. This by-product had limited use prior to development of the present invention. The seed meal now can be used to practice embodiments of the presently disclosed process.

VI. Extraction

In some embodiments, glucosinolates are extracted from the plant material or processed plant material, such as seed meal produced by the production of biodiesel. Extracting glucosolinolates from the plant material or processed plant material has several advantages. It can significantly reduce the effects of batch-to-batch variability resulting from variability in plant growing conditions, processing and storage. Also, the cost and logistics of transportation, storage, and application of mustard meal are relatively high compared to extracts of the same. And the introduction of large amounts of meal to the soil may result in a large organic carbon load (mustard contains up to 80% of organic carbon by weight), which can create some adverse effects such as growth of undesirable microorganisms.

Additionally, the extracts are typically stable in storage for at least three months at 25° C., and up to a year or more at −4° C. The extracts are typically not light sensitive, are thermally stable up to 120° C., and do not promote mold growth. In some embodiments, the extracts may have at least twice the concentration of active ingredients as mustard meal, such as up to three times, up to four times, or more than four times the concentration. The extracts can be prepared either as a powder, or as a solution in variety of active agent concentrations as required for different applications. The use of such solutions makes the extracts compatible with spray delivery systems.

The plant material or processed plant material is extracted using a solvent system suitable for extracting glucosinolates from the plant material. The solvent system used for the extraction may be a single solvent or mixture of solvents. Typically, an aqueous solvent system is used for the extraction, such as a solvent system comprising water and alkyl alcohol. The alkyl alcohols may comprise one or more $C_1$-$C_4$ alkyl alcohols, such as methanol, ethanol, propanol, isopropanol, n-butanol, isobutanol, sec-butanol or tert-butanol. In some embodiments, a single alcohol is used, but in other embodiments, two or more alcohols are used, such as a mixture of methanol and ethanol.

The solvent system may comprise from greater than 0% to 100% water and from less than 100% to 0% alcohol, such as from 10% to 90% water and from 90% to 10% alcohol, or from 30% to 70% water and from 70% to 30% alcohol. In some embodiments, a ratio of water to alcohol is selected to inhibit or substantially prevent the glucosinolates from hydrolyzing during the extraction. In such embodiments, the percentage of alcohol in the solvent system is from 60% to less than 100%, such as from 65% to 95% or from 70% to 90%. In certain embodiments, seed meal, such as *B. juncea* seed meal, is extracted with an extraction solvent comprising, consisting essentially of, or consisting of from 60% to less than 100% alcohol and from greater than zero to 40% water, such as from 60% to 90% alcohol and from 10% to 40% water, from 60% to 80% alcohol and from 20% to 40% water, or from 65% to 75% alcohol and from 25% to 35% water, and in particular embodiments, the seed meal is extracted with an extraction solvent comprising, consisting essentially of, or consisting of about 70% alcohol and 30% water. In certain embodiments, the alcohol is ethanol.

Alternatively, the ratio of water to alcohol may be selected to promote hydrolysis of the glucosinolates during the extraction. In such embodiments, the solvent system typically comprises an excess of water. The solvent system may comprise from 60% to 100% water and from 40% to 0% alcohol, such as from 70% to 90% water and from 30% to 10% alcohol. The extraction process may continue for a time period suitable to allow hydrolysis of the glucosinolates. In some embodiments, the extraction is performed for up to 5 days, such as up to 3 days, or from 2 to 3 days, to allow for extraction and hydrolysis to take place.

The water may comprise a buffer, to maintain the pH at a level suitable for hydrolysis of the glucosinolates. In some embodiments, the buffer was selected to maintain a pH of from 6 to 7.2 during the extraction. In some embodiments, twice as much buffer was required for the extraction of *S. alba* as was required from *B. juncea*, such as twice the concentration of buffer. Examples of suitable buffers include, but are not limited to, phosphate, carbonate, bicarbonate buffers or combinations thereof. In particular embodiments, sodium bicarbonate is used as the buffer.

The extracts may be filtered to remove any solid material, and then evaporated by any suitable technique known to a person of ordinary skill in the art, to remove the extraction solvent(s). Suitable techniques include, but are not limited to, rotary evaporation, optionally under vacuum, spray drying, belt drying, drum drying, freeze drying or any combination thereof. In certain embodiments, spray drying is preferred. Typically, the evaporation and/or drying will produce a solid extract, which may be in the form of a powder, such as a free-flowing powder.

Glucosinolates themselves are not biologically active and can be preserved in extracts for prolong amount of time. However, in the presence of water, they are converted by the endogenous enzyme myrosinase (thioglucoside glucohydrolase, EC 3.2.1.147) into biologically active compounds. The major glucosinolate in *S. alba*, sinalbin, is hydrolyzed to an unstable isothiocyanate that non-enzymatically produces $SCN^-$, a phytotoxic compound (Scheme 2). The major glucosinolate in *B. juncea*, sinigrin, is hydrolyzed to produce a volatile, bioactive 2-propenyl isothiocyanate.

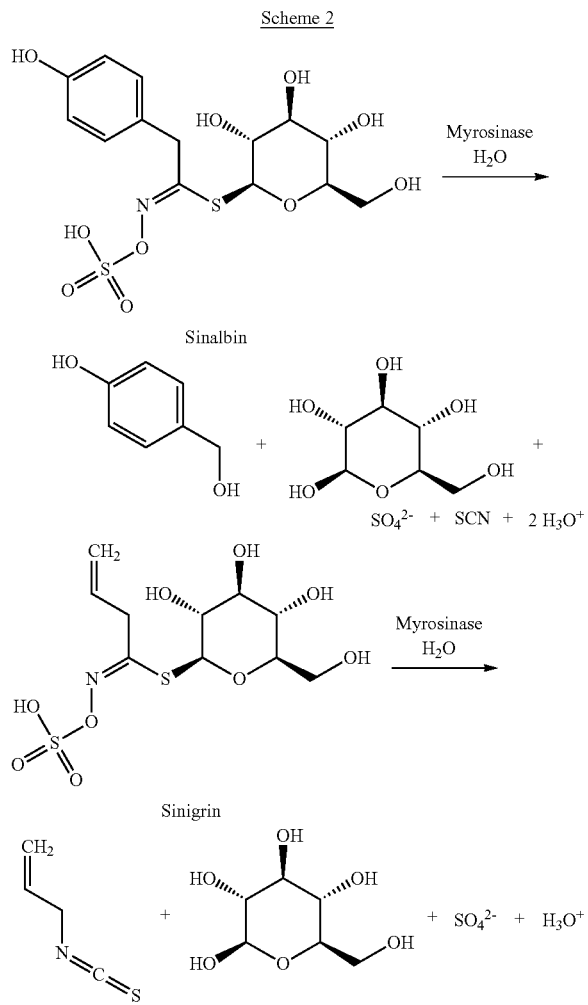

Scheme 2

Myrosinase is present in mustard meal, such as *S. alba* and *B. juncea* meal. Thus, mustard meal may be added to an aqueous solution of glucosinolates to aid hydrolysis. The aqueous solution also may comprise a buffer, such as a phosphate buffer, carbonate buffer, bicarbonate buffer, or a combination thereof, to maintain a pH preferable for the activity of the enzyme. In some embodiments, the pH is from about 5 to about 8, such as from 6 to 7.5. Mustard meal can swell up in aqueous solution, by up to about 400%. Therefore, the amount of mustard meal added to the aqueous solution typically does not exceed 20% by weight, to allow for recovery of the liquid. In some embodiments, the amount of mustard meal is further limited to allow for reasonable recovery of the desired products, and may be 10% or less by weight, such as 7% or less or 4% or less.

Hydrolysis of mustard extract can be performed prior to the application to the field. For example, an extract from *S. alba* containing sinalbin can be hydrolyzed to yield a stable ionic thiocyanate solution. This solution can be applied through the existing sprinkler or sprayer systems for control of weeds. Alternatively, hydrolysis of mustard extract can be performed in situ, when mustard extract is applied to the field and then hydrolyzed directly at the point of pest control. This approach is particularly useful for pest and nematode control by the volatile, allyl isothiocyanate hydrolysis product of sinigrin from *B. juncea*.

VII. Compositions

The plant material or processed plant material, or extracts thereof may be used as prepared or extracted, or they may be formulated with other materials to facilitate their bioactive properties. The material or extracts may be formulated as a solution to aid delivery by sprinkler systems or spraying devices. Also, myrosinase may be added to aid hydrolysis of the glusocinolates to the isothiocyanates. Compositions may also include a buffer, such as a phosphate buffer, to aid maintaining an effective pH, for example, to facilitate effective myrosinase activity.

The material or extracts may be formulated into a solid form, such as a pellet, capsule, granule or powder. The solid formulation may also comprise one or more enzymes to aid hydrolysis, such as Myrosinase, and/or a buffer, such as a phosphate buffer. The advantages of storing extracts as a solid compared to storing allyl isothiocyanate itself include increased worker safety and decreased danger resulting from storing a gaseous, highly toxic compound. The allyl isothiocyanate then can be produced when needed, by contacting the solid-formulated extract with water. The advantage as compared to using an allyl isothiocyanate itself is increased worker safety, as the pesticide is produced only when needed. As long as the extract is kept dry, possible human exposure is minimized. The pellet or capsule will contain the extract, buffer, and enzyme. This has important safety implications with respect to using the extracts as sprout inhibitors or as pesticides applied to soils or the environment.

Furthermore, the extracts of plant products prepared according to the present disclosure also can be formulated with other materials to facilitate useful fumigant attributes, or to facilitate other processes, such as fertilization processes. $SCN^-$ often works synergistically with other chemicals. For example, use with certain peroxides produces bactericidal solutions, although neither is effective alone. Similarly, $SCN^-$ was more efficient in lysing cells when combined with other anions or lysozymes than when any agent was used alone at the same concentrations.

Thus, the plant material or processed plant material or extracts thereof, and/or compositions thereof disclosed herein can be combined with other materials, natural and/or synthetic, inert and/or active, to produce useful fertilizing and/or fumigant compositions. A partial list of such materials include inert materials, such as binders, colorants, and/or pH adjusters/stabilizers; active compounds, such as naturally derived pesticide materials including capsaicin, onions, Neem tree materials, or compositions derived therefrom, such as *Bacillus thuringiensis*, microorganisms such as pseudomonads, peroxides, synthetic herbicides, surfactants and combinations thereof.

Furthermore, plant material or processed plant material or extracts thereof or compositions thereof disclosed herein also can be formulated with other materials to provide essential plant nutrients, such as phosphorus. With respect to nitrogen, the seed meal of *Sinapis alba*, for example, provides high concentrations of nitrogen (5-6% on a weight basis), and hence added nitrogen is not required.

VIII. Methods for Using

Once the disclosed extracts or compositions are obtained, they are then applied as needed and desired to take advantage of their biopesticidal properties. For example, extracts of plant material or processed plant material, or compositions thereof, can be applied as surface applications, such as bare soil prior to planting. As used herein, "surface application" refers to applications that penetrate only the top portion of a soil, such as about 0.1 inch (about 0.25 centimeter) of the soil.

Additionally, an extract of plant material or processed plant material, or compositions thereof, may be applied directly on to a weed or the soil adjacent to the weed. The soil adjacent to the weed may be of from immediately next to the weed to a suitable distance from the weed such that application of the extract substantially inhibits growth of the weed or kills the weed. In particular embodiments, the extract is applied directly to the weed by a suitable technique, such as spraying. The extract may be added to water to form a solution, suspension or emulsion suitable for spraying. The extract may comprise one or more hydrolysis products before application. Alternatively, the extract may comprise glucosinolate and be mixed with myrosinase or a myrosinase-containing composition such as mustard meal, typically in a buffered aqueous media, at the time of application, or immediately before. This helps prevent volatile isothiocyanates such as allyl isothiocyanate, from substantially evaporating in storage prior to use. In an alternative embodiment, a solution of extract comprising the glucosinolates and a composition may be applied sequentially in any order, or substantially at the same time, thereby allowing the isothiocyanates to form in situ as the glucosinolates and myrosinase mix on the plant or in the soil.

Certain food crops are resistant to active compounds provided by the extracts of plant material or processed plant material. As a result, the method also can include applying such extracts at the same time as food crops are planted. Alternatively, the method can include applying such extracts after emergence of food crops. For example, carrot seeds in both pelleted and un-pelleted form germinate in the presence of an extract of *Sinapis alba* meal when provided at concentrations sufficient to kill or significantly damage weeds, such as those specifically identified in this application. Carrots appear more "tolerant" to the SCN$^-$ produced by *S. alba* meal as compared to such crops as lettuce.

Additionally, the growth of sprouts in vegetables can be inhibited or substantially prevented during storage of harvested vegetables, by the using seed meal or an extract of plant material or processed plant material, such as the seed meal. In some embodiments, vegetable sprouting is controlled, such as inhibited to substantially prevented, by using *Brassica juncea* seed meal or extract or a combination thereof. Vegetables suitable for use in the disclosed method include any vegetable that may sprout during storage. The sprouting vegetable may be a bulb vegetable, such as onion, garlic, shallot, or chive; a corm vegetable, such as taro, water chestnut, or eddoe; or a tuber vegetable, such as a stem or root tuber vegetable. Exemplary stem tuber vegetables include, but are not limited to, potatoes, Jerusalem artichokes, or yams, such as Chinese yams, purple yams, white yams, and winged yams. Exemplary root tuber vegetables include, but are not limited to, cassava or dahlia.

In some embodiments, the growth of sprouts in vegetables, for example, in potatoes, can be inhibited or substantially prevented during storage of harvested vegetables, by the using seed meal or an extract of plant material or processed plant material, such as the seed meal. In some embodiments, vegetable sprouting, such as potato sprouting, is controlled, such as inhibited to substantially prevented, by using *Brassica juncea* seed meal or extract or a combination thereof. Suitable potatoes include any potato such as, for example, Russet Burbank, Russet Norkotah, Western Russet, Cal Red, Red La Soda, Norland, French Fingerling, Russian Banana, Purple Peruvian, Yukon Gold, Yukon Gem, Ruby Cresent, Yellow Finn, Huckleberry, Ida Rose, Klondike Golddust, Klondike Rose, Milva, Ranger Russet, All Blue, Alturas Russet, Bannock Russet, Bintje, Blazer Russet, Classic Russet, Clearwater Russet, Onaway, Elba, Carola, Oliense, Cecil, Allian, Agata, Russet Alpine, Rosara, Chieftan, Dark Red Norland, Red Norland, Innovator, Shepody, California Whites, or a combination thereof. The seed meal or extract may be prepared as an aqueous composition, such as an aqueous solution, suspension or emulsion. In some embodiments, vegetable sprouting, such as potato sprouting, is controlled, such as inhibited or substantially prevented, by exposing the vegetables to products formed by forming the composition. The products may be volatile products. In some embodiments, the products comprise an ITC. Control of potato sprouting by the products is unexpected because thiocyanate compounds, that have a —SCN moiety, such as sodium thiocyanate (NaSCN), potassium thiocyanate (KSCN) or ammonium thiocyanate (NH$_4$SCN), have been shown to promote potato sprouting. See, for example, U.S. Pat. No. 1,875,473, and Florida State Horticultural Society Proceedings, 1945, vol. 58, pages 236-237.

Figure 5:
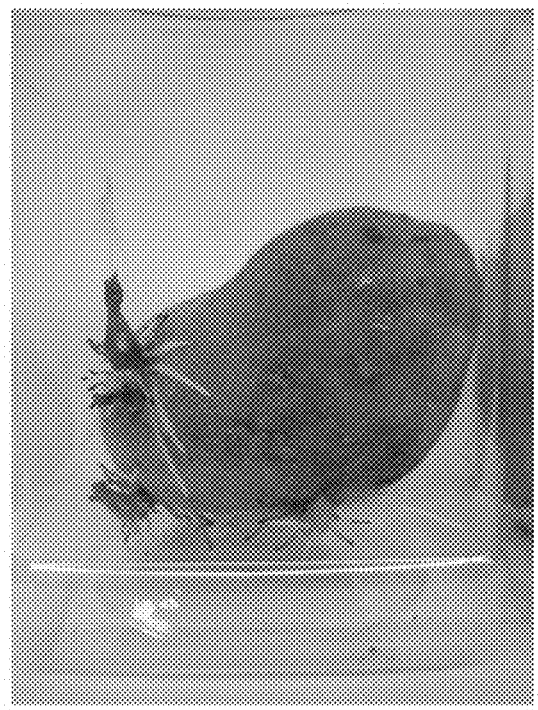
FIG. 5 provides two photographs of potatoes, illustrating that the growth of potato sprouts is inhibited or substantially prevented by treatment with *B. juncea* seed meal and water.
Figure 5:
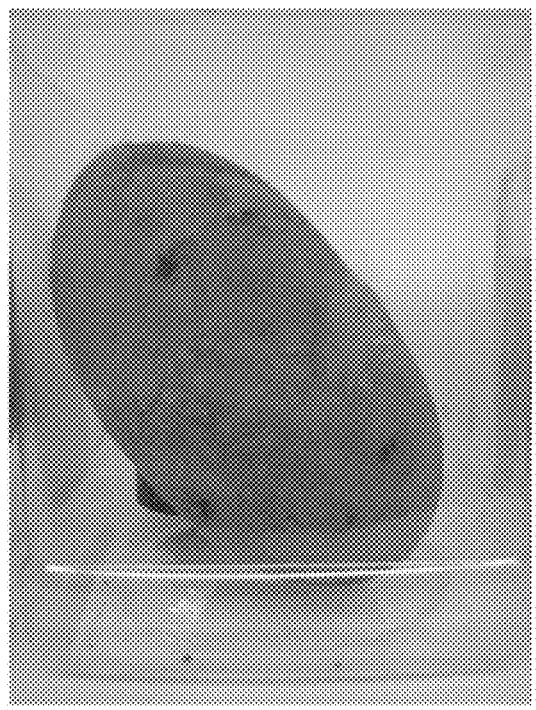

The vegetables, such as potatoes, may be exposed to the products by any suitable technique, such as spraying, fogging the atmosphere, and/or exposing in a container or room, such as a sealed container or room. In some embodiments, the aqueous composition is formed, such as by contacting the seed meal or extract with water, in the presence of the vegetables. For example, FIG. 5 shows two photographs of potatoes in sealed containers. One potato is exposed to *B. juncea* seed meal and water; the other is a control. After three weeks at 25° C. and a diurnal light cycle, the control potato has produced sprouts, whereas the seed meal-treated potato has not.

The concentration of extract or seed meal, such as *B. juncea* seed meal or extract thereof, in a solution, suspension, or emulsion is selected to effectively prevent sprout growth on the vegetables, such as potatoes. In some embodiments, the amount of solvent, such as water, that is used per gram of extract or seed meal is from greater than zero to 50 mL or more, such as from 1 mL to 30 mL, from 2 mL to 25 mL, from 3 mL to 20 mL, from 4 mL to 15 mL, or from 5 mL to 10 mL, and in certain disclosed embodiments, 7 mL, 14 mL or 28 mL of solvent was used per gram of extract or seed meal. The vegetables may be exposed once to the composition and/or the products formed by forming the composition, or they may be repeatedly exposed, as necessary, to prevent sprout growth. For repeated applications, a time period between applications is selected such that inhibition of vegetable sprout growth, such as potato sprout growth, is maintained, such as from greater than zero days to 12 weeks or more, from 1 week to 10 weeks, from 2 weeks to 8 weeks, or from 4 weeks to 8 weeks. The amount of seed meal, or extract thereof, used to control the vegetable sprouting, such as potato sprouting, is one gram for from greater than zero to 500 pounds or more of the vegetables, such as from 1 pound to 400 pounds, from 2 pounds to 300 pounds, from 3 pounds to 250 pounds, or from 4 pounds to 200 pounds per gram of extract or seed meal. In other embodiments, the seed meal or extract thereof, is used in an amount of one gram for every 500 pounds or fraction thereof of the vegetables, for example, potatoes, such as one gram for every 400 pounds or fraction thereof, one gram for every 300 pounds or fraction thereof, one gram for every 250 pounds or fraction thereof, or one gram for every 200 pounds or fraction thereof of the vegetables. Alternatively, the amount of seed meal or extract, such as *Brassica juncea* seed meal or extract or a combination thereof, may be up to one gram per 225 kg or more of the vegetables, such as potatoes, such as from one gram per 1 kg of vegetables to one gram per 100 kg of vegetables, or from one gram per 1.5 kg of vegetables to one gram per 50 kg of vegetables.

The extract or seed meal may comprise an amount of sinigrin sufficient such that upon forming an aqueous composition, a sufficient amount of hydrolysis products are formed to inhibit and/or substantially prevent vegetable, such as potato, sprouting. The amount of sinigrin in the extract or seed meal may be from greater than zero to 2,000 µmol or more per gram of extract, such as from 100 µmol/g to 1,750 µmol/g, from 200 µmol/g to 1,500 µmol/g, from 300 µmol/g to 1,250 µmol/g, or from 350 µmol/g to 1,000 µmol/g of extract or seed meal.

On a large scale, vegetable storage sheds, such as potato storage sheds, can be fumigated with the volatile products formed by forming an aqueous composition of *Brassica juncea* seed meal or extract or a combination thereof. The volatile products may comprise 2-propenyl isothiocyanate. The vegetable storage sheds can be fumigated by any suitable technique, such as by spraying or fogging the atmosphere of the storage facility. Using a volatile compound can be a benefit. For example, the volatile 2-propenyl isothiocyanate will substantially evaporate from the vegetables before they are consumed by people. A low residual amount of the isothiocyanate remaining on the vegetables is unlikely to be toxic. The chemical responsible for the sharp taste of horseradish is 2-propenyl isothiocyanate, the same active ingredient in mustard. At low concentrations, isothiocyanates are considered anticarcinogenic, and 2-propenyl isothiocyanate is registered with EPA as a biopesticide.

IX. Pest Control

Figure 6:
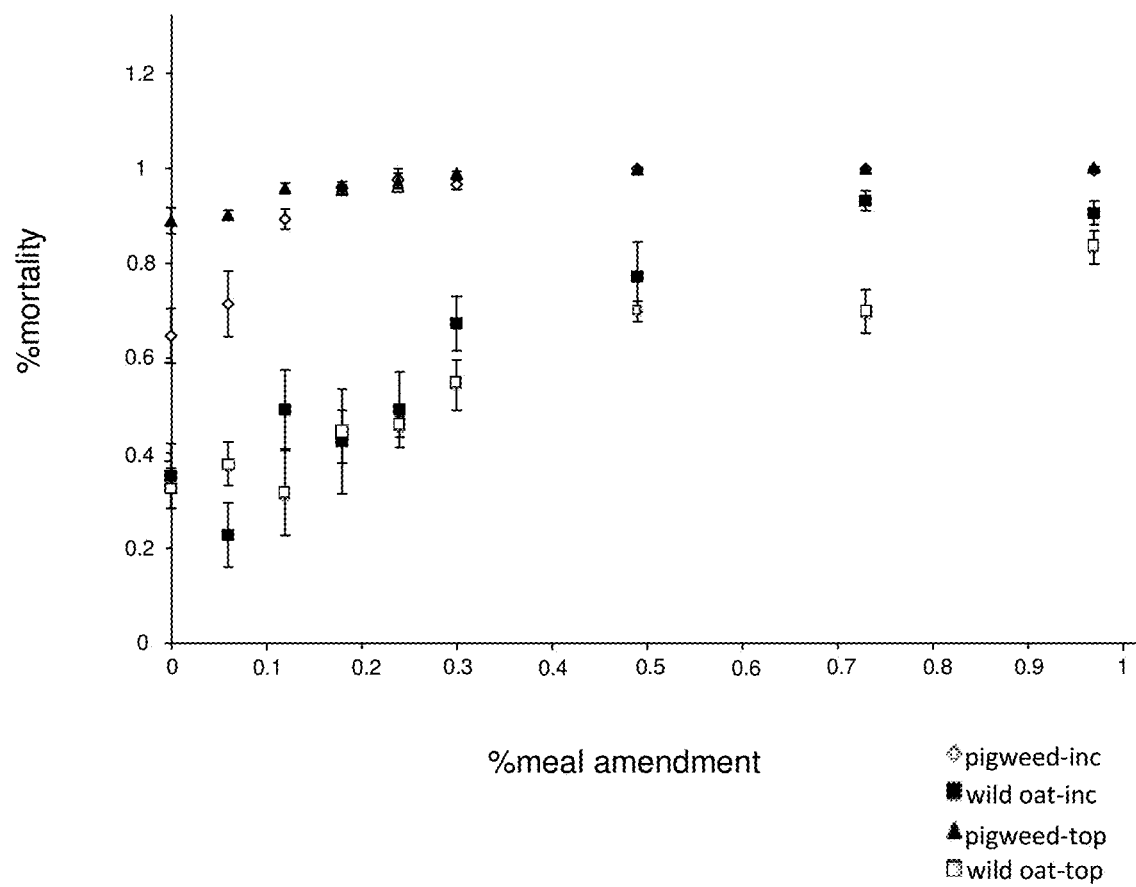
FIG. 6 is a plot of seed or seedling mortality versus percent *S. alba* meal amendment for two common weeds grown in a silt loam soil. Meal amendment is expressed on a weight basis for the ratio of the meal to the soil.

Embodiments of the present disclosure can be used to control a variety of pests, such as weeds, fungi, bacteria, yeasts, insects, such as fungus gnats, weevils, flies, and nematodes, and combinations of such pests. For example, disclosed embodiments, such as by using meal and/or extracts from various plant material, including *Sinapis alba* or *Brassica juncea*, have been used in certain embodiments to control a variety of weeds (FIGS. 4 and 6). Solely by way of example, and without limitation, a list of weeds that have been controlled using embodiments of the present invention include prickly lettuce (*Lactuca serriola*), mayweed chamomile (*Anthemis cotula*), common lambsquarters (*Chenopodium album*), wild oat (*Avena fatua*), redroot pigweed (*Amaranthus retroflexus*), liverwort and combinations thereof. It is very likely that additional weeds will be controlled, and studies are ongoing to fully elucidate the biopesticidal scope of disclosed embodiments.

Figure 7:
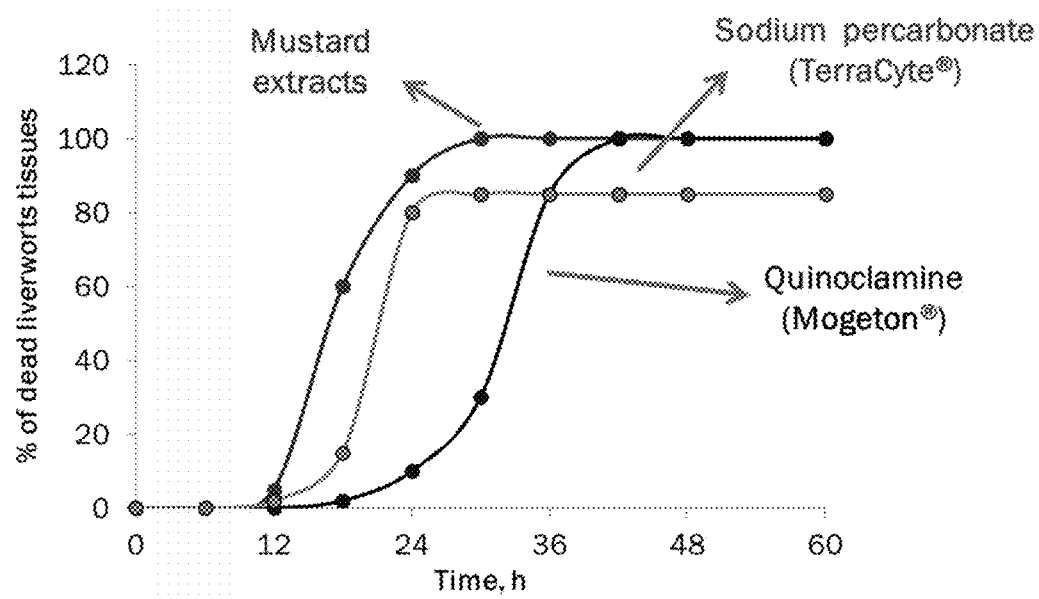
FIG. 7 is a plot of percentage of dead liverwort tissue versus time, illustrating that the efficiency of an exemplary mustard meal extract is comparable to commercial pesticides.
Figure 8:
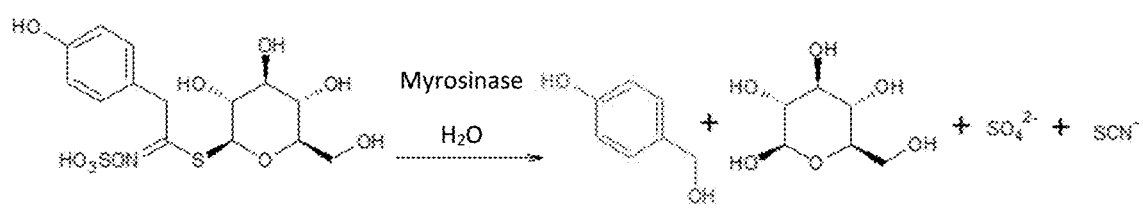
FIG. 8 is an HPLC/UV chromatogram of a 30% aqueous ethanol extract of *Sinapis alba* eluted with 0-20% methanol, illustrating the presence of 4-hydroxybenzyl alcohol.
Figure 8:
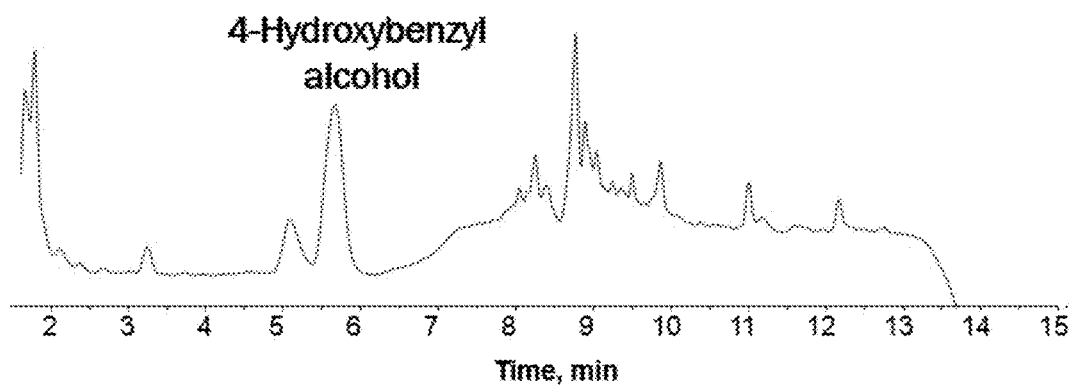
Figure 9:
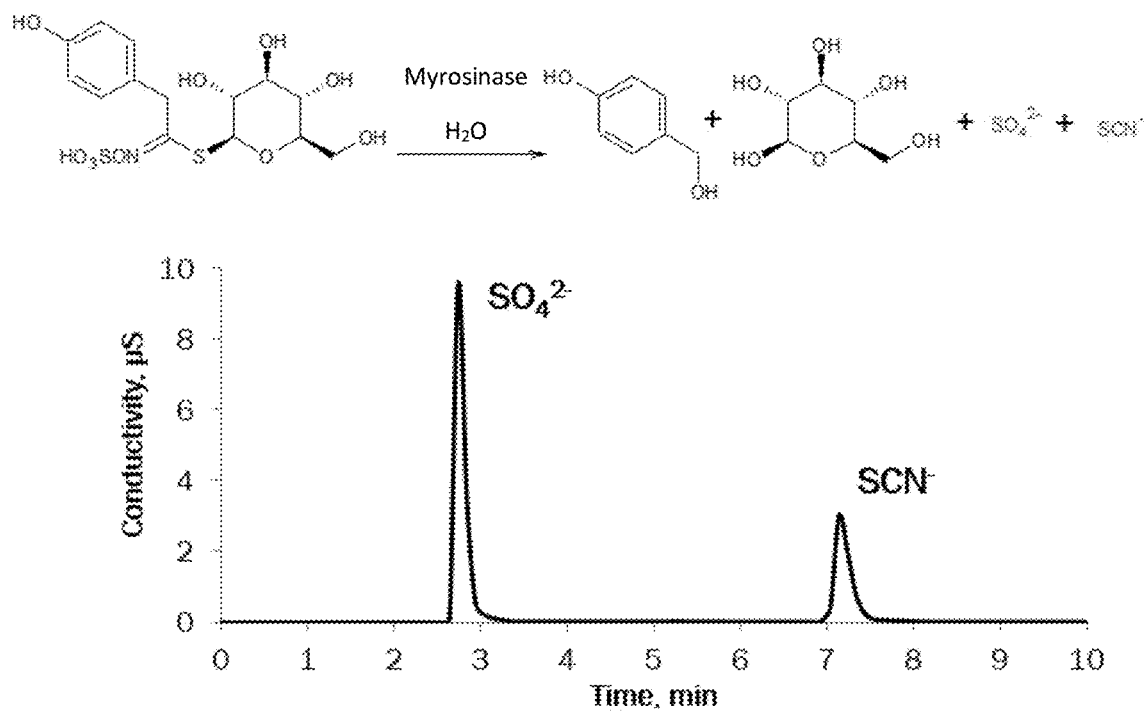
FIG. 9 is an ion chromatogram of a 30% aqueous ethanol extract of *Sinapis alba* eluted with 0-20% methanol, illustrating the presence of sulfate ions.
Figure 10:
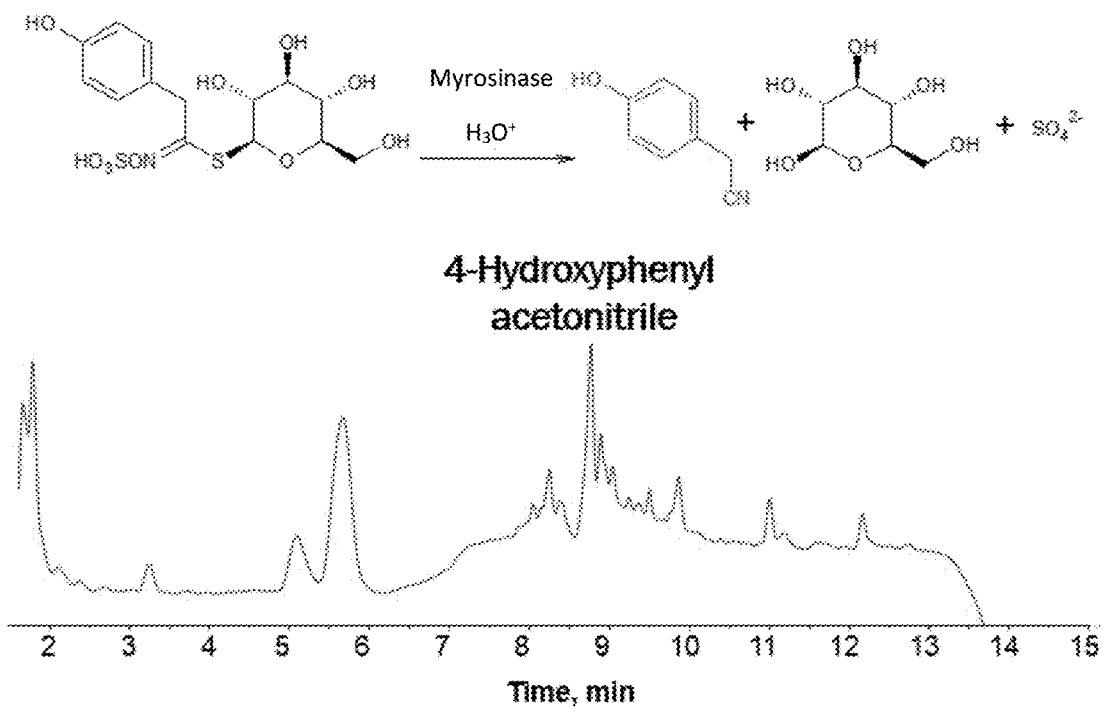
FIG. 10 is an HPLC/UV chromatogram of a 30% aqueous ethanol extract of *Sinapis alba* eluted with 0-20% methanol, illustrating the presence of 4-hydroxyphenyl acetonitrile.
Figure 11:
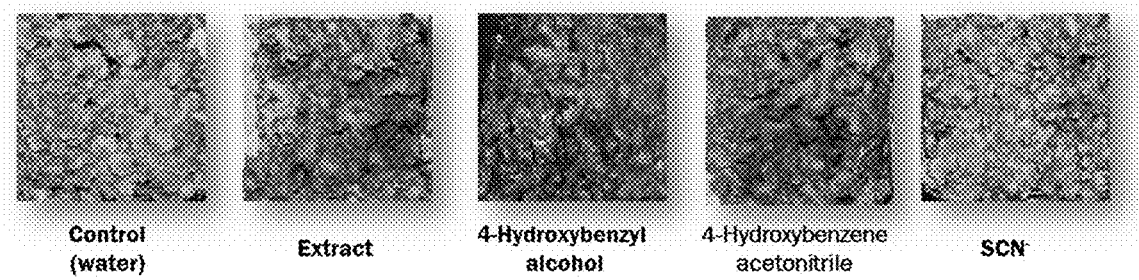
FIG. 11 provides images illustrating the results of contacting liverwort with a mustard meal extract, 4-hydroxybenzyl alcohol, 4-hydroxybenzene acetonitrile or $SCN^-$ ions, compared to water.
Figure 12:
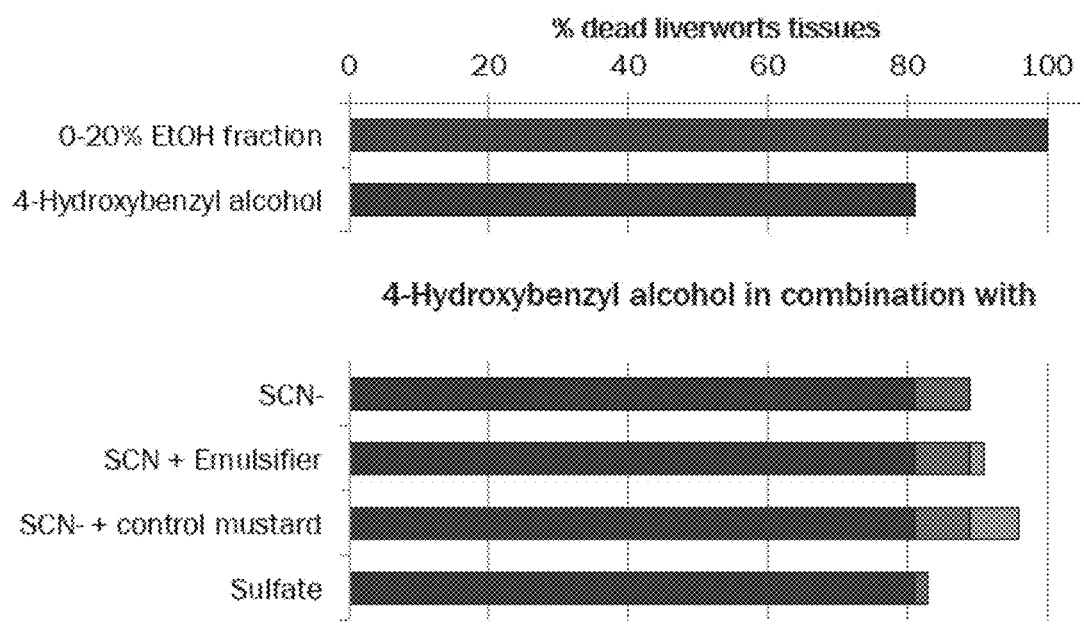
FIG. 12 is a plot of percentage of dead liverwort tissue, illustrating the effects of applying various compositions to liverwort.

For examples, the efficiency of the extract when used for liverwort control is comparable to commercial pesticides and provides a renewable and organic alternative (FIG. 7). For liverwort control, it was found that extracting *S. alba* using an extraction solvent comprising 30% ethanol and 70% water was advantageous. The liverwort was sprayed with the *S. alba* extracts until at least the upward-facing leaf surfaces were covered, but dripping from the leaves did not occur. By analyzing the extract by HPLC/TOF MS/UV chromatography, it was surprisingly found that the extract comprised 4-hydroxyphenyl acetonitrile and 4-hydroxybenzyl alcohol (FIGS. 8-10), and that there was very little, if any $SCN^-$ present. The sinalbin had been hydrolyzed to undetectable levels. However, application of either of these two compounds alone did not control the liverwort as effectively as applying the extract (FIGS. 11 and 12). Additionally, in apparent contrast to previous reports, the 4-hydroxyphenyl acetonitrile and 4-hydroxybenzyl alcohol are the primary phytotoxic compounds, rather than the $SCN^-$. $SCN^-$ appeared to be a minor contributor to the overall phytotoxicity of the extract.

X. Examples

Example 1

Hydrolysis solution composition, time, and amount of mustard meal as a source of myrosinase were varied to determine the maximum production of allyl isothiocyanate and ionic thiocyanate from sinigrin, and sinalbin, respectively.

A. Materials and Methods

1. Materials

Mustard seeds of *S. alba* (IdaGold variety) and *B. juncea* (PacifiGold) were obtained locally. Oil contents of seeds and meals were analyzed gravimetrically after extraction with hexane. A sinigrin standard and allyl isothiocyanate were purchased from Sigma-Aldrich (St. Louis, Mo., USA). Standard of sinalbin was isolated from *S. alba* in our laboratory. Acetonitrile, water, methanol, and other solvents were of HPLC or LC/MS grade. Solvents and all other chemicals (at least of analytical grade) were purchased from Sigma-Aldrich or ThermoFisher (Pittsburgh, Pa., USA).

2. Mustard Meal Crude Extract Preparation

Mustard meal was homogenized and ground to a fine powder. Seed meal was extracted with 73% (v/v) methanol at 1:20 v/v ratio using an end-to-end shaker at room temperature for 2 hours. Seed debris was separated by filtering, and filtrates were concentrated by rotary evaporation to remove most of the solvent. Concentrated extract was then freeze-dried to obtain a free flowing powder. The concentration of sinalbin in *S. alba* mustard extract was 777 µmole $g^{-1}$ extract and the concentration of sinigrin in *B. juncea* mustard extract was 555 µmole $g^{-1}$ extract.

3. Hydrolysis of Mustard Meal Crude Extract

Hydrolysis of mustard extracts was performed by adding corresponding mustard meal to mustard meal extract powder and then letting it hydrolyze in aqueous solution. Hydrolysis optimization was performed using 0.1 g of mustard meal with 0.05-0.3 of extract in 2.5 mL of aqueous solution. Hydrolysis media was modified with buffers at different pH and concentrations. Time of hydrolysis was optimized from 30 minutes to 48 hours under static conditions at room temperature.

4. Derivatization of Allyl Isothiocyanate

An aliquot (10-100 µL) of the hydrolysis mixture was diluted with methanol to 5 mL. Diluted solution (860 µL) was added to 2-mL autosample vial containing 860 µL of 100 mM potassium phosphate at pH 8.5. Then 280 µL of 35 mM 1,2-benzenedithiol/1% mercaptoethanol in methanol was added, the vial was capped and incubated for 1 hour at 65° C. After incubation, mixture was vortexed, centrifuged at 24000 rpm and analyzed by HPLC/UV.

5. HPLC/UV Analysis of Derivatized Allyl Isothiocyanate

Analysis of derivatized allyl isothiocyanate was performed using an Agilent 1200 Series HPLC system with a diode array detection (DAD) system on Agilent XDB C18 (1.8 µm, 4.6×50 mm) column (Agilent, Santa Clara, Calif., USA). Column was thermostated at 30° C. Isocratic elution was used with 90% acetonitrile in water. Flow rate was 0.6 mL/min Spectra were recorded from 190 to 400 nm with 2 nm step. Injection volume was 5 µL. The runtime was 5 minutes with a derivatized allyl isothiocyanate elution time of 1.4 minutes. Derivatized allyl isothiocyanate was quantified at extracted wavelength channel of 350-360 nm. An external calibration curve was used for quantification.

6. Ion Chromatographic Analysis

Sinigrin, sinalbin, sulfate, and ionic thiocyanate in extracts were quantified by ion chromatography (IC). IC analysis was performed using a Dionex Ion Analyzer equipped with a GP40 gradient pump, ED40 electrochemical detector, and an AS40 autosampler. Dionex 4×210 mm Ion-Pac AS16 anion exchange column was used for separation. Sodium hydroxide (100 mM) was used as the mobile phase at flow rate of 0.9 mL/min. The detector stabilizer temperature was set at 30° C. with temperature compensation of 1.7% per °C. Anion suppressor current was set to 300 mA. The injection volume was 20 µL.

7. Data Analysis

All experiments were performed at least in triplicate and are presented as means±one standard deviation. Significant differences among analyte concentrations detected by different methods of analysis were determined using one-way analysis of variance (ANOVA) with a $p<0.05$ level of significance. All analyses were performed using JMP software (version 10, SAS Institute Inc., Cary, N.C., USA).

B. Results and Discussions

1. Optimization of Hydrolysis pH and Buffering System

During sinalbin and sinigrin enzymatic hydrolysis, several hydrolysis products are released (Scheme 2). Sinigrin is hydrolyzed to equimolar amounts of allyl isothiocyanate, sulfate, glucose, and hydronium ion. Hydrolysis of sinalbin leads to equimolar amounts of 4-hydroxybenzyl alcohol, ionic thiocyanate, sulfate, glucose, and two moles of hydronium ion. The hydrolysis reaction is catalyzed by myrosinase enzyme, which is naturally present in mustard. To aid hydrolysis of mustard extracts, mustard meal was added as a source of myrosinase to the hydrolysis mixture. Mustard meal has relatively high mucilage content and can swell up to 400% in aqueous media. Thus the amount of meal added for hydrolysis of mustard extracts cannot exceed 20% by weight to allow for recovery of liquid and should not exceed 4% to allow for reasonable recovery of glucosinolates. When 0.1 g of mustard meal is added to 0.15 g of mustard extracts reconstituted in 2.5 mL of water, more than 84% of solution can be recovered after mustard meal swelling. If higher recoveries of glucosinolates are desired in the liquid phase, more diluted solutions of mustard extracts can be used.

Figure 13:
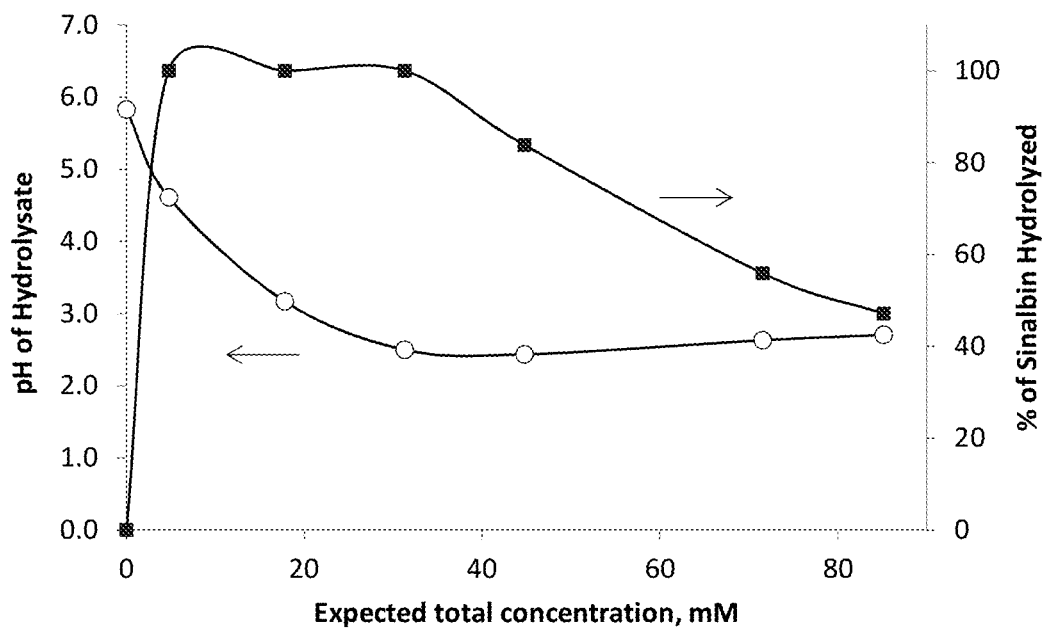
FIG. 13 is a plot of pH of hydrolysate and percentage of sinalbin hydrolyzed versus expected total concentration, illustrating the hydrolysis of *S. alba* mustard extract (0.05-0.3 g) in the presence of mustard meal (0.1 g) in 2.5 mL of water.
Figure 14:
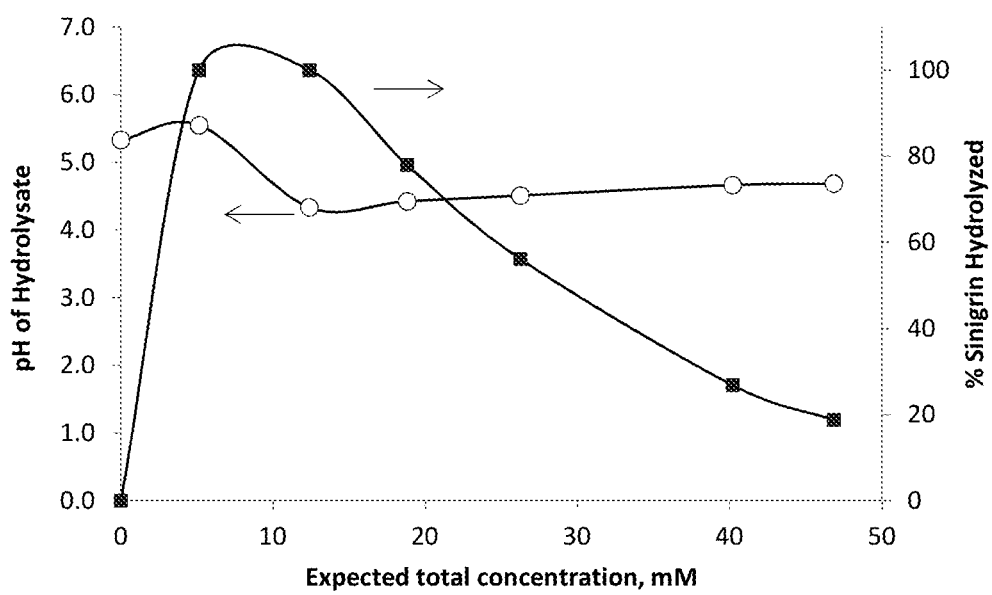
FIG. 14 is a plot of pH of hydrolysate and percentage of sinalbin hydrolyzed versus expected total concentration, illustrating the hydrolysis of *B. juncea* mustard extract (0.05-0.3 g) in the presence of mustard meal (0.1 g) in 2.5 mL of water.

For hydrolysis of endogenous glucosinolates the buffering capacity of mustard meal is sufficient to maintain pH even when endogenous glucosinolates are hydrolyzed in the presence of water and hydronium ion is released. However, unlike endogenous concentrations in mustard meal, concentration of glucosinolates in mustard extracts are significantly higher. The excess of glucosinolates relative to the meal leads to the change in pH that exceeds buffering capacity of the meal. Myrosinase has maximum of activity at pH of 5-7, while its activity is almost negligible at low pH. Indeed, when the amount of mustard extract was increased relative to the meal, the incomplete hydrolysis was observed with the increase of the total glucosinolate amount (FIGS. 13 and 14). Despite the increase of sinalbin extract added to the reaction mixture, the maximum concentration of SCN⁻ produced was leveled out at 24 mM, which is about five times higher concentration that could be produced from the original mustard meal. For sinigrin, a similar trend was observed. The maximum concentration of allyl isothiacyanate produced was 14 mM even when up to 42 mM of sinigrin was added to the meal in the form of a mustard extract.

The incomplete hydrolysis of glucosinolates in mustard extracts is due to the decrease of reaction mixture pH (FIGS. 13 and 14). Upon hydrolysis of endogenous sinalbin, pH typically decreases by one unit from 5.8 to 4.6, at which myrosinase activity is still adequate. However, when mustard extracts are added to the meal, more than three-fold increase of the sinalbin concentrations resulted in pH decrease to one more unit pH. Sinalbin concentrations four times higher than the endogenous concentrations resulted in the pH of 2.5 and the myrosinase inactivation. Similarly, pH of sinigrin hydrolysis mixture is decrease to 4.6.

Figure 15:
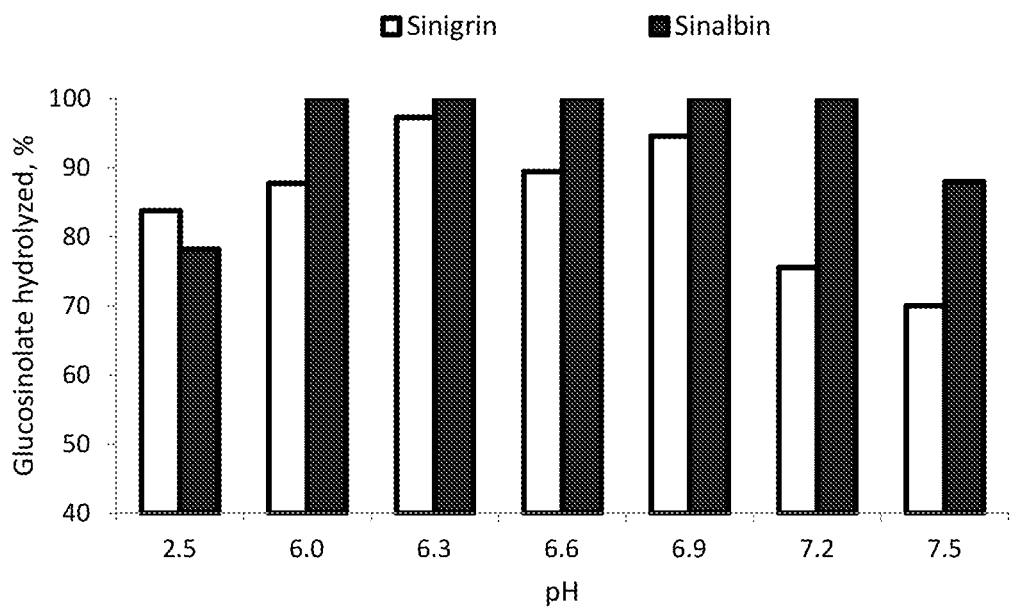
FIG. 15 is a plot of glucosinolate hydrolyzed versus pH, illustrating the hydrolysis of *S. alba* and *B. juncea* mustard extracts (0.15 g) in the presence of mustard meal (0.1 g) in 2.5 mL of 200 mM phosphate buffer.

To prevent inactivation of myrosinase by increased acidity, a series of phosphate buffers in the pH range from 6.0 to 7.5 was used instead of water for glucosinolate hydrolysis (FIG. 15). When 200 mM phosphate buffer was used, complete hydrolysis of sinigrin and sinalbin was observed in pH range from 6.0 to 7.2, while some of glucosinolates were still unhydrolyzed when pH was increased to 7.5. The minimum concentration of phosphate buffer required for maintaining pH was investigated and accounted for 1.5-2 times of the expected concentration of glucosinolates in the extracts.

Other buffering agents (carbonate and bicarbonate) at the same concentration were equally efficient in maintaining hydrolysis mixture pH at 6.5 and providing complete hydrolysis of sinalbin and sinigrin. The use of carbonate for pH adjustment allows for the development of the glucosinolate extract pesticide which can be certified as organic and may make the final product less expensive.

2. Optimization of Hydrolysis Media Composition

To achieve quantitative conversion of intact glucosinolates to their biologically active products, hydrolysis media composition was further optimized. In the presence of buffer with mustard meal as a myrosinase source, sinigrin and sinalbin are completely hydrolyzed, however only 90% of corresponding biologically active hydrolysis products are produced.

Figure 16:
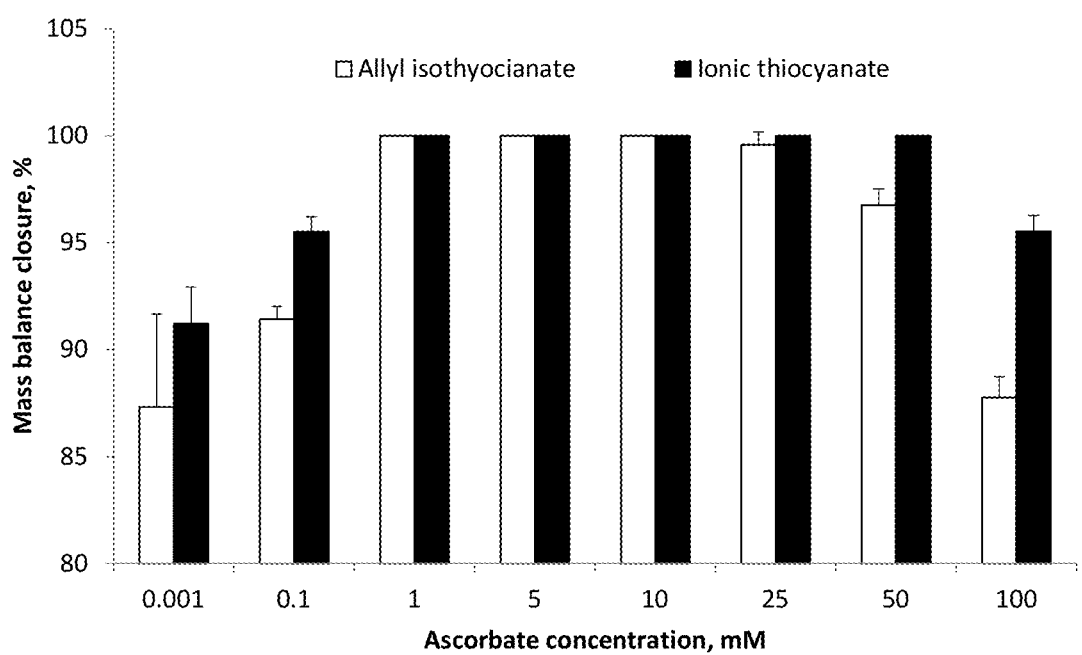
FIG. 16 is a plot of mass balance closure versus ascorbate concentration, illustrating the effect of ascorbate addition on the production of allyl isothiocyanate and ionic thiocyanate from *B. juncea* and *S. alba* mustard powder.

When ascorbic acid was added to the reaction mixture, almost quantitative release of allyl isothiocyanate and ionic thiocyanate was observed. Ascorbic acid acts as a co-factor for myrosinase and it is naturally present in mustard meal. However, with high glucosinolate concentrations present in mustard extracts, additional amounts of ascorbic acid are needed. Particularly, when 0.1-50 mM of ascorbic acid was added to the hydrolysis solution, all of sinalbin was converted to SCN⁻, and all sinigrin was converted to allyl isothiocyanate (FIG. 16). With respect to FIG. 16, the mass balance closure represents the percentage of glucosinolate converted to the biologically active allyl isothiocyanate and ionic thiocyanate on a molar basis.

While it may be advantageous to maintain pH and ascorbic acid content in the hydrolysis mixture, it is also useful to carefully select mustard meal that will be used a source of myrosinase to assure high myrosinase activity. Mustard meal is typically obtained by cold pressing mustard seed for oil. During the pressing process, some of the myrosinase can be deactivated due to the local heat in the press. In fact, it has been estimated that myrosinase activity in some processed meals may be as little as less than 0.5% of the activity found in the unprocessed seed. Cold pressing and defatting with hexane to remove mustard oil does not affect the concentrations of glucosinolates, but affect the activity of myrosinase. Growth, harvest, and storage conditions can also affect the activity of the myrosinase. As a result, the amount of glucosinolates hydrolyzed is lower.

3. Optimization of Hydrolysis Time

The glucosinolate-myrosinase system is designed in such a way that the increase of water content in the plant coupled with the seed tissue rupture lead to the immediate hydrolysis reaction. Without being bound to a particular theory, the release of hydrolysis products may be a defense mechanism of mustard plants. When mustard extract is hydrolyzed under static conditions, it can take a substantial period of time for complete hydrolysis of glucosinolates, due to the significant higher concentrations of glucosinolates.

Figure 17:
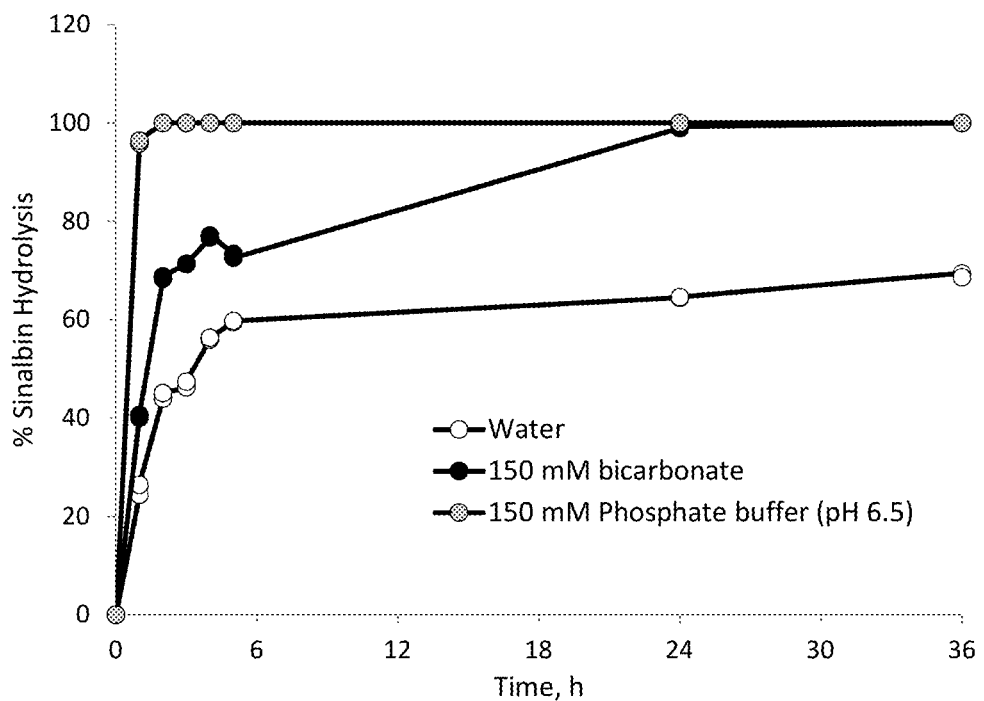
FIG. 17 is a plot of sinalbin hydrolysis versus time, illustrating the hydrolysis of *S. alba* and *B. juncea* mustard extracts (0.15 g) in the presence of mustard meal (0.1 g) in 2.5 mL of 150 mM phosphate buffer or 150 mM potassium bicarbonate.

Using phosphate and bicarbonate as buffering agent at final concentration of 150 mM, complete hydrolysis of sinalbin and sinigrin was observed in 24 hours (FIG. 17). Phosphate buffer allows for faster hydrolysis and all glucosinolates can be hydrolyzed under static condition in just 12 hours. Original pH of phosphate buffer is 6.5 and it coincides with the optimum pH for myrosinase. When potassium bicarbonate was used for maintaining pH, original pH was 9.5 and then reduces to 6.5 over the time as hydronium ions were released from glucosinolates. Since myrosinase activity at pH 9.5 is lower than that at pH 6.5, initial hydrolysis reaction rates were slower as compared to the phosphate buffered systems. When no buffering agent was used, hydrolysis rates were generally slower and incomplete hydrolysis was observed even after reaction time of 36 hours.

Faster release of biologically active compounds can shorten bioherbicide preparation time. However, slower release of biologically active compounds may be beneficial for better control of pests. For example, when sinigrin is hydrolyzed, fast release of allyl isothiocyanate may result in undesired loss of volatile allyl isothiocyanate. At the same time, if allyl isothiocyanate is released slowly over the time, allyl isothiocyanate has better changes to interact with potential pest and ultimately lead to the more efficient pest control.

Example 2

This example provides detail concerning seed meal preparation, determination of glucosinolate concentrations in defatted meal, release of 4-hydroxybenzyl glucosinolate from meal, and ionic thiocyanate production from 4-OH benzyl isothiocyanate.

All analyses and experiments were performed with meal remaining after seed from the *S. alba* cultivar IdaGold was cold pressed to remove approximately 90% of the oil. The remaining oil was removed by performing three extractions with petroleum ether that involved shaking 500 grams of the meal with 500 milliliters of petroleum ether and filtering through a Büchner funnel. The final filtration cake was washed with 250 milliliters of petroleum ether, allowed to air dry, and homogenized in a blender.

Sinalbin Content of the Meal.

The glucosinolate concentration of the defatted meal was determined using a method similar to that of the International Organization of Standardization. Defatted seed meal was weighed (200 mg) into 15-mL extraction tubes to which 500 mg of 3-mm glass beads, 10 milliliters of 70% methanol/water solution, and 100 µL of internal standard (4-methoxybenzyl glucosinolate, obtained from meadowfoam (*Limnanthes alba*) seed meal) were added. The detector response factor for 4-methoxybenzyl glucosinolate was determined by comparison with known concentrations of 2-propenyl glucosinolate having an assumed response factor of 1.0. Extraction tubes were shaken for 2 hours on a reciprocal shaker and centrifuged for 5 min at 1073 g to precipitate the seed meal. The extract solution was transferred to columns containing 250 mg of DEAE anion exchanger and allowed to drain freely. The columns were washed twice with 1 milliliter of deionized water and finally with 1 milliliter of 0.1 M ammonium acetate buffer (pH 4.0). To the columns was then added 100 µL of a 1 mg/L sulfatase enzyme (Sigma-Aldrich, St. Louis, Mo.) solution and 100 µL of 0.1 M ammonium acetate buffer (pH 4.0). The columns were covered to prevent evaporation and allowed to stand with the enzyme for 12 hours, after which time the samples were eluted into HPLC autosampler vials with two consecutive 750-µL volumes of deionized water.

A Waters 2695 HPLC separation module coupled with a Waters 996 photodiode array detector (PDA) and Thermabeam Mass Detector (TMD) was used for glucosinolate analysis. For quantitative purposes all desulfoglucosinolates detected by PDA were measured at a wavelength of 229 nanometers. Separation was performed on a 250×2.00 mm, 5µ, 125 Å Aqua C18 column (Phenomenex, Torrance, Calif.). The flow rate was 200 µL/min, with a methanol gradient starting at 0.5% and increasing to 50%. Glucosinolates were identified using a combination of expected retention behavior (time, sequence) and mass spectra.

4-Hydroxybenzyl Isothiocyanate Release from *S. alba* Seed Meal.

Ten grams of the defatted meal were weighed into polypropylene centrifuge tubes to which was added 40 mL of deionized water. In one set of triplicate samples we added 10 milliliters of ethyl acetate as the extractant and 1 µL of decane (Sigma-Aldrich, St. Louis, Mo.) as the internal standard immediately after mixing the meal with deionized water. The mixtures were shaken, maintained at 22±2° C., and samples removed periodically during a 96-hour incubation period. In a second set of triplicate samples, the addition of 10 milliliters of ethyl acetate and 1 µL of decane were delayed until 30 minutes prior to each respective sampling time. At each sampling time the mixture was centrifuged for 10 minutes at 1677 g and 250 µL of the supernatant was withdrawn for analysis. GC-MS analysis was performed using an HP 5890A gas chromatograph equipped with a 30 m×0.32 mm i.d., 0.25 µm film HP-5MS capillary column (Agilent Technologies) coupled to an HP 5972 mass detector. Ethyl acetate extracts were manually injected into a split/splitless port (250° C., 20 s split) and temperature of the GC oven was programmed from 65° C. (isocratic 3 minutes) to 270° C. (isocratic 5 minutes) at a rate of 15° C./minute. Average linear flow rate of helium at 250° C. was 35 centimeters/minute. Data (total ion current) were corrected using decane as the internal standard and quantified using benzyl isothiocyanate as an external standard.

Extraction efficiencies for 2-propenyl, butyl, benzyl, and t-octyl isothiocyanates were determined by combining 10 µL of each in duplicate 40-milliliters deionized water samples. The samples were treated in the same manner as described above including both the immediate and delayed addition of ethyl acetate and decane. The amount of each analyte extracted using continuous or periodic extraction was determined using GC-MS as described for *S. alba* seed meal.

Stability of 4-Hydroxybenzyl Isothiocyanate in Buffered Media.

Partially purified 4-hydroxybenzyl isothiocyanate was prepared by suspending 500 grams of *S. alba* seed meal in 2 liters of deionized water and extracting the mixture with 500 milliliters of ethyl acetate for 24 hours. The ethyl acetate extract was separated by decanting the top organic layer after centrifugation, dried with 100 g of anhydrous sodium sulfate overnight, and concentrated under vacuum at laboratory temperature. The crude 4-hydroxybenzyl isothiocyanate extract was further purified by preparative column chromatography on silica gel (500 grams). Elution was achieved in a stepwise fashion using six 100-milliliter aliquots of eluent composed of pentane and methylene chloride at ratios of 100:0, 80:20, 60:40, 40:60, 20:80, and 0:100. Content of 4-hydroxybenzyl isothiocyanate within the fractions was verified by GC-MS using instrumentation and conditions as described previously. Fractions containing 4-hydroxybenzyl isothiocyanate were combined and concentrated under vacuum at laboratory temperature producing a yellowish, viscous fluid displaying only 4-hydroxybenzyl isothiocyanate and pentane/methylene chloride solvent peaks in the GC chromatogram. No further concentration of 4-hydroxybenzyl isothiocyanate was achieved using vacuum distillation because of its instability.

The pH stability of 4-hydroxybenzyl isothiocyanate was analyzed by incubating 25 µL of partially purified extract dissolved in 25 milliliters of eight different buffers with pH values ranging from 3.0 to 6.5 (FIG. 2). 0.1 M buffers were used, and were prepared by mixing 0.2 M sodium citrate and citric acid solutions in pre-calculated ratios ranging from 4 milliliters sodium citrate and 46 milliliters citric acid to 41 milliliters sodium citrate and 9 milliliters citric acid in a total volume of 100 milliliters. Actual pH values of the buffers of 3.03, 3.52, 4.02, 4.49, 5.00, 5.46, 5.91, and 6.52 were verified using an Orion model 420A pH meter (Orion Research, Boston). At specific times during the incubation a 1-milliliter sample was withdrawn from the buffered reaction solution with a syringe and injected into a Waters Integrity HPLC system (2695 separation module, 996 PDA, and TMD) equipped with a 150×2 mm i.d., 5 µm Aqua C-18 column (Phenomenex). The instrument was operated at a constant flow rate of 200 µL/min with a gradient from 5 to 35% of methanol during each 30-minute run. Half-lives for 4 hydroxybenzyl isothiocyanate were estimated from straight lines obtained by plotting the natural logarithm of the normalized concentration versus time (FIG. 2). This experiment was repeated twice with two different meal extracts acquired by the same procedures from the same seed material. Half-lives from only one of the experiments are reported since the results for both experiments were similar.

Release of SCN$^-$ from S. alba Seed Meal.

Figure 18:
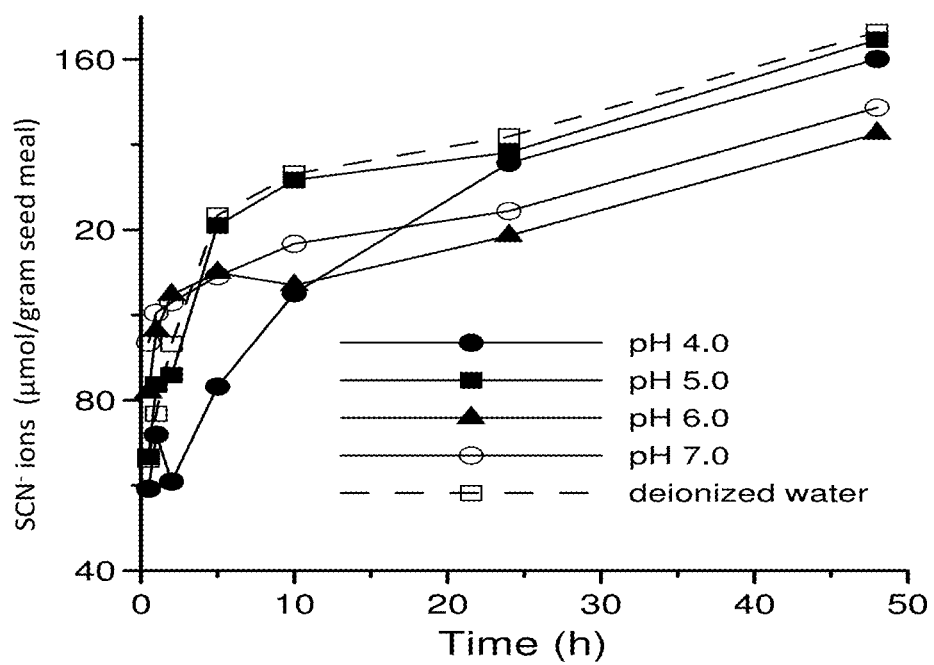
FIG. 18 illustrates the production of ionic thiocyanate from *S. alba* seed meal incubated in deionized water and aqueous solutions buffered at pH values ranging from 4.0 to 7.0.

Ten grams of defatted S. alba meal were weighed into a 250-mL polyethylene bottle to which was added 200 milliliters of deionized water or a citrate buffer solution (pH of 4.0, 5.0, 6.0, or 7.0) prepared as described previously. The samples were placed on a reciprocating shaker for 48 hours during which time 5.0-milliliter aliquots were removed periodically to determine the time course of SCN$^-$ release. Each 5-milliliter aliquot was placed in a 50-milliliter centrifuge tube and 40.0 milliliters of a methanol:deionized water (2:1, v:v) solution containing 1% acetic acid was added. The tubes were shaken vigorously for 15 minutes, centrifuged for 5 minutes at 1073 g, and 5 milliliters of the supernatant filtered through a 25-mm, 0.2-µm GD/X membrane (Whatman) into a beaker. One milliliter of the filtered sample was then transferred to an HPLC autosampler vial to which was added 0.50 milliliter of a 0.01 M Fe$^{3+}$ solution and 100 µL of a 0.1 M HCl solution. The vials were capped, shaken, and immediately analyzed using a Waters Integrity HPLC system equipped only with a 5-µm, 10×2 mm i.d. Aqua C-18 pre-column (Phenomenex). A 50-µL sample was injected and isocratically eluted using a 10% methanol solution pumped at a flow rate of 0.5 milliliter/minute. Absolute concentrations of SCN$^-$ in the unknown samples were determined following the same procedure as described above, except that 10.0 grams of S. alba meal from which the glucosinolates had been removed with repeated methanol extraction was substituted for the unaltered meal. Amounts of a KSCN stock solution containing 10 to 100 µmol of SCN$^-$ were added to the meal/buffer mixtures prior to the initial shaking and a separate standard curve prepared for each buffer pH (FIG. 18).

Glucosinolates in S. alba Meal.

As expected, sinalbin was the major glucosinolate in S. alba meal, constituting approximately 93% of total glucosinolate content. The measured concentration of sinalbin in defatted meal was 152±5.2 µmol/gram (mean value±variance of five replicates). The meal also included (2R)-2-hydroxybut-3-enyl glucosinolate (3.6 µmol/g) and five unidentified glucosinolate peaks with a total estimated glucosinolate concentration of approximately 6.4 µmol/g. Concentrations of indolyl glucosinolates that could potentially produce SCN$^-$ as a result of hydrolytic instability of their respective isothiocyanates represented a total of only about 1 µmol/g of defatted seed meal. Simplicity of the glucosinolate profile in S. alba meal thus facilitates our ability to determine a likely precursor for glucosinolate hydrolysis products that might be identified. Most important is the fact that low concentrations of indolyl glucosinolates eliminate the possibility that these compounds can serve as precursors of significant amounts SCN$^-$ that might be measured in hydrolyzed extracts.

4-Hydroxybenzyl Isothiocyanate Release from S. alba Seed Meal.

Figure 19:
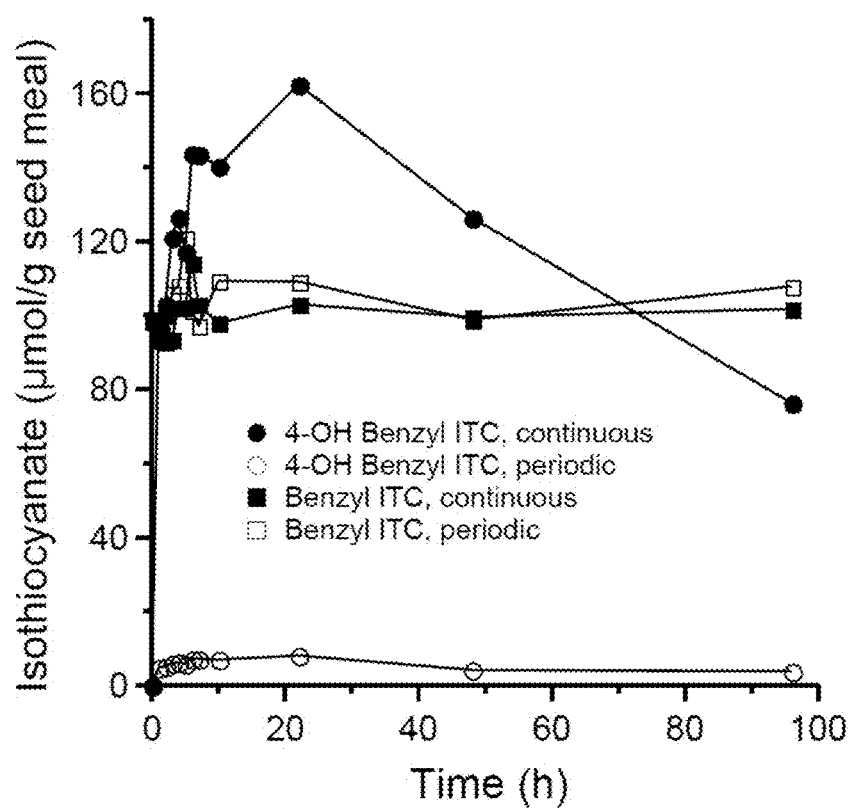
FIG. 19 is a plot showing continuous and periodic extraction into ethyl acetate of 4-hydroxybenzyl isothiocyanate resulting from hydrolysis of 4-OH benzyl glucosinolate contained in *S. alba* seed meal as compared to similar extractions of benzyl isothiocyanate from aqueous solution. 4-Hydroxybenzyl isothiocyanate incubations contained no seed meal, but are expressed on a weight basis for comparison purposes only.

A dramatic difference was observed between the relatively high yield of 4-hydroxybenzyl isothiocyanate obtained by continuously extracting into ethyl acetate as compared to periodic measurements made by adding ethyl acetate 30 minutes prior to each respective sampling time (FIG. 19). Maximum 4-hydroxybenzyl isothiocyanate extracted during the continuous procedure was 162 µmol/gram seed meal at 24 hours, whereas less than 10 µmol/gram was extracted at any one time in the periodic analyses. In contrast, when continuous and periodic extractions were performed with benzyl isothiocyanate, comparable concentrations of the compound were measured in the ethyl acetate extracts irrespective of the procedure. 2-Propenyl, butyl, and t-octyl isothiocyanates showed extraction yields similar to that of benzyl isothiocyanate ranging from at least 98% for all isothiocyanates in the continuous extraction to a low of 83% for 2-propenyl isothiocyanate in the periodic extraction.

These results establish that 4-hydroxybenzyl isothiocyanate is unstable in aqueous media, and that isolation and purification require the use of non-reactive solvents.

Stability of 4-Hydroxybenzyl Isothiocyanate in Buffered Aqueous Solutions.

Partially purified and concentrated seed meal extracts containing 4-hydroxybenzyl isothiocyanate were dissolved in buffers ranging from pH 3.0 to 6.5. The half-life of 4-hydroxybenzyl isothiocyanate at pH 6.5 was the shortest at 6 minutes, increasing to 16, 49, 100, 195, 270, 312, and 321 minutes with decreasing pH values of 6.0, 5.5, 5.0, 4.5, 4.0, 3.5, and 3.0, respectively (FIG. 2). Hydrolytic instability of 4-hydroxybenzyl isothiocyanate, especially at higher pH values, explains its low extractability in unbuffered extracts of seed meal that had a pH of 5.3 and a sampling time of 48 hours. Appreciable hydrolysis occurs at pH values as low as 3.0 and in a soil environment buffered at pH values typically between 5 and 7, significant amounts of SCN⁻ production are expected in a relatively short time period.

Ionic Thiocyanate Release from *S. alba* Seed Meal.

*S. alba* seed meal was incubated with deionized water and buffer solutions ranging from pH 4.0 to 7.0 to quantify SCN⁻ production resulting from 4-hydroxybenzyl glucosinolate hydrolysis in the presence of a full component of meal constituents (FIG. 18). SCN⁻ production occurred most slowly at pH 4.0, but final concentrations determined at 48 hours varied from a low at pH 6.0 of 143 and a high in deionized water of 166 μmol/gram seed meal. The amount of SCN⁻ expected based on 4-hydroxybenzyl glucosinolate concentration in the meal and the assumption of its complete stoichiometric conversion to SCN⁻ is approximately 152 μmol/g seed meal, thus indicating near complete conversion in 48 hours at all pH values.

Results obtained with seed meal incubations confirm conclusions reached using 4-OH benzyl glucosinolate extracts, clearly indicating that 4-hydroxybenzyl isothiocyanate is rapidly hydrolyzed to SCN⁻ at pH values expected in most soils. In contrast, data from previous investigations conducted with purified sinalbin and myrosinase indicate that decreased pH values promote the formation of 4-hydroxybenzyl cyanide at the expense of 4-hydroxybenzyl isothiocyanate, thereby decreasing subsequent formation of SCN⁻ by approximately 50% at pH 3.0 as compared to pH 7.0. The presence of additional meal components moderates the influence of pH on the production of 4-hydroxybenzyl cyanide, thus preserving SCN⁻ formation. Application of *S. alba* seed meal to soil with the addition of sufficient water to promote glucosinolate hydrolysis is expected to produce an amount of SCN⁻ stoichiometrically equivalent to the amount of 4-hydroxybenzyl glucosinolate within the meal.

SCN⁻ production in soils amended with *S. alba* seed meal has significant consequences with respect to phytotoxicity and the use of meal as a bioherbicide. The herbicidal activity of SCN⁻ is well known and commercial formulations containing NH₄SCN have been marketed. Amendment rates necessary for weed control have been determined by a number of investigators for $NH_4^+$, $K^+$, and $Na^+$ salts with complete removal of all vegetative cover reportedly occurring for a period of 4 months when SCN⁻ was applied at rates of 270 to 680 kg/ha. Higher rates of 1,366 kg SCN⁻/ha were necessary for complete plant kill for 4 months, but a large percentage of the weeds were removed with only 137 kilograms SCN⁻/ha. Application rates were that might alter wheat germination, and it was found that 342 kilograms SCN⁻/ha caused inhibition, but that the effect was no longer observed at 69 days post application. Solutions of SCN⁻ sprayed directly on vegetative growth showed that cotton defoliation was possible using only 8.6 kilograms SCN⁻/ha.

Amounts of SCN⁻ contributed from *S. alba* seed meal used here, assuming complete stoichiometric conversion, would amount to 8.8, 17.7, and 35.3 kg SCN⁻/ha for amendment rates of 1000, 2000, and 4000 kilograms meal/ha, respectively. Although glucosinolate concentrations in the *S. alba* meal used were not reported, weed control effects have been observed with application rates of 1000 to 2000 kilograms/ha. Phytoxicity also has been observed towards weed and crop species when meal was amended to greenhouse or field soils at rates from 1000 to 4000 kilograms meal/ha. SCN⁻ rates provided in *S. alba* meal, although not as high as those used previously in phytotoxicity studies with soluble salts, provide SCN⁻ in amounts of potential value in weed control.

In addition to weed control benefits afforded by SCN⁻ produced as a result of glucosinolate hydrolysis, the meals contain between 5 and 6% N that when mineralized represents an important nutrient source to crop plants. Organic agriculture may thus benefit from the use of *S. alba* meal as a soil amendment both through weed control and as a nutrient source. Potential environmental effects appear minimal given that biological degradation of SCN⁻ has been observed in soils and *S. alba* is typically grown as a condiment mustard for human consumption.

Glucosinolate concentrations in Brassicaceae seed meals as may be determined according to the method of this example are shown in Table 1 below.

TABLE 1

Glucosinolate concentrations in Brassicaceae seed meals.

| Glucosinolate R-group | B. napus "Athena" | B. napus "Sunrise" | S. alba "Ida Gold" | B. juncea "Pacific Gold" |
|---|---|---|---|---|
| | μmol g⁻¹ of sample | | | |
| (2R)-2-hydroxy-3-butenyl | 1.5 | 1.3 | 3.4 | 0.5 |
| 2-propenyl | | | | 123.8 |
| (2S)-2-hydroxy-3-butenyl) | 0.4 | | | |
| 2-hydroxy-4-butenyl) | 0.2 | | 1.8 | |
| (2R)-2-hydroxy-4-pentenyl | | | | 0.5 |
| 4-hydroxy-benzyl | | | 148.1 | |
| Unknown | | | 9.1 | |
| 3-butenyl | 2.8 | 2.7 | | |
| 4-hydroxy-3-indolylmethyl (0.28) | 11.3 | 10.9 | | 0.74 |
| unknown | | | 2.6 | |
| unknown | | | 0.74 | |
| 4-pentenyl | 1.3 | 1.4 | | |
| 3-indolylmethyl | 0.9 | 0.8 | | |
| 4-methylthiobutyl | 1.7 | | | |
| N-methoxy-3-indolylmethyl | | 0.1 | 0.01 | 0.6 |
| unknown | | | | 1.33 |
| TOTAL | 20.1 | 17.2 | 165.75 | 126.14 |

Highest glucosinolate concentrations were measured in *S. alba* IdaGold meal with 4-OH benzyl showing as the dominant glucosinolate. The *B. juncea* variety Pacific Gold had the next highest glucosinolate concentration, with propenyl glucosinolate dominating the total. It has been shown that both 4-OH benzyl and propenyl glucosinolates produce ITC as an end product of hydrolysis at typical soil pH values.

More recent evidence indicates that this assumption is not true for 4-OH benzyl glucosinolate. ITC production is significant since this compound is considered to be the most toxic of all glucosinolate hydrolysis products and thus most important in pest control. Recent results with weed seed bioassays prompted a reevaluation of this assumption and further prompted considering the inhibitory properties of other compounds, such as ionic thiocyanate.

The remaining *B. napus* varieties, Athena and Sunrise, were included as they routinely are used as an amendment in bioassay control experiments, and only low glucosinolate concentrations were present.

Example 3

This example concerns the effects of processing and storing disclosed compositions. In an effort to facilitate dispersal of meal in future applications a pelletization trial was conducted for several seed meals. Equipment used for pelleting grains into animal feed was used to form pellets comprising small amounts of both Athena and IdaGold seed meal. This process normally includes a step of exposing the stock material to high-temperature steam, which aids in producing a stable pellet; however, this step was excluded to retain intact glucosinolates within the meal. The end product extruded was a relatively stable pellet having a diameter of 0.4 cm and a length ranging from 1-3 cm. With this shape, these pellets would theoretically allow the material to be applied with existing equipment and without using special modifications.

Once sample pellets were obtained, they were reground to form a fine powder and the glucosinolate profile was compared to the stock meal used to make pellets. Additionally the total glucosinolate content of older stocks of *B. napus* Dwarf Essex, *S. alba* IdaGold, and *B. juncea* Pacific Gold meal from previous harvests in 2001 were compared to the same meals produced during 2002. This comparison was conducted to determine if significant amounts of glucosinolates were lost during storage for up to a year. With the exception of Athena, neither the process of converting meal flakes into pellets, nor storing the meal for approximately a year had much effect on the total glucosinolate content (FIG. 3). The comparison of old and new stocks of Dwarf Essex, IdaGold, and Pacific Gold meal revealed little difference in composition and heterogeneity. It is likely that variability could be attributed to different environmental conditions experienced between growing seasons of the two harvests. Timing of moisture, growing degree days, and level of damage from insects each could have affected the final glucosinolate profile of the harvested seed. The process of producing pellets from the meal had no detrimental effect on the glucosinolate content, and the intense physical homogenization which occurs prior to the extrusion of the pellets appeared to decrease the final variability of total glucosinolates within the IdaGold meal.

Example 4

This example concerns isothiocyanate release from cold pressed meals. Glucosinolate hydrolysis is necessary for ITC release. Only a portion of the glucosinolate is actually converted to ITC. Initial efforts were thus directed towards quantifying the proportion of ITC produced relative to the original glucosinolate concentration. The effectiveness of modifying meal products to enhance ITC release can thus be determined by monitoring for an increase in release efficiency.

Ten grams of meal were mixed with 40 milliliters of deionized water and 10 milliliters of ethyl acetate containing 1 µl decane as an internal standard. The mixture was shaken and samples were removed periodically during a time period of 96 hours. Analysis of the samples was performed used GC-MS. An HP 5890A gas chromatograph coupled with an HP 5972 series A Mass Detector was used, along with a DB-5 capillary column (30 in×320 pm, 0.25 pm film). Ethyl acetate extracts were manually injected into a split/splitless port (250 liters, 20 seconds split), and the temperature of the GC oven was programmed from 65° C. (iso 3 minutes) to 270° C. (iso 5 minutes) with a rate 15° C./minute. Average linear flow rate of helium at 250° C. was 35 cm/minute. Quantification of data (total ion current) was performed using decane as internal standard in all samples and calibration with benzyl isothiocyanate. Isothiocyanate release efficiency in the form of a percentage was calculated using the following equation.

Release efficiency=(Isothiocyanate/Glucosinolate)× 100

Stoichiometry for glucosinolate hydrolysis shows that each mole of glucosinolate is expected to release 1 mole of ITC. Release efficiencies lower than 100% will occur when ITC amounts are less than glucosinolate amounts within the respective meal.

Figure 20:
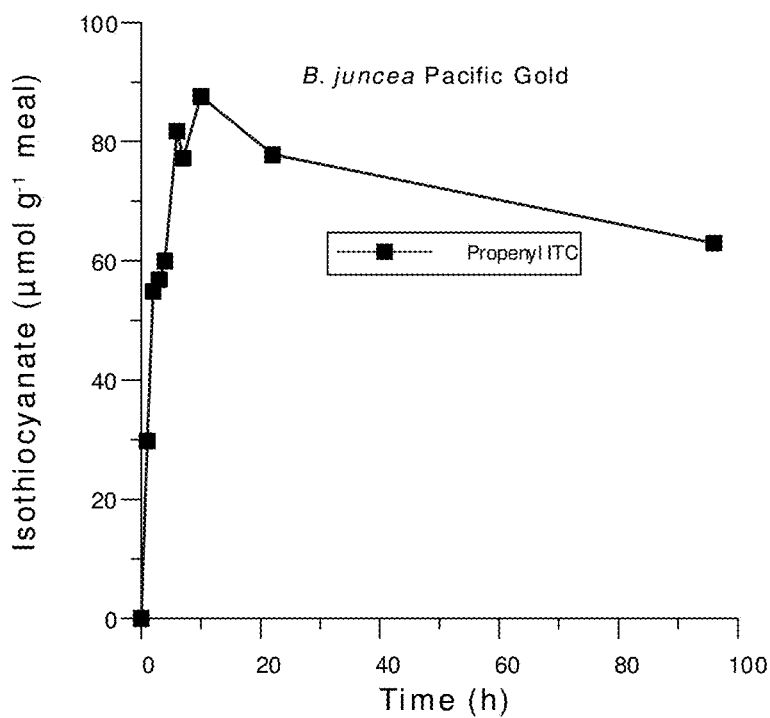
FIG. 20 is a graph of isothiocyanate formation from *B. juncea* Pacific Gold meal product versus time (hours).
Figure 21:
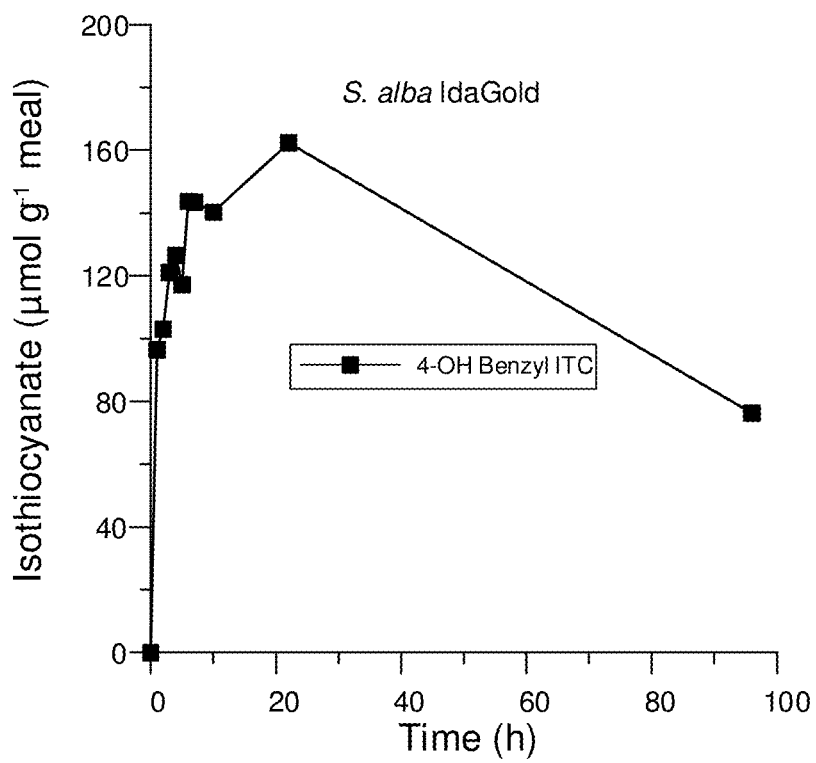
FIG. 21 is a graph of isothiocyanate formation from *S. alba* IdaGold meal product versus time (hours).
Figure 22:
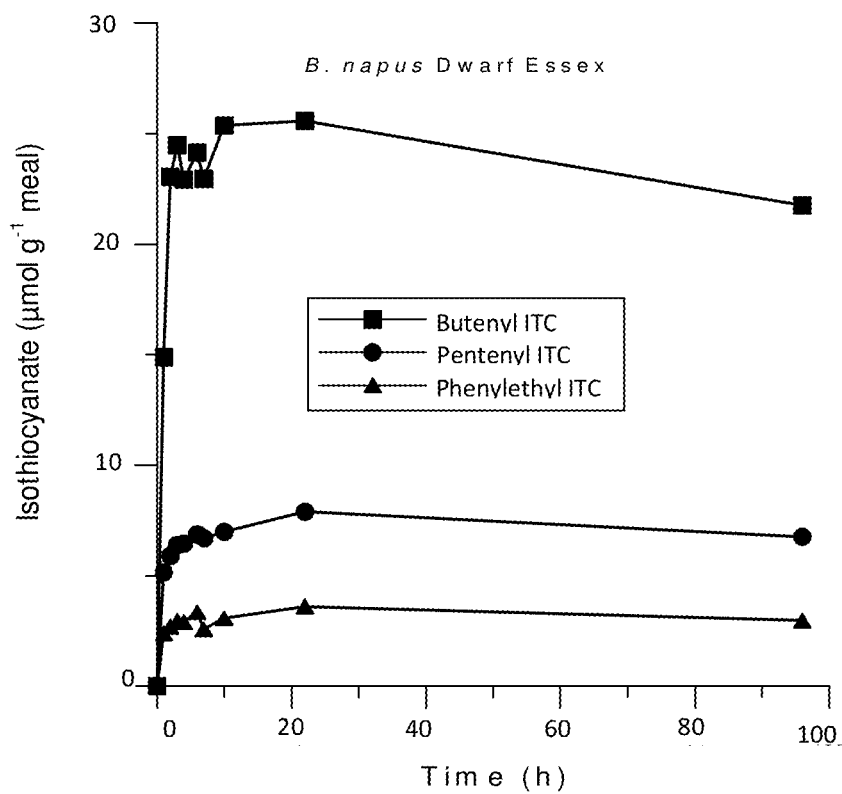
FIG. 22 is a graph of isothiocyanate formation from *B. napus* Dwarf Essex meal product versus time (hours).

FIGS. 20-22 provide time release curves. FIG. 20 provides a time release curve for propenyl ITC from *B. juncea* Pacific Gold meal. Maximum ITC release of 88 µmol/gram seed meal occurred at 10 hours. This amount of ITC is equivalent to a release efficiency of 80%. Thus 80% of the glucosinolate potentially available was actually measured as ITC. FIGS. 21 and 22 provide the ITC release curves for *S. alba* IdaGold and *B. napus* Dwarf Essex. The ITC release efficiency from *S. alba* IdaGold is 29% (FIG. 21) and that for *B. napus* Dwarf Essex is 65% (FIG. 22). Increased release efficiencies translate into more effective pest control.

Release efficiency data indicate that little benefit exists for attempting to enhance propenyl release from *B. juncea* meal. Greater benefit may be realized by increasing ITC release from *S. alba* meal since the release efficiency was only 29%. However, the meal already contains high 4-OH benzyl concentrations that may reduce the need for such enhancement. In addition, for *S. alba* it is quite possible that release efficiency is not the only contributing factor to the measured low ITC concentrations. Measured concentrations are a function of opposing ongoing processes that include both ITC production and ITC dissipation. For *S. alba*, dissipation may occur at a relatively high rate, thus decreasing the mass of ITC accumulating in the medium. This indeed is what was observed to occur. 4-OH Benzyl isothiocyanate is unstable and thus is degraded to form $SCN^-$.

Example 5

No effect of *S. alba* meal on soil insects and nematodes was observed. The lack of a biological response with *S. alba* meal was puzzling given the fact that this meal contained the highest concentration of glucosinolate, that being predominantly 4-OH benzyl. It was assumed that ITC formed from 4-OH benzyl glucosinolate is stable unless subjected to strong alkali, at which time it is hydrolyzed and $SCN^-$ is formed. Release efficiency data indicate that such thinking may not accurately reflect 4-OH benzyl ITC behavior.

The pH stability of 4-OH benzyl ITC was assayed by incubating it in 5 buffer solutions (sodium acetate/acetic acid from pH range 3 to 5 and monosodium phosphate/phosphatic acid for pH above 5) with pH ranging from 3.0 to 7.0. At specific times during the incubation a sample from the incubated solution was withdrawn with a syringe and injected into an HPLC-PDA (Waters Integrity system, separation module 2695, photodiode array detector 996, column Phenomenex Aqua C-18, 5 µm, 150×2 mm, with a constant flow rate of 200 µl/minute gradient from 5 to 35% of methanol in 30 minutes). The amount of 4-OH benzyl ITC was determined using calibration with benzyl ITC.

TABLE 2

Stability of 4-OH benzyl isothiocyanate at different pH levels

| pH | Half Life (Minutes) |
|---|---|
| 3 | 216 |
| 4 | 126 |
| 5 | 90 |

TABLE 2-continued

Stability of 4-OH benzyl isothiocyanate at different pH levels

| pH | Half Life (Minutes) |
|---|---|
| 6 | 6 |
| 7 | 4.8 |

4-OH benzyl isothiocyanate was not stable even at pH values of 3.0. The half-life decreases with an increase in pH from 3.6 hours at pH 3.0 to less than 5 minutes at pH 7.0. Thus in a soil environment 4-OH benzyl ITC will be produced from S. alba meal but because it is unstable, will hydrolyze rapidly to produce ionic thiocyanate as shown below.

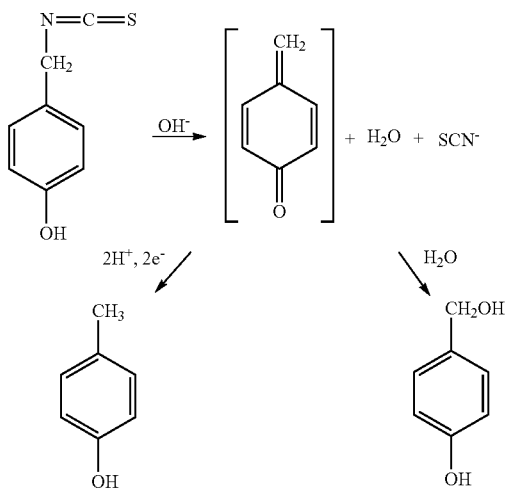

The lack of a negative effect on insects, nematodes, and fungi is caused by the rapid hydrolysis of 4-OH benzyl ITC. This instability may also contribute to the low release efficiencies that were measured. However, the fact that S. alba meal is an effective herbicide indicates that one of the hydrolysis products is responsible. Literature indicates that $SCN^-$ is indeed phytotoxic and thus of likely importance in weed inhibition.

Example 6

This example concerns determining soil pH effective for maintaining bioactivity of disclosed plant material, processed plant material, composition comprising plant material, or composition comprising processed plant material. Soil is sampled up to depth 35 cm using stainless steel soil probe of diameter 20 mm Three replicate soil samples were taken from individual plots, and similar depths were merged into one soil sample. Soil cores for depth 0-5, 5-10, 10-15, and 15-25 centimeters were individually transferred into marked plastic storage bags for temporary storage.

Soil samples were homogenized by hand directly in storage bags, and transferred into pre-weighed and marked 250-mL PE bottles. After addition of 200 milliliters of extracting solution, (5 mmol/L solution of calcium chloride in DI water) and 1.00 milliliter of internal standard (100 mmol/L solution of potassium bromide in DI water) PE bottles were tightly closed, and shaken on reciprocating shaker for 60 minutes. PE bottles with shaken samples were left on a laboratory bench for another hour, to allow soil particles to sediment. It is possible to accelerate sedimentation using centrifugation. Supernatant from above was drawn into a 10-milliliter syringe, and immediately filtered into a marked autosampler vial using an in-line disposable filter (PVDF Filter media, 25 mm diameter, 0.45 µm pore size, Whatman, N.J., USA).

Approximately 10-gram soil samples from a particular depth profile were merged across the field and put into pre-weighed metal cans, and reweighed. The samples were then dried in an oven set at a temperature of about 120° C. until the samples had a constant weight.

Soil extracts were analyzed using ion chromatograph (Dionex, Sunnyvale, Calif., USA) in the following configurations and conditions: GP40 gradient pumps, ED40 electrochemical detector, and AS40 automated sampler, 250 µL sampling loop, gradient elution from 5 to 80 mmol/L potassium hydroxide in 15 minutes, column IonPacAS16, 4×250 mm, software PeakNet v 5.01.

A standard solution of 100 mmol/L of potassium thiocyanate in DI water was precisely diluted to obtain calibration solutions in a range from 1 µMol/L to 10 mmol/L. One milliliter of calibration solution was pipetted into 200 milliliters of extracting solution (5 mmol/L calcium chloride in DI water). Samples for all concentration levels were created in triplicates. Calibration solutions were analyzed exactly the same way as the field soil samples.

Figure 23:
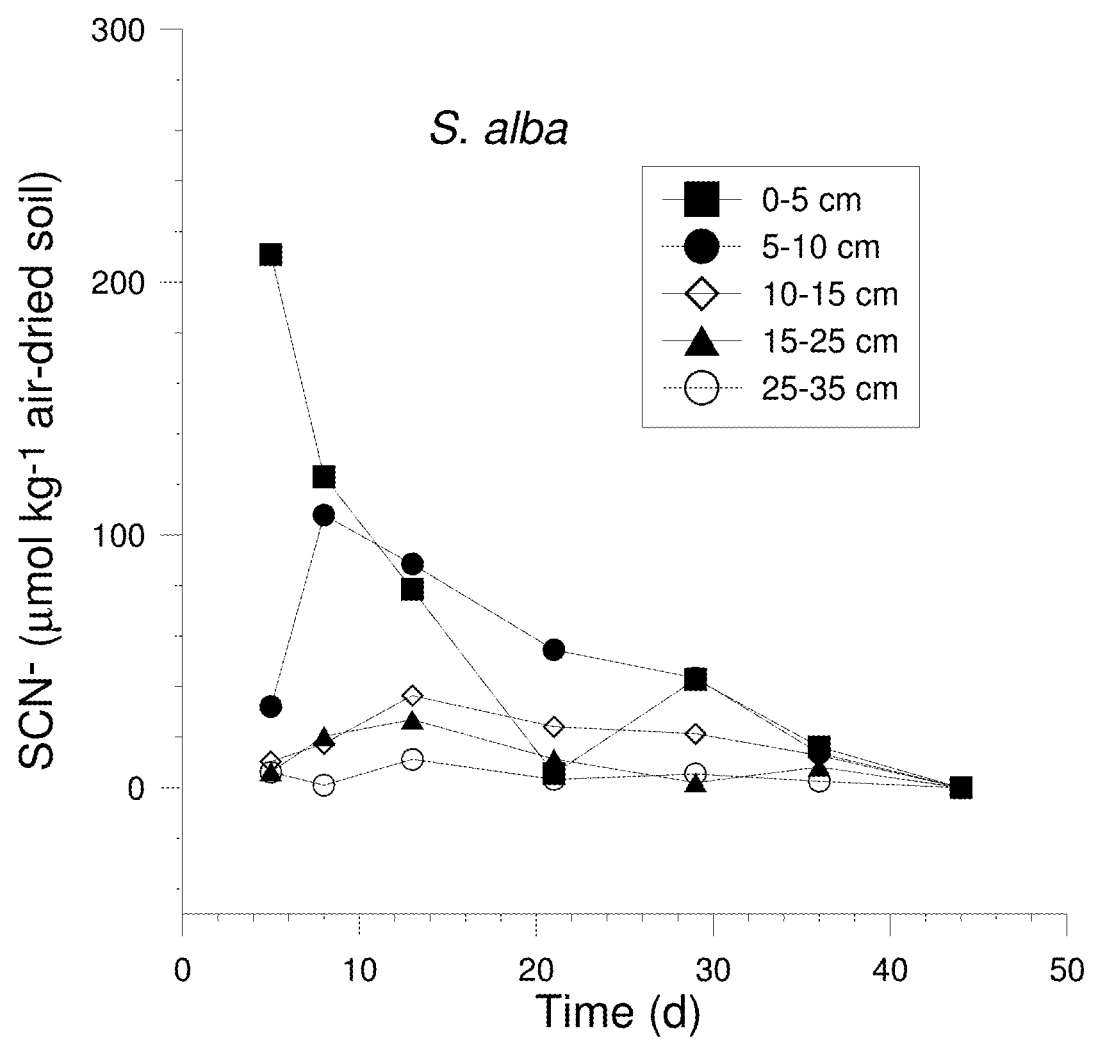
FIG. 23 is a graph of $SCN^-$ concentration in extracts obtained from field soils at various depths sampled at the noted times (days) after *Sinapis alba* meal amendment.
Figure 24:
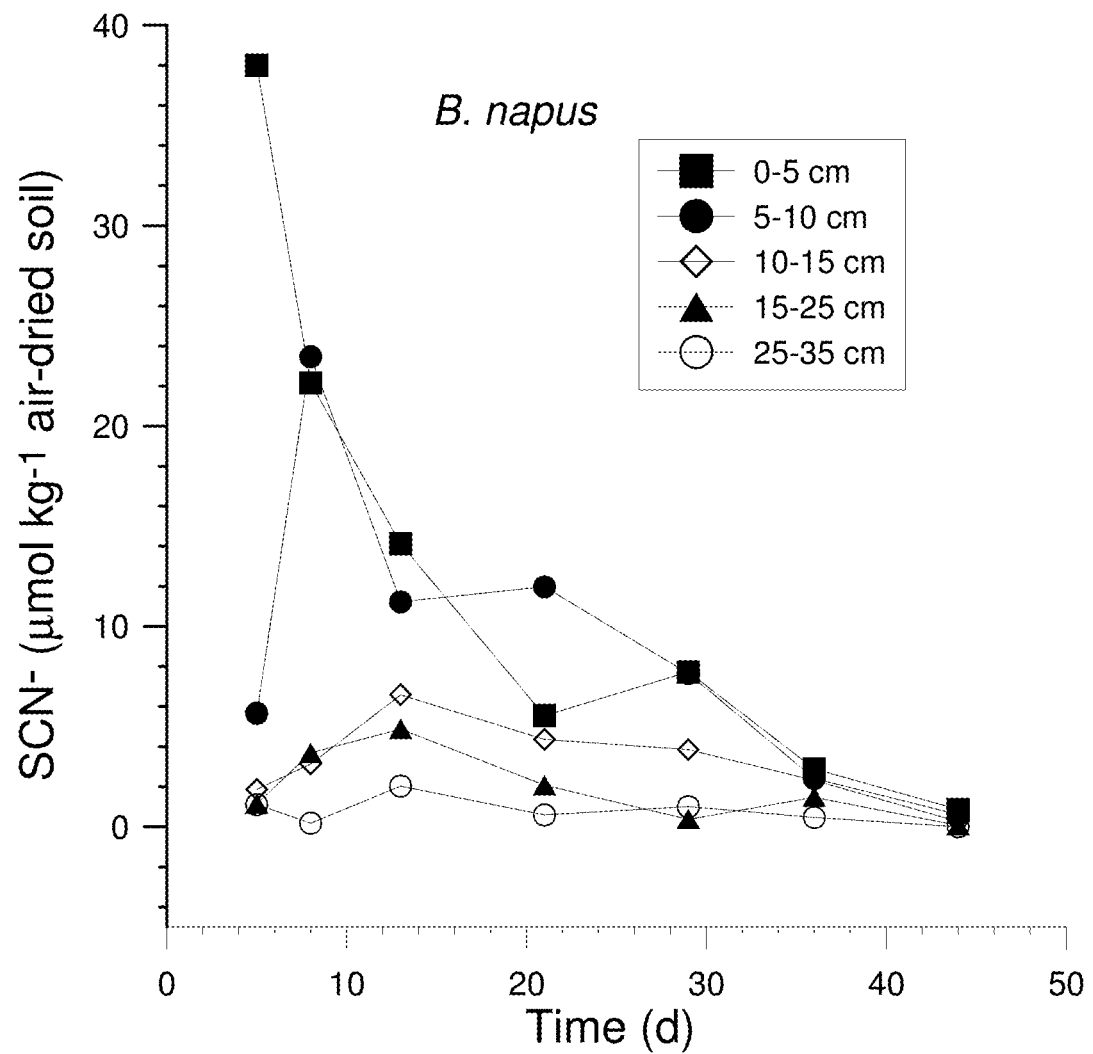
FIG. 24 is a graph of $SCN^-$ concentration in soil extracts obtained from soils at various depths sampled at the noted times (days) after *Brassica napus* meal amendment to field soil.
Figure 25:
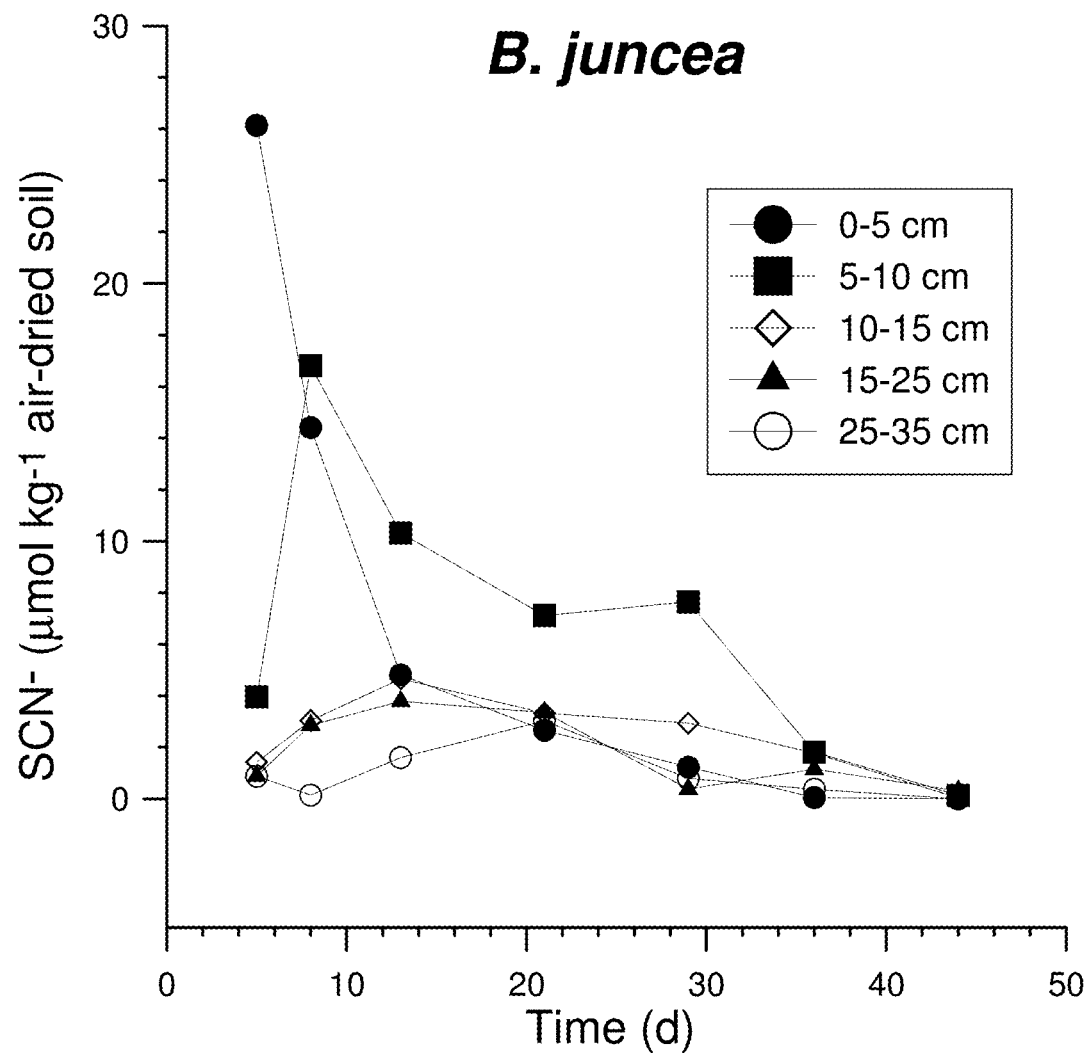
FIG. 25 is a graph of $SCN^-$ concentration in soil extracts obtained from soils at various depths sampled at the noted times (days) after *Brassica juncea* meal amendment to field soil.

Data files were integrated automatically using PeakNet software supplied with instrument. All chromatograms were checked for missed or undetected peaks of thiocyanate anion, and when necessary, thiocyanate anion peaks were integrated manually. The same integration parameters were applied for field soil samples and for calibration solutions. A calibration curve was obtained by linear regression of thiocyanate peak areas versus thiocyanate concentrations. Concentrations of thiocyanate anion in soil samples were estimated using slope and constant value of linear regression of calibration data. Results, shown in FIG. 23 (S. alba), FIG. 24 (B. napus) and FIG. 25 (B. juncea) are expressed per one kilogram of dry soil, using known moisture content of the soil samples.

Example 7

Sinapis alba meal was expected to have the greatest effect on fungus gnats. However, initial trials showed little response. The lack of a response prompted a reevaluation of the chemistry, eventually leading to the determination that S. alba is ineffective against insects because the isothiocyanate produced is unstable.

Fungus Gnat Control with Cold Pressed Meal:

Four different meals, B. juncea 'Pacific Gold', S. alba 'IdaGold', B. napus 'Dwarf Essex', and B. napus 'Athena', were used in a series of bioassay experiments to determine pesticidal behavior against fungus gnats. The effectiveness of volatiles in closed containers was determined in which the meal was physically separated from the test organism. Only volatiles from the wetted meal were allowed to contact the bioassay organism. The effect of meal incorporation and top dressing were also assessed in separate experiments. Specific details of each trial are shown below in Tables 3-12. These tables show data collected in preliminary experiments designed to determine the effects of meal volatiles on fungus gnat adults. B. juncea 'Pacific Gold' showed complete control, whereas S. alba 'IdaGold' was ineffective. The high glucosinolate B. napus 'Dwarf Essex' showed partial control and as expected, low glucosinolate B. napus 'Athena' had no effect on adult fungus gnat survival. Preliminary results with larvae were similar, except that Dwarf Essex showed no effect.

Meal incorporation into the potting medium showed similar trends with respect to fungus gnat toxicity. *B. juncea* meal showed complete fungus gnat control at a rate of 3%, whereas *S. alba* showed little impact at a rate of 6% (w:w). Nematodes were completely eliminated by *B. juncea*, but not *S. alba* meal.

Gnat larvae were killed by isothiocyanate volatiles from *B. juncea*, but not from *B. napus* or *S. alba*. This is in line with many of the other bioassays. *Sinapis alba* is not toxic to larvae. Volatiles produced from *Brassica napus* 'Dwarf Essex' or 'Athena' were not toxic. Either the volatiles were not produced or they were produced at levels that were below a threshold level of toxicity.

Fungus gnat survival was determined by counting the number of adults that emerged from the respective treatments. High glucosinolate *B. napus* and *S. alba* meals showed some control at rates of 10%, but never equivalent to that of *B. juncea*. Nematode survival in the potting mix also was determined, and only *B. juncea* completely eliminated nematodes.

With respect to fungus gnat larval survival for trials with larger numbers of replicates, the most effective treatment is *B. juncea* meal amendment at 3 and 6%. Decreased fungal gnat survival with amendment of *B. napus* Dwarf Essex and *S. alba* meals was determined, but even 6% amendment did not result in acceptable fungus gnat control.

With reference to the effect of meal top-dressing and minimal soil incorporation on the survival of fungus gnat larvae, significant decreases in emerging numbers of adult fungus gnats when *B. juncea* meal was either top-dressed or incorporated into the top 6-7 mm of potting mix. There was no difference between any of the 3% and 6% treatments.

TABLE 3

Fungus gnat adult volatile experiment[1] (n = 1)

| Treatment[2] | number adults alive: | | |
|---|---|---|---|
| | after 90 minutes | after 17 hrs | after 24 hrs |
| Peat moss (control) | 10 | 8 | 8 |
| *B. juncea* (Pacific Gold) | 0 | 0 | 0 |
| *S. alba* (IdaGold) | 10 | 8 | 5 |

[1]Bioassay chamber consisted of a 50-dram snap-cap plastic vial, with 10 adults place in 9-dram snap cap vial with organdy top and drop of apple sauce for sustenance. Treatment material was placed at the bottom of the 50-dram vial.
[2]Treatments: 1) 0.75 g peat moss + 4 ml water; 2) 0.75 g *Brassica juncea* meal + 4 ml water; and 3) 0.75 g *Sinapis alba* meal + 4 ml water.

TABLE 4

Fungus gnat adult volatile experiment[1] (n = 2)

| Treatment[2] | Mean number adults alive after: | | | | | |
|---|---|---|---|---|---|---|
| | 30 min. | 60 min. | 90 min. | 6 hrs | 18 hrs | 24 hrs |
| *B napus* (Athena) | 10 | 10 | 10 | 10 | 9.5 | 7.5 |
| *B. napus* (Dwarf Essex) | 10 | 10 | 10 | 9.5 | 7.0 | 3.0 |

[1]Bioassay chamber consisted of a 50-dram snap-cap plastic vial, with 10 adults place in 9-dram snap cap vial with organdy top and drop of apple sauce for sustenance. Treatment material was placed at the bottom of the 2-dram glass vial.
[2]Treatments: 1) 0.75 g *Brassica napus* (Athena) + 4 ml water; 2) 0.75 g *Brassica napus* (S37) meal + 4 ml water.

TABLE 5

Fungus gnat larval volatile experiment[1] (n- = 2)

| Treatment[2] | Mean number larvae alive: | | |
|---|---|---|---|
| | after 90 minutes | after 20 hrs | after 43 hrs |
| Peat moss (control) | 10 | 10 | 10 |
| *B. juncea* (Pacific Gold) | 10 | 0 | 0 |
| *S. alba* (IdaGold) | 10 | 10 | 10 |

[1]Bioassay chamber consisted of a 50-dram snap-cap plastic vial, with 10 last-instar larvae placed on small piece of agar sprinkled with small amount of sifted alfalfa meal in open 4-dram glass vial. Treatment material placed in a separate open 4-dram glass vial.
[2]Treatments: 1) 0.75 g peat moss + 4 ml water; 2) 0.75 g *Brassica juncea* meal + 4 ml water; and 3) 0.75 g *Sinapis alba* meal + 4 ml water.

TABLE 6

Fungus gnat larval volatile experiment[1] (n- = 2)

| Treatment[2] | Mean number larvae alive after: | | |
|---|---|---|---|
| | 90 min. | 17 hrs | 24 hrs |
| *B. napus* (Athena) | 10 | 9.5 | 9.5 |
| *B. napus* (Dwarf Essex) | 10 | 9.5 | 9.5 |

[1]Bioassay chamber consisted of a 50-dram snap-cap plastic vial, with 10 last-instar larvae placed on small piece of agar sprinkled with small amount of sifted alfalfa meal in open 4-dram glass vial. Treatment material placed in a separate open 4-dram glass vial.
[2]Treatments: 1) 0.75 g *Brassica napus* (Athena) + 4 ml water; 2) 0.75 g *Brassica napus* (S37) meal + 4 ml water.

TABLE 7

Incorporation of meal into soil experiment (n = 3)

| Treatment | Mean number fungus gnat adults emerged per pot | nematodes present (day 13) |
|---|---|---|
| *B. napus* 3% (control) | 15.7 | yes |
| *B. juncea* 1% | 11.3 | yes |
| *B. juncea* 3% | 0.0 | no |
| *B. juncea* 6% | 0.0 | no |

Treatments consisted of approximately 18 grams dry weight of a Sunshine mix no. 2/composted bark mixture (7:3); mixed with 1, 2, or 3% meal (*Brassica napus* 'Athena' or *Brassica juncea* 'Pacific Gold'); plus approximately 1.6 grams dry pinto beans (soaked for 24 hours in water) for larval food; plus the appropriated amount of water to have a moist mixture. This mixture was placed in plant pots (6 cm×6 cm×8 cm ht). Twenty fungus gnat larvae were added to the mixture in each of the pots. Numbers of adults emerging were recorded daily.

TABLE 8

Incorporation of meal into soil experiment (n = 3)

| Treatment | Mean number fungus gnat adults emerged per pot | nematodes present (day 14) |
|---|---|---|
| *B. napus* 3% (control) | 15.0 | yes |
| *S. alba* 1% | 15.0 | yes |
| *S. alba* 3% | 14.7 | yes |
| *S. alba* 6% | 12.7 | yes |

Treatments consisted of approximately 18 grams dry weight of a Sunshine mix no. 2/composted bark mixture (7:3); mixed with 1, 2, or 3% meal (*Brassica napus* 'Athena' or *Sinapis alba* 'IdaGold'); plus approximately 1.6 grams dry pinto beans (soaked for 24 hours in water) for larval food; plus the appropriated amount of water to have a moist mixture. This mixture was placed in plant pots (6 cm×6 cm×8 cm ht). Twenty fungus gnat larvae were added to the mixture in each of the pots. Numbers of adults emerging were recorded daily.

TABLE 9

Gnat Larval Volatile Experiment[1] (n = 10).

| Treatment | Mean number larvae per container alive (% alive) after: | | |
|---|---|---|---|
| | 2 hrs | 4 hrs | 24 hrs[2] |
| Brassica napus (Athena) | 20.0 (100%) | 20.0 (100%) | 19.9 (99.5%) |
| Brassica napus (Dwarf Essex) | 20.0 (100%) | 20.0 (100%) | 19.6 (98%) |
| Brassica juncea (Pacific Gold) | 16.6 (83%) | 0.0 (0%) | 0.0 (0%) |
| Sinapis alba (IdaGold) (batch 1) | 20.0 (100%) | 20.0 (100%) | 19.4 (97%) |

[1]Bioassay chamber consisted of a 50-dram snap-cap plastic vial, with 20 last-instar larvae placed on small piece of agar sprinkled with small amount of sifted alfalfa meal in open 4-dram glass vial. Treatment material (1.0 g meal) placed in a separate open 4-dram glass vial. Five milliliters of water added to meal at start of experiment. Experiment set up on Feb. 21, 2002.
[2]Dead larvae in B. napus and S. alba treatments appear to have drowned, except possibly one larva in Dwarf Essex treatment.

TABLE 10

Incorporation of meal into soil experiment (n = 5).

| Treatment | Mean number fungus gnat adults emerged per pot | % survival (larvae to adult) | nematodes present (day 14) |
|---|---|---|---|
| B. napus (Athena) 20% | 13.6 ± 0.9 a | 68 | yes |
| B. napus (D. Essex) 20% | 10.8 ± 2.0 ab | 54 | yes |
| B. napus (D. Essex) 10% | 8.2 ± 1.2 bc | 41 | yes |
| B. napus (D. Essex) 30% | 7.4 ± 0.9 cd | 37 | yes |
| S. alba 10% (batch 2) | 5.0 ± 1.4 d | 25 | yes |
| S. alba 20% (batch 2) | 2.0 ± 0.4 e | 10 | yes |
| S. alba 30% (batch 2) | 1.8 ± 0.0 e | 9 | yes |
| B. juncea 20% | 0.0 ± 0.0 e | 0 | no |
| B. juncea 10% | 0.0 ± 0.0 e | 0 | no |
| B. juncea 30% | 0.0 ± 0.0 e | 0 | no |

Treatments consisted of approximately 18 grams dry weight of a Sunshine mix no. 2/composted bark mixture (7:3); mixed with 10, 20, or 30% meal; plus approximately 1.6 grams dry pinto beans (soaked for 24 hours in water) for larval food; plus the appropriated amount of water to have a moist mixture. This mixture was placed in plant pots (6 cm×6 cm×8 cm ht). Twenty fungus gnat larvae were added to the mixture in each of the pots. Pots were placed in 1-quart canning jars with organdy top. Numbers of adults emerging were recorded daily. Soil mix was oven-dried overnight before use. Experiment set up on Feb. 28, 2002.

Means in a column followed by the same letter are not significantly different (P=0.05) using protected LSD.

TABLE 11

Incorporation of meal into soil experiment (n = 10).

| Treatment | Mean number fungus gnat adults emerged per pot | percent survival (larvae to adult) |
|---|---|---|
| S. alba 1% (batch 2) | 15.6 ± 0.7 a | 78.0 |
| S. alba 3% (batch 2) | 15.3 ± 0.6 ab | 78.0 |
| B. juncea 1% | 14.8 ± 1.1 ab | 73.5 |
| B. napus (D. Essex) 3% | 14.3 ± 0.9 ab | 71.5 |
| B. napus 6% (Athena) | 14.0 ± 1.1 ab | 70.0 |
| S. alba 6% (batch 2) | 12.7 ± 0.9 b | 63.5 |

TABLE 11-continued

Incorporation of meal into soil experiment (n = 10).

| Treatment | Mean number fungus gnat adults emerged per pot | percent survival (larvae to adult) |
|---|---|---|
| B. napus (D. Essex) 1% | 12.5 ± 1.6 b | 62.5 |
| B. napus (D. Essex) 6% | 7.9 ± 1.5 c | 39.5 |
| B. juncea 3% | 0.7 ± 0.6 d | 3.5 |
| B. juncea 6% | 0.0 ± 0.0 d | 0.0 |

Treatments consisted of approximately 18 grams dry weight of a Sunshine mix no. 2/composted bark mixture (7:3); mixed with 10, 20, or 30% meal; plus 4 halves of pinto beans (soaked for 24 hours in water) for larval food; plus the appropriated amount of water to have a moist mixture. This mixture was placed in plant pots (6 cm×6 cm×8 cm ht). Twenty fungus gnat larvae were added to the mixture in each of the pots. Pots were placed in 1-quart canning jars with sealed tops for 24 hours, at which time organdy cloth replaced the lid. Numbers of adults emerging were recorded daily. Soil mix was oven-dried overnight before use. First five reps were set up on March 5 and second five reps were set up on Mar. 13, 2002.

Means in a column followed by the same letter are not significantly different (P=0.05) using protected LSD.

TABLE 12

Meal top-dressing and meal-incorporation into soil surface experiment (n = 4).

| Treatment | Mean number fungus gnat adults emerged per pot | Mean % survival (larvae to adult) | Mean dry wt. Root |
|---|---|---|---|
| No meal, no disturbance | 13.3 ± 0.9 a | 66.3 | * |
| No meal, disturbance | 13.0 ± 1.6 a | 65.0 | |
| B. juncea 1%, top-dressing | 9.3 ± 1.4 ab | 46.3 | |
| B. juncea 1%, incorporated 6-7 mm | 7.8 ± 2.4 bc | 38.8 | |
| B. juncea 3%, top-dressing | 3.8 ± 1.9 cd | 18.8 | |
| B. juncea 3%, incorporated 6-7 mm | 5.8 ± 1.8 bcd | 28.8 | |
| B. juncea 6%, top-dressing | 2.3 ± 1.3 d | 11.3 | |
| B. juncea 6%, incorporated 6-7 mm | 2.8 ± 1.3 d | 13.8 | |

Pinto bean seeds were planted into soil mixture (19 or 20 grams dry weight) in plant pots (6 cm×6 cm×8 cm ht) on March 9 (block 1) and Mar. 21, 2002 (block2). Soil mixture consisted of Sunshine mix no. 2/composted bark mixture (7:3). Twenty fungus gnat larvae were added March 25 (block 1) and April 2 (block 2) to the soil mixture (~1-2 cm deep) in each of the pots. Pots were placed in 1-quart canning jars with organdy top. Numbers of adults emerging were recorded daily. Soil mix was oven-dried overnight before use. Twenty-five ml water was added to soil surface of each pot (block 1) on March 28, March 31, April 3, and April 7. Twenty ml water was added to soil surface of each pot (block 2) on April 5, April 8, April 11, and April 14.

*=root not weighed

Means in a column followed by the same letter are not significantly different (P=0.05) using protected LSD.

Example 8

It was expected that *Sinapis alba* meal would produce an isothiocyanate that would inhibit mycelial growth of this fungal pathogen. However, no such effect was observed, thus prompting a determination of the fate of 4-OH benzyl isothiocyanate.

Mycelial Growth of *Fusarium oxysporum* in the Presence of Different Meals

*F. oxysporum* strains #9051C, #9243G, #9321A and #9312 F were obtained from forest nurseries in which this fungal pathogen is a problem. Toxicity of meal volatiles against mycelial growth was determined in closed containers. Growth was determined by measuring colony diameters.

Figure 26:
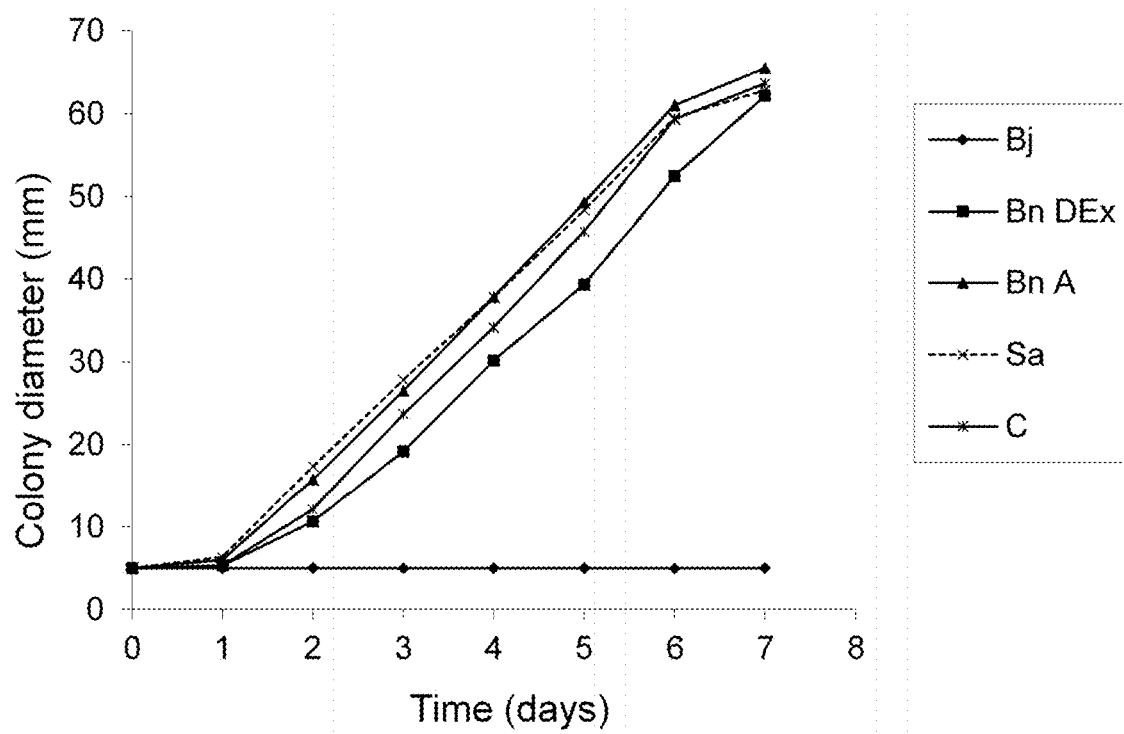
FIG. 26 is a plot of colony diameter versus time (days) showing inhibition of *F. oxysporum* mycelial growth by volatile products from *B. juncea* Pacific Gold meal. Bj=*B. juncea* Pacific Gold; Bn DEx=*B. napus* Dwarf Essex; Bn A=*B. napus* Athena; Sa=*S. alba* IdaGold; C=Control without meal.

FIG. 26 shows that *B. juncea* Pacific Gold meal completed suppressed mycelial growth of *F. oxysporum* in these bioassays. *B. napus* Dwarf Essex had a slight effect on growth. No effect of *S. alba* on mycelial growth was observed in current bioassays. It is possible that volatile products from *S. alba* are minimal and that fungal inhibition may occur if non-volatile glucosinolate hydrolysis products bioassayed. However, this seems unlikely given the fact that little effect on fungus gnats and nematodes was observed when using *S. alba* meal. All isolates behaved similarly.

Example 9

Glasshouse Seed Meal Toxicity on Plant Growth

Plant health can be affected by a variety of soil-borne pests and diseases, including: bacteria, fungi, nematodes, insects, and weeds. Much is now know about the effect of glucosinolate breakdown products on a wide range of soil-borne pests and diseases. However, there has been little effort made to determine the effect of these compounds on crop plants planted after soil treatment. This study was designed to determine the effect of time after planting on crop plant growth.

Sunshine mix potting soil was incorporated with 1-ton, 2-ton, and 4-ton equivalent of *Brassica napus, Brassica juncea*, and *Sinapis alba*, seed meals and potting mix with no amendment as control. After incorporation, the seedling flats were filled and randomly arranged on a bench. Seeds of canola (*B. napus*), oriental mustard (*B. juncea*), yellow mustard (*S. alba*), lettuce (*Lactuca sative*), sugar beet (*Beta vulgaris*) and corn (*Zea mays*) were planted into amended soil treatments 1 day, 2 day, and 4 days after incorporation. Plant counts were recorded daily and after 22 days above ground biomass was determined on each sample. The experimental design was a 3 replicate split plot design with days after treatment as main plots and soil amendment as sub-plots.

Seedling emergence and plant growth of canola, oriental mustard and yellow mustard were all greatly affected when planted into amended soils compared to the control. Soil amended with *S. alba* meal showed lowest plant survival levels whereby less that 30% of seedlings either failed to emerge or survive compared to the control where 100% survival was found. *B. napus*-amended soils resulted in over 80% plant survival, while *B. juncea* was intermediate with just over 51% plant survival. A similar result occurred in corn and sugar beet, where *S. alba* amended soil showed significantly lower plant survival compared to *B. juncea*- or *B. napus*-amended soils. Lettuce emergence was very poor even in the control treatment and plant survival levels were not significantly different over any treatment, albeit that they were all very low. Increasing meal amendment rate significantly reduced plant survival in all species examined. However, lowest survival occurred with *S. alba* meal treatments.

Plant dry weight 22 days after planting showed a similar trend to plant counts. Averaged over amendment rates, plants grown in *B. juncea*-amended soil had above ground biomass which was only 35% that of the control. Plants grown in *B. napus*-amended soils were only one quarter the biomass of the control plants while plants grown in *S. alba*-amended soil were less than 5% dry matter of the control. All seed meals therefore interfered with plant growth even when planting was delayed for 4 days after the initial soil treatment. Plant stunting was not significantly different when seeds were planted immediately after soil amendment or when planting was delayed for 4 days after treatment. Corn and sugar beet plants were stunted in *B. juncea*- and *S. alba*-amended soils in a similar manner Canola, both mustards, sugar beet and corn plant dry weights were reduced with increased concentrations of either *B. juncea* or *S. alba* meal. It was noted, however, that the lowest concentration of *S. alba* meals resulted in plant dry weights equal to the highest concentration of the other seed meals. Plants grown in *B. napus*-amended soils were significantly higher dry matter than the control. *B. napus* seed meal had significantly lower concentration of glucosinolates compared to the two mustard meals studied. It is possible that the concentration or type of glucosinolate in *B. napus* does inhibit germination but not growth after emergence. As all seed meals are high in nitrogen this might explain the larger plants grown in *B. napus*-amended soils.

Overall, all three meals have potential to significantly reduce seedling emergence and plant survival in amended soils. *S. alba* was most effective in killing either seeds or seedlings and had the most detrimental effect on plant growth. Soils amended with *S. alba* meal could offer an alternative biological herbicide. However, more needs to be done to examine the phytotoxicity effect of Brassicaceae seed meal soil amendments and their effect on the crop that is to be planted after treatment.

Herbicidal Efficacy of *Brassica* Seed Meal in Glasshouse Studies.

Sterilized potting compost was infected with uniform numbers of wild oat and pigweed seeds. After the seeds and compost were mixed they were amended with *S. alba* IdaGold (yellow mustard), *B. juncea* Pacific Gold (Oriental mustard) or *B. napus* Athena (canola) seed meals at a rate of 1.0 ton or 0.5 ton an acre equivalent and weeds seeds allowed to germinate and grow for four weeks. Each treatment combination, along with a no treatment control was grown in a four replicate randomized block design with each plot being a seedling flat 36×20 cm.

After four weeks the number and dry weight of wild oat plants and pigweed plants was recorded. Amending soil with 1 ton of *B. juncea* Pacific Gold meal reduced wild oat populations from 96 in the control to 16. Neither rate of IdaGold amendment showed the same degree of wild oat elimination. In sharp contrast, when the broadleaf weed (pigweed) was considered, the reverse was true whereby the Pacific Gold was less effective than the control in controlling weed numbers and a significantly higher weed biomass was produced in the Pacific Gold soil treatments. In the case of pigweed, IdaGold was most effective, reducing population numbers by almost 90% compared to the Pacific Gold treatment. These studies are currently being repeated to confirm the striking results that one mustard type is controlling grassy weeds while the other is specific to broadleaf weeds.

Initial Field Studies

Initial field studies were conducted to investigate: (1) the effect of different *Brassica* species seed meals on establishment and growth of potato, corn, strawberry, recrop cherry, cabbage, rutabaga, lettuce, field beans, and spring wheat; and (2) to evaluate herbicidal potential of using different *Brassica* seed meals Potato and Sweet Corn One super sweet corn cultivar and three potato cultivars ('Yukon Gold', 'White Rose', and 'IdaRed') were planted into ridged seed beds. Prior to ridging, the complete plot area was divided into strips 20 feet wide. Each strip was assigned to a specific seed meal treatment. Seed meal treatments were: (1) *Brassica napus* seed meal at 1 ton/acre; (2) *B. napus* seed meal at 2 ton/acre; (3) *B. juncea* seed meal at 1 ton/acre; (4) *B. juncea* seed meal at 2 ton/acre; (5) *Sinapis alba* seed meal at 1 ton/acre; (6) *Sinapis alba* seed meal at 2 ton/acre; (7) a chemical treatment control; and (8) a no chemical control. The seed meal was applied by hand application. The ridges were drawn and the whole plot area irrigated with approximately 2 inches of irrigation water. The corn and potato cultivars were planted at right angles to the seed meal treatments 21 days after treatment. The experimental design therefore was a strip plot design and was replicated twice.

Strawberry and Cherry

Two strawberry cultivars ('June Bearing' and 'Ever Bearing') and one self-pollinating 'Bing' cherry cultivar were chosen for this study. The strawberry research area was divided into eight 20 foot wide strips×36 feet long. Each strip was associated with a different seed meal treatment (*B. napus, B. juncea, S. alba* and a non-treatment control). Seed meal was applied by hand at a rate of 1 ton/acre, the seed meal worked in by tillage and ridges were drawn. Strawberry plants which had previously been hardened were planted by hand into the ridges 22 days after treatment. The experimental design was a strip plot design with cultivars arranged at random within blocks, and four replicates. Each plot was 20 feet×2 rows.

An area of ground was divided into 20×20 feet units. Each unit was treated with either 1 ton/acre of each *B. juncea* or *S. alba* seed meal, 2 ton/acre of each seed meal, and a non-treatment control (i.e. 2 seed meals types×2 application rates, plus a control). This was replicated twice.

On-farm testing of Pacific Gold and IdaGold seed meal as a pesticide/nematicide in recrop orchards was initiated at The Dalles in Oregon. The complete trial covered 9 acres which was divided into 18×0.5 acre plots. In the fall of 2002 a randomized complete block design was superimposed on the trial area with 5 treatments: (1) the standard chemical nematicide, Telone®; (2) Pacific Gold meal at 1 ton/acre rate applied in the fall; (3) Pacific Gold meal at 1 ton/acre rate applied in the spring (4) Pacific Gold meal at 0.5 ton/acre rate applied in the fall and the spring (5) IdaGold meal at 1 ton/acre rate applied in the fall; (6) IdaGold meal at 1 ton/acre rate applied in the spring (7) IdaGold meal at 0.5 ton/acre rate applied in the fall and the spring (9) winter wheat cover crop; and (9) a no treatment control, with each treatment replicated twice.

As of the date of this report, the fall and spring seed meal rates have been applied. Three weeks after the fall treatment, samples of soil were taken from each plot for nematode analyses. A further soil sample was taken after spring treatments and Telone application. The new cherry trees will be transplanted in Mid-May.

Vegetables and Wheat

Five crops were chosen for this study (rutabaga, cabbage, bean, lettuce and wheat). Wheat was included as we wanted to include a monocot and also as wheat is highly adapted to this region. The trial area was divided into 5 treatment strips 20 feet wide. Treatments were: *B. napus, B. juncea* and *S. alba* seed meals at 1 ton/acre rate, plus a chemical control treatment and a non-treatment control. Each treatment was replicated twice. Seed meal was applied by hand and rototilled to a depth of 4 inches prior to being irrigated (1 inch). Crops were planted using a double disc seed drill 21 days after treatment.

Variates Recorded

On each trial, general plant health was visibly assessed on a daily basis for 21 days after emergence. Plant emergence rates were recorded on all trials. Crop yield was recorded on all crops as they became marketable. Ant disease on plants or harvested product was recorded.

Weed plant counts were recorded on a 1-m$^2$ plot area on all plots at weekly intervals. Weed biomass was taken 10 weeks after planting. Weed plants from 1 m$^2$ were clipped at ground level, bagged, and oven dried before weights were recorded.

Crop emergence of potato and corn were not affected by any of the seed application treatments. Indeed, the smallest and later emerging crops were always in the non-treatment control. Overall there was no significant difference in crop emergence or establishment over all treatments.

All seed meal treatments resulted in a significant reduction in the number of weed plants compared to the non-treatment control in both potato and corn. Amongst the seed meal treatments, *S. alba* meal was most effective in weed control and indeed was not significantly higher than the chemical control in either potato (Sencor) or corn (Harmony Extra). Least effect weed control was in the *B. juncea* treatments where over 3 times the weed plants were found compared to *S. alba*.

None of the strawberry plants transplanted in failed to establish in any treatment. It was evident in the few days after transplanting that there was visibly more browning around the leaf margin. This browning was most striking in the Ever Bearing cultivar which has large thin leaves compared to June Bearing. The symptoms were markedly stronger in the *S. alba* treatments compared to the other seed meals used.

Weed control in the strawberry trial was striking. On average the non-treatment control had 35 weed plants/m$^2$. The chemical control (actually hand weeding) had almost none. The *B. napus* treatments had on average 12 weeds/m$^2$, The *B. juncea* slightly better with 8 weed plants/m$^2$. However, there were almost no weeds in the *S. alba*, which was equivalent to the chemical control.

Weed control in the cherry orchard was equally as striking as the strawberry with mass weed populations (mainly pigweed and lambsquarter) in all treatments except the IdaGold treatments. Initial nematode counts after the fall treatments of The Dalles on-farm test were are follows: no treatment control=1,203 nematodes; winter wheat cover crop=1,197 nematodes; IdaGold soil amendment=701 nematodes; Pacific Gold soil amendment=232 nematodes. The Telone treatment is spring only.

Crop emergence was more erratic in the vegetables than in the other crops. Overall, however, there was no significant difference between soil treatments and crop emergence, and indeed if a trend did exist it was that the 'better' crop emergence was in the S. alba treatments compared to the other seed meal treatments.

Weed control in the vegetable trial was as striking as that in the strawberry plots. The results were very similar to those above. Weeds were devastating in all crops without any treatment, averaging more than 25 weeds/m². Both B. napus and B. juncea treatments resulted in a significant reduction in weed populations; they were both significantly higher than the complete control. S. alba meal treatment resulted in the elimination of almost all weeds in all crops and was not significantly different from the complete control treatment.

Corn yield in the Pacific Gold and Athena treatment was not significantly different from the chemical control, but the IdaGold corn was significantly lower yielding as was the no treatment control. Highest potato yield was obtained after Pacific Gold and Athena application, followed by IdaGold, the chemical control and lowest potato yield was with the no treatment control. Highest yield of strawberry was with the chemical control. All three seed meal treatments produced higher strawberry yield than the control. IdaGold treatment produced significantly higher cabbage yield than other treatments as did the chemical control with lettuce production. Lettuce appeared to be least sensitive to IdaGold meal treatments.

The overall conclusion from this study is that Brassica seed meals have little or no effect on the crop of crops planted or transplanted 21 days after treatment. Both B. napus and B. juncea seed meal treatments significantly reduced weed populations over a no treatment control. S. alba seed meal treatments almost eliminated all weed growth and the weeds that did emerge could easily have been explained by less than fully effective seed meal incorporation.

Overall, seed meal treatments were as productive as the chemical control for most crops. IdaGold treatment appeared to have residual negative effect on corn and lettuce growth.

Example 10

Two studies were conducted to examine the effects of amending soil with defatted Brassicaceae meal on the establishment of weed seedlings. Based on the observations of greenhouse and field experiments, the meal from *Sinapis alba* "IdaGold" appears to have the greatest potential for effective weed control. In an effort to better understand the dose response of weed seed germination and establishment, the following studies were performed:

1. Incorporation of IdaGold meal at 8 rates with 3 weed species
2. Top-dressing of IdaGold meal at 8 rates with 2 weed species Meal was obtained from the University of Idaho's onsite crushing facility. The seed used to produce the meal was #1 grade seed purchased through the Genesee Union. Meal rates were determined as a percentage of the dry soil weight and ranged from 0 to 0.97%. The highest rate is equivalent to an application of 4 tons per acre incorporated into the top three inches of soil.

Redroot pigweed, wild oat, and common lambsquarter seed was received from an associate of Dr. Donn Thill. A germination test was performed following the 1$^{st}$ experiment, which showed a lack of germination viability in the stock of common lambsquarter seed. Weed seeds were either hand-counted (wild oat) or carefully weighed (pigweed and lambsquarter) into proper allotments and then planted into rows randomly positioned within the trays.

The soil used was obtained from a local organically-managed farm (Mary Jane Butter's Paradise Farm) and was passed through a 2 mm screen. While this soil has not been chemically or texturally analyzed, it appears to be a fine silt-loam rich with organic matter (an analyses is planned for this soil). Weighed allotments of soil were amended with meal either by mixing them together in a container prior to pouring the soil into a seedling tray (incorporation) or by sprinkling the meal onto the soil after it had been poured and leveled in the tray (top-dressing).

Each tray thus consisted of two rows of each weed species and was amended with meal at a rate of 0, 0.06, 0.12, 0.18, 0.24, 0.30, 0.49, 0.73, or 0.97% of dry soil weight. Each treatment was replicated five times, and the experiment was conducted following a randomized complete block design.

The moment the trays were watered initiated time zero, the trays were subsequently watered daily for two weeks; afterwards they were watered twice a week.

Although daily emergence data was collected, the final total of emerged and established seedlings is of much greater interest. It should be noted that a delay in the emergence of weeds may provide the desired level of weed control in some situations. However, in this study the focus was on the dose response of the weeds to the amount of meal amendment. Both species (pigweed and wild oat) responded negatively to increasing levels of meal amendment (FIG. 6).

TABLE 13

| | Number of established seedlings vs. dose of meal | | | |
|---|---|---|---|---|
| Dose | pigweed-inc | pigweed-top | wild oat-inc | wild oat-top |
| 0 | 84.2 | 27 | 25.2 | 26.2 |
| 0.06 | 68.4 | 24.2 | 30 | 24.2 |
| 0.12 | 26.2 | 11 | 19.8 | 26.6 |
| 0.18 | 10.8 | 10.4 | 22.4 | 22 |
| 0.24 | 9 | 10.2 | 19.8 | 21.2 |
| 0.3 | 7.6 | 2 | 12.8 | 17.8 |
| 0.49 | 1.2 | 1.4 | 9 | 11.8 |
| 0.73 | 1.2 | 1.2 | 2.8 | 11.8 |
| 0.97 | 2 | 0.6 | 3.8 | 6.6 |

*S. alba* or "IdaGold" meal is useful as a soil amendment for weed control. The methodology might be modified by changing the depth of planting, scarifying the seed prior to use, etc. Since there appears to be no appreciable difference between incorporation and top-dressing, future top-dressing only may be the most practical method of applying.

Example 11

This example discusses using the method for pest control comprising disclosed embodiments of the present invention by extracting intact glucosinolates, such as 4-hydroxybenzyl glucosinolate, and applying the extract to soil either as a top dressing or by incorporating the extract a certain depth into the soil, such as from 0.25 to about 5.0 centimeters. Plant tissue is extracted with an extractant, such as an aqueous alcohol, e.g. methanol, solution. The plant tissue optionally may be pressed, such as by cold pressing, prior to extraction. Selected glucosinolates are obtained as extracts by this procedure.

In a first embodiment, extracted glucosinolate is applied to selected soil at a desired application rate selected for pest control. Thereafter, an effective amount of myrosinase enzyme also is added to the soil to produce active biopesticides.

Alternatively, the extracted glucosinolate can be combined with the myrosinase to form a mixture, and then the mixture is applied to selected soil at a desired application rate selected for pest control.

Another possibility for effective utilization of *S. alba* meal as an herbicide is to add water to the meal, causing enzymatic hydrolysis of 4-OH benzyl glucosinolate by the contained myrosinase. The resulting aqueous solution that now contains $SCN^-$ could then be applied as a spray to soil or to the weed itself. To facilitate such a process a volume of *S. alba* meal could be enclosed or encapsulated in a container that would allow water penetration. The capsule or container could be dropped in a known volume of water, thus promoting hydrolysis of the contained 4-OH benzyl glucosinolate and providing a recommended $SCN^-$ rate adequate for weed control. The resulting $SCN^-$ solution could then be sprayed on soil or directly on weeds without the need to apply meal.

Example 12

Seed meal from *S. alba* (yellow mustard) was evaluated for effects on seed germination and establishment compared to a no treatment control. Seedling flats (26 by 52 by 7.5 cm) were filled with potting media and then 4 grams each of wild oat or 1 gram of redroot pigweed seeds were sprinkled on the media surface and thoroughly mixed into the potting media. The meal treatments were 0.5 and 1.0 metric t/ha, equivalents weight by area, of IdaGold yellow mustard meal. Seed meal was thoroughly mixed into the soil in flats after seeding the weed seeds. The experimental design was a randomized complete block with four replicates, and the experiment was conducted three times Immediately after incorporation of the meal, all flats were watered equally with 3 centimeters of water to encourage glucosinolate hydrolysis. Seedlings emergence counts and above ground plant biomass after three weeks growth were determined.

Only the higher application of *S. alba* seed meal resulted in a significant reduction in redroot pigweed (Table 14). However, both the *S. alba* application rates produced significantly lower redroot pigweed biomass compared to the no-treatment control. Similarly, the *S. alba* meal amended soils resulted in significantly lower wild oat seedlings and significantly lower weed biomass compared to the no-treatment control. In conclusion, *S. alba* seed meal showed significant herbicidal effects compared to a no-treatment control.

TABLE 14

Weed count and biomass from meal amended soils and a no-treatment control.

| | | Redroot Pigweed | | Wild Oat | |
|---|---|---|---|---|---|
| Treatment | Rate Mt ha$^{-1}$ | Weed count Plant m$^2$ | Weed Biomass g m$^2$ | Weed count Plant m$^2$ | Weed Biomass g m$^2$ |
| No meal | 0 | 150 a | 0.729 a | 99 a | 9.6 a |
| *S. alba* meal | 0.5 | 99 ab | 0.159 b | 67 b | 6.6 b |
| | 1.0 | 45 b | 0.139 b | 41 c | 4.3 c |

Means within columns with different letters are significantly different (P < 0.05)

Example 13

Two ton/acre equivalent seed meal rates of *Sinapis alba* L. (IdaGold) were used as soil amendment treatments along with a no-treatment control. The *S. alba* meal was incorporated by hilling or tilling the top two inches of soil. Two weeks after seed meal was incorporated crops were planted, including lettuce (*Lactuca sativa*), field beans (*Phaseolus* spp.), cabbage (*B. oleracea*), strawberries (*Fragaria×ananassa Duchesne*), corn (*Zea mays*), and potatoes (*Solanum tuberosum*). Experiments were planted in a split plot design with soil treatments assigned as main plots and crops assigned to sub-plots. All crops were hand harvested.

Weed density was significantly different between *S. alba* soil amendment treatments compared to the no-treatment control in all crops examined (Table 15). In conclusion *S. alba* (IdaGold) was most effective in reducing weed populations and in most cases weed control was excellent.

TABLE 15

Weed population in different crops planted into soil amended with *S. alba* seed meal and from a no-treatment control.

| Crop | *S. alba* meal amended soils Weed plants m$^2$ | No-treatment control |
|---|---|---|
| Corn | 14.0 a | 2.2 b |
| Potato | 13.5 a | 2.0 b |
| Strawberry | 34.5 a | 1.0 b |
| Cabbage | 21.2 a | 0.1 b |
| Lettuce | 28.0 a | 0.2 b |
| Field Bean | 32.3 a | 0.2 b |
| Average | 23.9 a | 0.9 b |

Means within rows with different letters are significantly different (P < 0.05)

Example 14

Studies were established in a greenhouse at the University of Idaho, Moscow, Id. in winter 2006 to evaluate the effect of water extractions of *S. alba* seed meal on the growth of common lambsquarters, 'Yaya' carrot, green 'Summer Crisp' lettuce, and spring wheat. Greenhouse flats were 20 by 28 by 5 cm, arranged in a randomized complete block design with six replications. *S. alba* mustard seed meal applications equivalent to 2.2, 4.5, 9, 13.5, and 18 metric tons per hectare were extracted with tap-water at room temperature (20° C.) at a 7.3:1 ratio of seed meal to tap-water. Extraction was performed by shaking seed meal in Erlenmeyer flasks for 30 minutes at 300 rpm. Supernatants were strained 3 times with a 28 mesh screen to remove precipitated material. Twenty seeds of common lambsquarters, 'Yaya' carrot, green 'Summer Crisp' lettuce, and spring wheat were planted in rows 14 days prior to treatment. Greenhouse temperatures were set at 23/12° C. day and night, respectively, with a photoperiod of 16/8 hours day and night, respectively. Above ground seedling biomass was harvested by species 16 days after treatment. Seedling biomass was dried at 15° C. for 72 hours and weighed.

Figure 27:
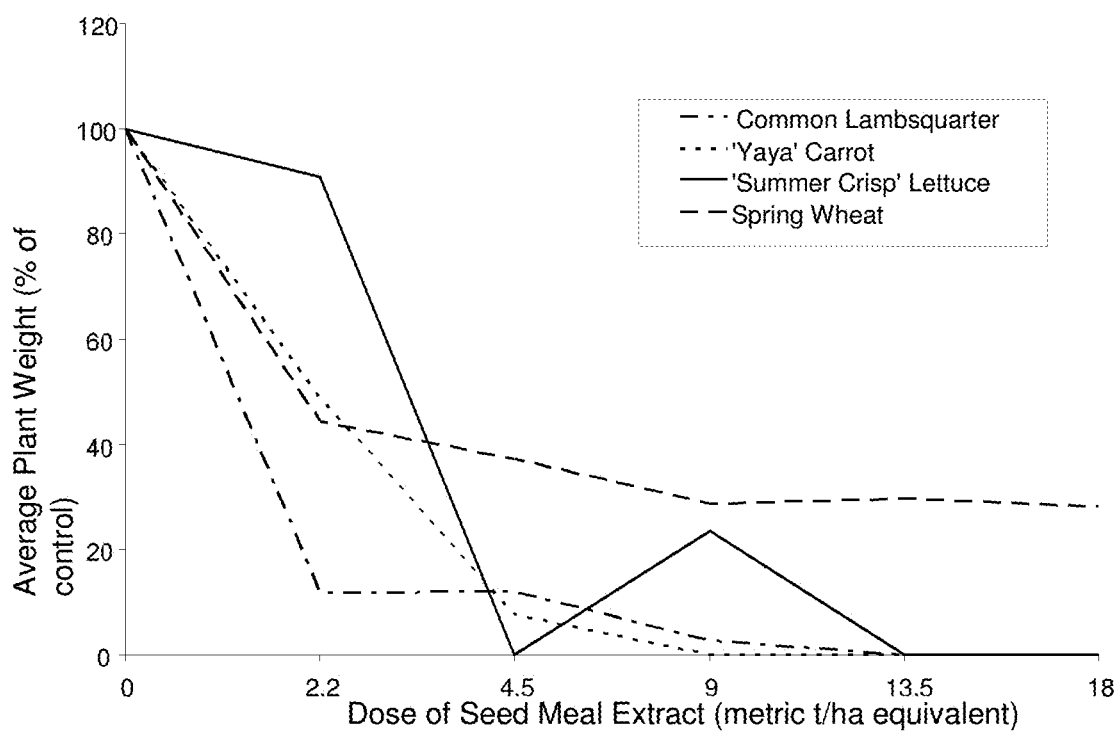
FIG. 27 is a graph of average plant weight versus dose of seed meal extract, illustrating the toxicity of *S. alba* seed meal extract to various crops and weeds.

A general trend of decreasing plant biomass with increasing doses of *S. alba* seed meal supernatant extraction was observed (FIG. 27). The large reduction in plant biomass between a dose of 0 and a dose of 2.2 metric t/ha indicates that reduction in plant biomass at doses lower than 2.2 metric t/ha may be possible. While common lambsquarters, 'Yaya' Carrot, and 'Summer Crisp' lettuce were all reduced to a plant biomass of 0 with a dose of 13.5 metric t/ha, spring wheat showed some tolerance to the treatment, as indicated by an almost flat dose response between 9 and 18 metric t/ha.

Examples 15-17

The potatoes for Examples 15-17 were hand harvested and shipped three days later. The potatoes were placed in a dark room at 50° F. for one month to cure and to allow gradual removal of field heat.

Example 15

B. juncea Extracts Control Potato Sprouting

Figure 28:
FIG. 28 is a photograph of Oliense potatoes treated with 1 gram of *B. juncea* in 7 mL water, illustrating the very small amount of sprouting observed after two months post treatment.
Figure 29:
FIG. 29 is a photograph of Oliense potatoes not treated with *B. juncea*, illustrating the amount of sprouting observed after two month in storage under the same conditions as the potatoes shown in FIG. 28.
Figure 30:
FIG. 30 is a photograph of Cecil potatoes treated with 1 gram of *B. juncea* in 7 mL water, illustrating that after seven weeks in storage the *B. juncea* had prevented sprouting.
Figure 31:
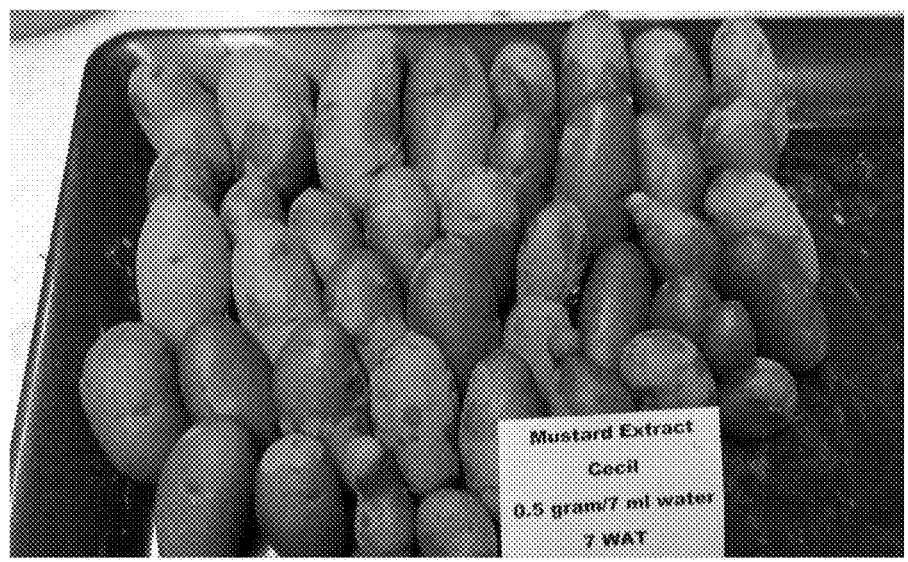
FIG. 31 is a photograph of Cecil potatoes treated with 0.5 grams of *B. juncea* in 7 mL water, illustrating that after seven weeks in storage the *B. juncea* had prevented sprouting.
Figure 32:
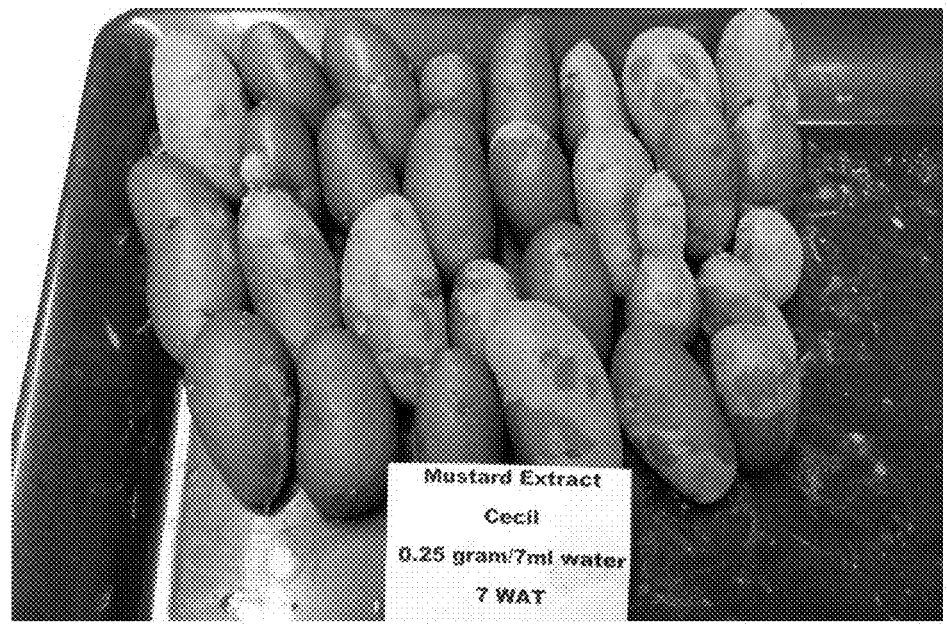
FIG. 32 is a photograph of Cecil potatoes treated with 0.25 grams of *B. juncea* in 7 mL water, illustrating that after seven weeks in storage only a small amount of sprouting was observed.
Figure 33:
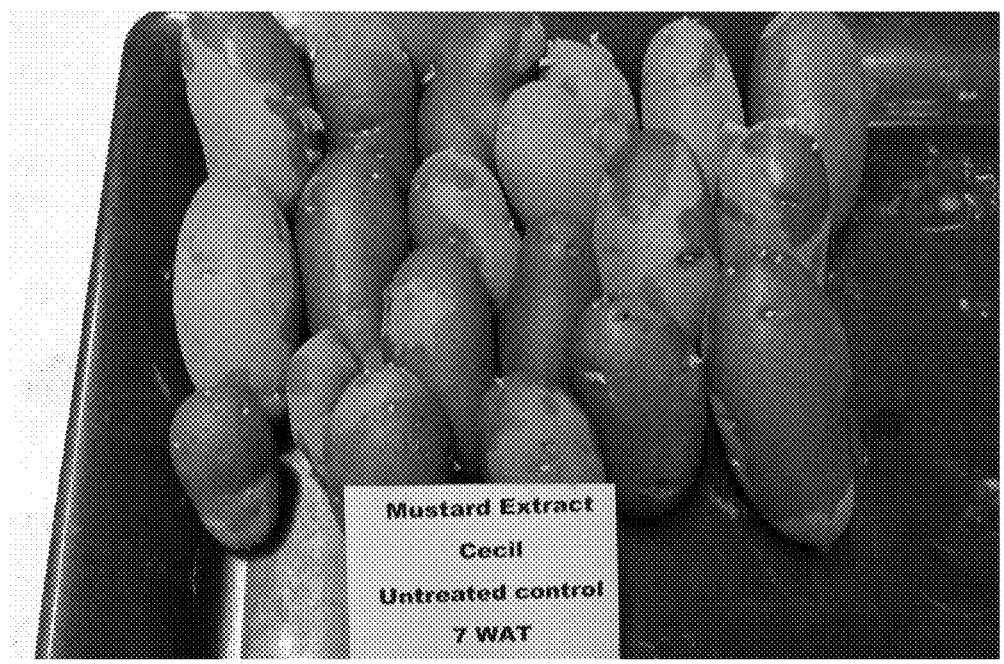
FIG. 33 is a photograph of Cecil potatoes not treated with *B. juncea*, illustrating that after seven weeks in storage considerable sprouting was observed.

One gallon jars each holding approximately 4 lbs of potatoes were used for testing. Three jars were filled with actively sprouting potatoes to serve as the untreated controls. Three additional jars served as the extract treatments. One gram of the B. juncea meal extract (360 µmol sinigrin/g) was weighed into a jar lid. The filled lid was placed in bottom center of each treatment jar. A wire rack was placed over the lid containing the meal. Actively sprouting potatoes were placed within the jar. Using a pipette, 7 ml of water was added to a long ventilation tube that was strategically placed over the meal. After water was added, the ventilation tubes were stoppered and the jars were sealed for 24 hours. The potatoes were stored for 24 hours at 51° F. in a dark room after which time the stoppers were removed from the ventilation tubes. The jars were then stored at 55° F. and monitored. Sprouting was observed at four and eight weeks after treatment (WAT) (Table 16). The B. juncea extract provided nearly complete sprout inhibition indicating excellent potential to be used as a sprout inhibitor of stored potatoes (FIGS. 28 and 29).

TABLE 16

Sprouting index of potatoes treated with B. juncea extract as measured 4 and 8 weeks after treatment.

| Treatment | Sprouting Index[a] | |
|---|---|---|
| | 4 WAT | 8 WAT |
| Untreated control | 2.7 | 3.8 |
| B. juncea treatment | 0.5 | 0 |

[a]Sprouting index is on a scale from 0-40, with 0 indicating no sprouting and 5 indicating a level of concern to processors.

Example 16

Dose-Dependent Response of B. juncea Extracts to Control Potato Sprouting

Potatoes were dormant at the start of the testing. Three jars were filled with tubers, but were untreated in order to serve as controls. Nine additional jars were filled with potatoes. Jars were filled as previously described in Example 15, but one half of a petri dish was used to hold the extract inside the jar. The following treatments were included, with 3 jars or replicates each: 1 g extract/7 ml of water; 0.5 g of extract/7 ml of water; and 0.25 g extract/7 ml of water.

The jars were all sealed for 24 hours then unsealed, hooked to ventilation, and placed in the dark at 50° F. for observation of sprouting. No sprouting was observed in the 0.5 and 1.0 g extract treatment groups, and much reduced sprouting was observed in the 0.25 g extract treatment group (Table 17 and FIGS. 30-33).

TABLE 17

Sprouting index of potatoes treated with B. juncea extract as measured 3 and 7 weeks after treatment.

| Treatment | Sprouting Index[a] | |
|---|---|---|
| | 3 WAT | 7 WAT |
| Untreated control | 7.4 | 8.3 |
| B. juncea treatment, 0.25 g | 0.3 | 1.4 |
| B. juncea treatment, 0.5 g | 0 | 0 |
| B. juncea treatment, 1.0 g | 0 | 0 |

[a]Sprouting index is on a scale from 0-40, with 0 indicating no sprouting and 5 indicating a level of concern to processors.

Example 17

B. juncea Extracts Control Sprouting in Large Scale Potato Storage

Figure 34:
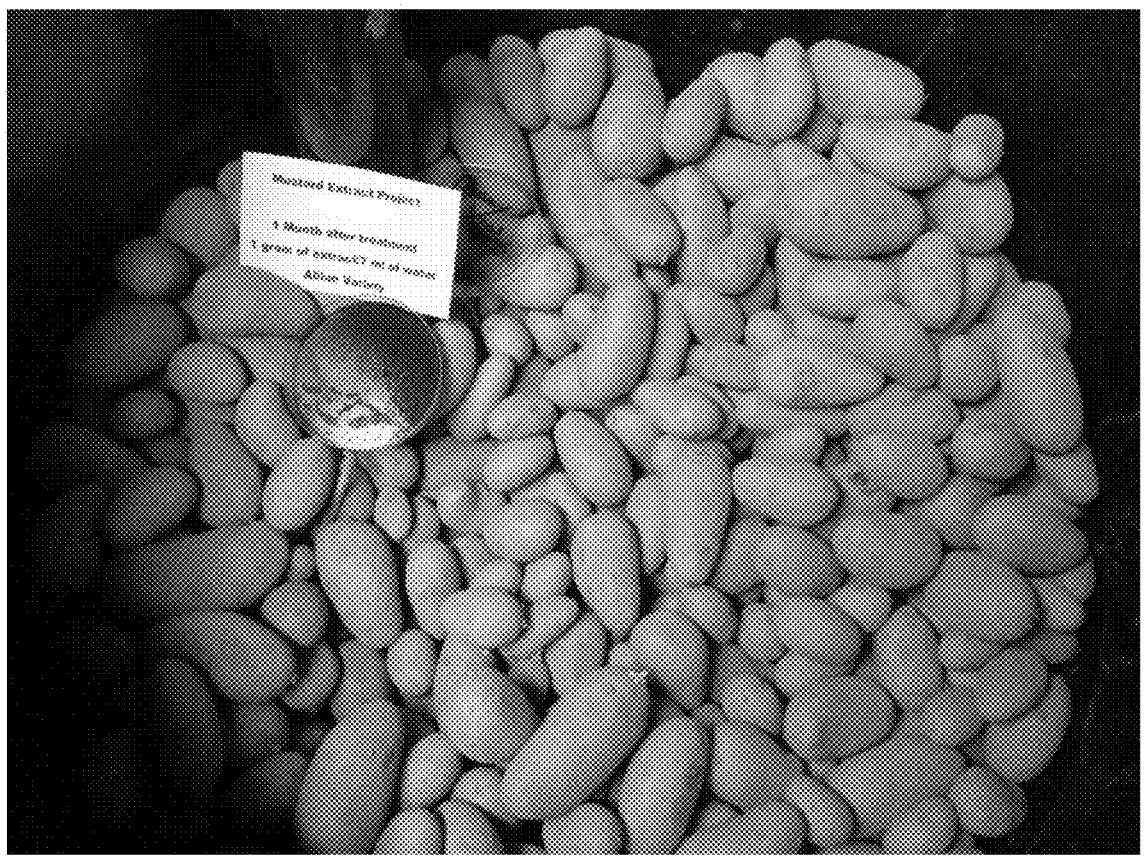
FIG. 34 is a photograph of Allian potatoes treated with 1 gram of mustard extract in 7 mL water, illustrating the small amount of sprouting after one month in storage.
Figure 35:
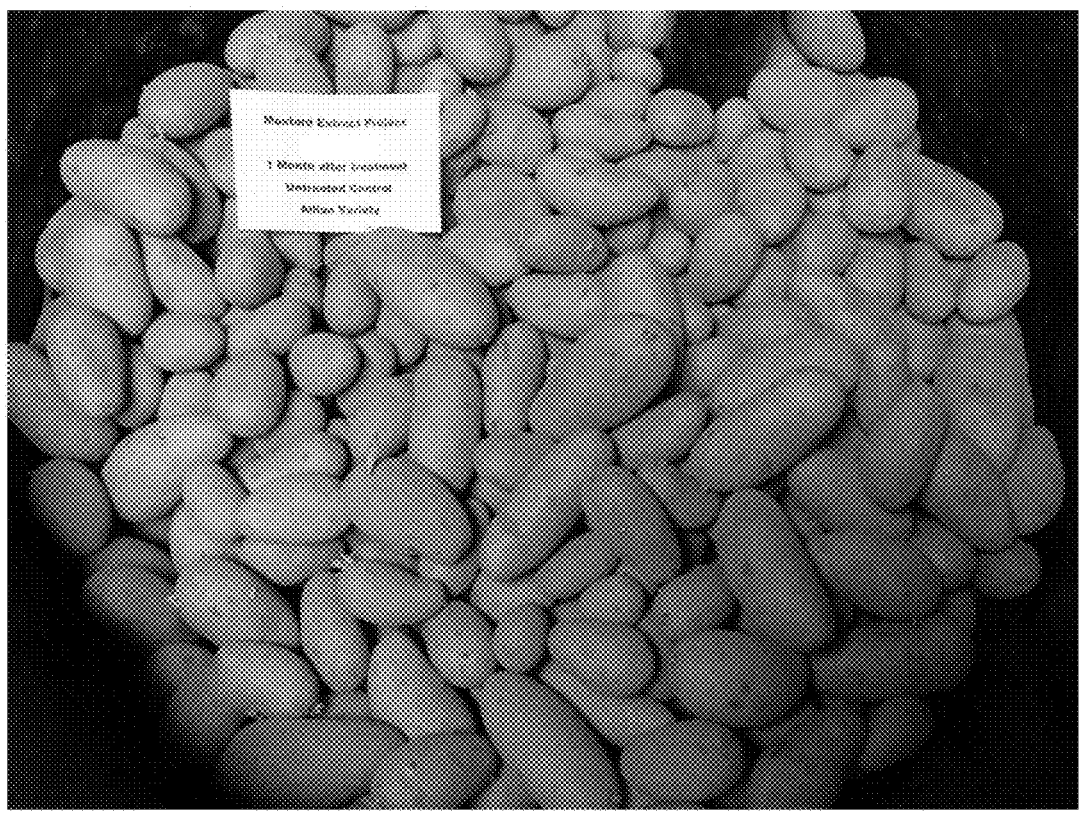
FIG. 35 is a photograph of Allian potatoes not treated with mustard extract, illustrating the substantial amount of sprouting after one month in storage.
Figure 36:
FIG. 36 is a photograph of a *Nicotiana* plant before treatment with *S. alba* extract, illustrating normal growth.
Figure 37:
FIG. 37 is a photograph of the *Nicotiana* plant from FIG. 36 two weeks after treatment with *S. alba* extract, illustrating the onset of the phytotoxic effects.
Figure 38:
FIG. 38 is a photograph of the *Nicotiana* plant from FIG. 36 three weeks after treatment with *S. alba* extract, illustrating the herbicidal properties of the extract.
Figure 39:
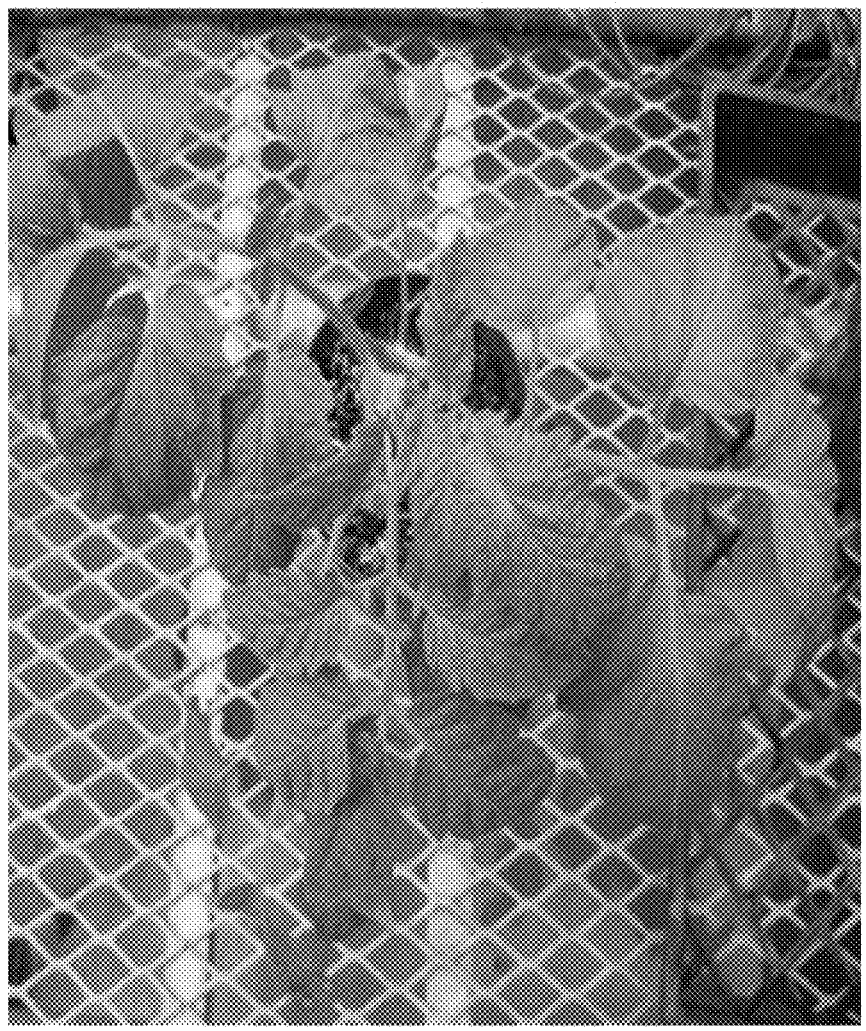
FIG. 39 is a photograph of a tomato plant before treatment with *S. alba* extract.
Figure 40:
FIG. 40 is a photograph of the tomato plant from FIG. 39 two weeks after treatment with *S. alba* extract, showing the yellowing of some leaves, illustrating the onset of the phytotoxic effects.
Figure 41:
FIG. 41 is a photograph of the tomato plant from FIG. 39 three weeks after treatment with *S. alba* extract, illustrating the herbicidal properties of the extract.

Two hundred pounds of potatoes placed within a metal barrel were treated with 1 gram of mustard extract containing about 898 µmol sinigrin/g. Two 200-lb barrels were filled with potatoes exhibiting initial stages of sprouting. One barrel served as an untreated control and potatoes in the other were treated. The treatment group received 1 gram of extract to which was added 7 ml of water in a petri dish. The barrel was immediately sealed. The barrels were stored at a room temperature of 69° F. for 24 hours after which time they were opened for ventilation. Barrels were then stored in the dark at 50° F. At one month after treatment, the treatment group showed substantially less sprouting than the untreated control (FIGS. 34 and 35). Inhibition continued to the second month after treatment. The treatment group was given a second extract treatment eight weeks after the initial treatment. The second treatment was the same as the first, namely 1 gram extract/7 ml H$_2$O and sealed for 24 hour of exposure. One month after the second treatment, the potatoes were examined Potatoes in the treatment group continued to show inhibition of sprouting. The average sprout index of the treatment group was 0.7, whereas the untreated control had a sprout index of 2.0. The barrel was resealed for another two months and evaluated. The untreated control had a sprout index 12.7, whereas the treatment group had a sprout index of 1.4 at the top, 3.4 in the middle, and 2.4 at the bottom (Table 18). Twenty weeks after treatment the extract-treated potatoes had a sprouting index deemed acceptable by processors as it was below a sprouting index of 5. In contrast, the untreated control group showed unacceptable sprouting for processing, with a sprouting index of 12.7.

TABLE 18

Sprouting index of potatoes treated with B. juncea extract as measured in the barrel study.

| Treatment | Sprouting Index (weeks after treatment)[a] | | | | |
|---|---|---|---|---|---|
| | Initial | 4 | 8 | 12 | 20 |
| Untreated control | 3 | 9.7 | 4.0 | 2.0 | 12.7 |
| B. juncea treatment, 1 g | 2.2 | 3.0 | 1.9 | 0.7 | 2.4 |

[a]Sprouting index is on a scale from 0-40, with 0 indicating no sprouting and 5 indicating a level of concern to processors. Values represent averages of three estimates measured at different depths in the barrel.

Example 18

*Sinapis alba* Extract as a Herbicide

An aqueous *Sinapis alba* extract was applied to the leaves of *Nicotiana* plants and leaves of tomato plants by spraying the plants with an aqueous extract. Progressive phytotoxicity was observed over time, illustrating that the *S. alba* extract had herbicidal properties (FIGS. 36-41). Typically, after two weeks, the previously health leaves started to turn yellow. After three weeks, there was substantial yellowing of the leaves, illustrating the herbicidal properties of the *S. alba* extract. This also illustrated that plants in addition to liverwort were susceptible to the herbicidal properties of *S. alba* extracts.

XI. Statements

Statement 1. A method, comprising:
extracting a plant material selected from *Sinapis alba* or *Brassica juncea* with an extraction solvent comprising an alcohol and water to produce an extract; and
concentrating and drying the extract by spray drying or belt drying to produce a non-deliquescent solid.

Statement 2. The method of statement 1, wherein the extraction solvent comprises from 10% to 90% alcohol and from 90% to 10% water.

Statement 3. The method of statement 1 or statement 2, wherein the alcohol comprises methanol, ethanol or a combination thereof.

Statement 4. The method of any one of statements 1-3, wherein the plant material is a seed meal.

Statement 5. The method of any one of statements 1-4, comprising homogenizing and/or grinding the plant material prior to the extraction.

Statement 6. The method of any one of statements 1-5, wherein the plant material is *Sinapis alba*, and the extraction solvent comprises 30% ethanol and 70% water.

Statement 7. The method of statement 6, wherein the extract is spray dried.

Statement 8. The method of statement 6 or statement 7, comprising extracting *Sinapis alba* for a period of up to at least 3 days, and wherein the extract comprises 4-hydroxybenzyl alcohol and 4-hydroxyphenylacetonitrile.

Statement 9. The method of any one of statements 1-5, wherein the plant material is *Brassica juncea* and the extraction solvent is 70% ethanol and 30% water.

Statement 10. The method of statement 9, wherein the extract is belt dried.

Statement 11. A method, comprising applying to liverwort or the soil adjacent thereto, an extract comprising 4-hydroxybenzyl alcohol and 4-hydroxyphenylacetonitrile produced by the method of any one of statements 1-8.

Statement 12. A method of preventing or substantially inhibiting potato sprouts during storage, the method comprising applying to the potatoes *Sinapis alba* seed meal, *Brassica juncea* seed meal, or the extract produced by the method of any one of statements 1-10.

Statement 13. The method of statement 11 or statement 12, wherein the extract is formulated for application by a sprinkler or spraying device by dissolved the extract in water.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising exposing stored vegetables in a storage facility to an atmosphere comprising products generated by exposing a first effective amount of *Brassica juncea* seed meal, *Brassica juncea* seed meal extract, or a combination thereof to water, thereby substantially preventing sprouting in vegetables stored in the facility.

2. The method of claim 1, wherein the vegetables are bulb vegetables, corm vegetables, tuber vegetables, or a combination thereof.

3. The method of claim 1, wherein the vegetables are potatoes.

4. The method of claim 1, wherein exposing the stored vegetables comprises generating the products in the presence of the vegetables such that the products are released into the storage facility atmosphere.

5. The method of claim 1, wherein exposing the vegetables comprises spraying or fogging the products into an atmosphere of the vegetable storage facility to form the atmosphere comprising the products.

6. The method of claim 1, comprising using an amount of *Brassica juncea* seed meal, *Brassica juncea* seed meal extract or a combination thereof, of from greater than zero to one gram per 225 kg of vegetables.

7. The method of claim 6, wherein the amount of *Brassica juncea* seed meal, *Brassica juncea* seed meal extract or a combination thereof, is from one gram per 1.5 kg to one gram per 50 kg of vegetables.

8. The method of claim 6, wherein the amount of *Brassica juncea* seed meal, *Brassica juncea* seed meal extract or a combination thereof, is from 0.02 grams per kg of vegetables to 0.667 grams per kg of vegetables.

9. The method of claim 1, wherein generating the products comprises using an amount of water of from 1 mL to 30 mL per gram of *Brassica juncea* seed meal, *Brassica juncea* seed meal extract or a combination thereof.

10. The method of claim 1, further comprising exposing the stored vegetables to products generated by exposing a second amount of *Brassica juncea* seed meal, *Brassica juncea* seed meal extract or a combination thereof to a second amount of water.

11. The method of claim 10, wherein a time period between exposing the stored vegetables to the products generated from the first amount of *Brassica juncea* seed meal, *Brassica juncea* seed meal extract or a combination thereof and the products generated from the second amount of *Brassica juncea* seed meal, *Brassica juncea* seed meal extract or a combination thereof is sufficient to substantially maintain inhibition of vegetable sprouting.

12. The method of claim 11, wherein the time period is from 1 week to 12 weeks.

13. The method of claim 1, wherein the *Brassica juncea* seed meal, *Brassica juncea* seed meal extract or a combination thereof, comprises an amount of sinigrin sufficient to produce an amount of hydrolysis products sufficient to substantially prevent vegetable sprouting.

14. The method of claim 13, wherein the amount of sinigrin is from greater than zero to 2000 μmol per gram of *Brassica juncea* seed meal, *Brassica juncea* seed meal extract or a combination thereof.

15. The method of claim 1, wherein the vegetables comprise potatoes selected from Russet Burbank, Russet Norkotah, Western Russet, Cal Red, Red La Soda, Norland, French Fingerling, Russian Banana, Purple Peruvian, Yukon Gold, Yukon Gem, Ruby Crescent, Yellow Finn, Huckleberry, Ida Rose, Klondike Golddust, Klondike Rose, Milva, Ranger Russet, All Blue, Alturas Russet, Brannock Russet, Bintje, Blazer Russet, Classic Russet, Clearwater Russet, Onaway, Elba, Carola, Oliense, Cecil, Allian, Agata, Russet Alpine, Rosara, Chieftan, Dark Red Norland, Red Norland, Innovator, Shepody, California White, or a combination thereof.

16. The method of claim 1, wherein the first products comprise allyl isothiocyanate.

17. A method, comprising spraying or fogging an atmosphere of a potato storage facility with an aqueous composition comprising a volatile product formed by a mixture of water and *Brassica* seed meal, *Brassica juncea* seed meal or a combination thereof, thereby preventing potatoes stored in the storage facility from sprouting.

18. The method of claim 17, wherein the volatile product comprises 2-propenyl isothiocyanate.

19. A method, comprising exposing potatoes stored in a storage facility to 2-propenyl isothiocyanate in an amount sufficient to substantially prevent potatoes stored in the storage facility from sprouting.

20. The method of claim 19, wherein the 2-propenyl isothiocyanate is adjacent to the potatoes.

\* \* \* \* \*